United States Patent
Terricabras Belart et al.

(10) Patent No.: US 7,662,814 B2
(45) Date of Patent: Feb. 16, 2010

(54) 4-AMINOTHIENO[2,3-D]PYRIMIDINE-6-CARBONITRILE DERIVATIVES AS PDE7 INHIBITORS

(75) Inventors: Emma Terricabras Belart, Barcelona (ES); Victor Manuel Segarra Matamoros, Barcelona (ES); Julio Alvarez-Builla Gomez, Madrid (ES); Juan Jose Vaquero Lopez, Madrid (ES); Jose Miguel Minguez Ortega, Madrid (ES)

(73) Assignee: Laboratorios Almirall, S.A., Barcelona (ES)

(*) Notice: Subject to any disclaimer, the term of this patent is extended or adjusted under 35 U.S.C. 154(b) by 571 days.

(21) Appl. No.: 10/542,940

(22) PCT Filed: Jan. 23, 2004

(86) PCT No.: PCT/EP2004/000584

§ 371 (c)(1),
(2), (4) Date: Apr. 10, 2006

(87) PCT Pub. No.: WO2004/065391

PCT Pub. Date: Aug. 5, 2004

(65) Prior Publication Data

US 2006/0229306 A1 Oct. 12, 2006

(30) Foreign Application Priority Data

Jan. 23, 2003 (ES) .................... 200300172

(51) Int. Cl.
*C07D 495/04* (2006.01)
*C07D 413/04* (2006.01)
*A61K 31/519* (2006.01)
*A61K 31/497* (2006.01)
*A61K 31/5355* (2006.01)
*A61P 35/04* (2006.01)
*A61P 37/06* (2006.01)
*A61P 3/10* (2006.01)
*A61P 17/06* (2006.01)
*A61P 11/06* (2006.01)

(52) U.S. Cl. ............ 514/234.2; 514/260.1; 514/252.16; 544/117; 544/278

(58) Field of Classification Search ............ 544/117, 544/278; 514/234.2, 252.16, 260.1
See application file for complete search history.

(56) References Cited

U.S. PATENT DOCUMENTS 6,130,223 A 10/2000 Jonas et al.
6,531,498 B1 3/2003 Eggenweiler et al.
6,753,340 B2 6/2004 Vergne et al.
6,884,800 B1 4/2005 Eggenweiler et al.
7,122,565 B2 10/2006 Vergne et al.

FOREIGN PATENT DOCUMENTS

| EP | 447891 | * | 9/1991 |
| EP | 0 728 759 | | 8/1996 |
| EP | 1329454 A1 | | 4/2002 |
| EP | 1329454 | * | 7/2003 |
| WO | WO98/17668 | | 4/1998 |

OTHER PUBLICATIONS

Search Report for PCT/EP2004/000584, mailed Jul. 2, 2004.
Search Report for Spanish Application No. 200300172 dated Jul. 27, 2004 (instant priority document).
esp@cenet Abstract for WO98/17668, published on Apr. 30, 1998.
Martinez, A. et al. "Benzyl Derivatives of 2,1,3-Benzo- and Benzothieno[3,2-a]thiadiazine 2,2-Dioxides: First Phosphodiesterase 7 Inhibitors," *J. Medicinal Chemistry* 43(4): 683-689 (2000).
Nakata, A. et al. "Potential role of phosphodiesterase 7 in human T cell function: comparative effects fo two phosphodiesterase inhibitors," *Clinical and Experimental Immunology* 128: 460-466 (2002).
Smith, SJ et al. "Ubiquitous expression of phosphodiesterase 7A in human proinflammatory and immune cells," *Am. J. Physiol. Lung Cell Mol. Physiol.* 284: L279-L289 (2003).

* cited by examiner

*Primary Examiner*—Brenda L Coleman
*Assistant Examiner*—Susanna Moore
(74) *Attorney, Agent, or Firm*—Finnegan, Henderson, Farabow, Garrett & Dunner, L.L.P.

(57) ABSTRACT

New 4-aminothieno[2,3-d]pyrimidine-6-carbonitrile derivatives having the chemical structure of general formula (I), and pharmaceutically acceptable salts thereof are disclosed, as well as processes for their preparation and to pharmaceutical compositions containing them and their use in the treatment, prevention or suppression of pathological conditions, diseases and disorders susceptible of being improved by inhibition of PDE7.

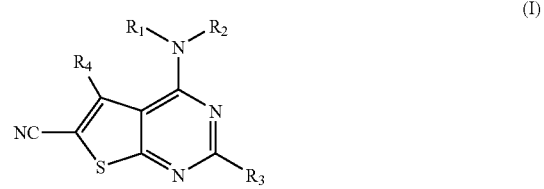

(I)

13 Claims, No Drawings

4-AMINOTHIENO[2,3-D]PYRIMIDINE-6-CARBONITRILE DERIVATIVES AS PDE7 INHIBITORS

This application is a national stage application under 35 U.S.C. 0 371 of international application number PCT/EP2004/000584, filed on Jan. 23, 2004, which claims the benefit of priority from Spanish application number P200300172, filed on Jan. 23, 2003.

The present invention relates to new 4-aminothieno[2,3d] pyrimidine-6-carbonitrile derivatives, to processes for their preparation and to pharmaceutical compositions containing them. These compounds are potent and selective inhibitors of phosphodiesterase 7 (PDE7) and are thus useful in the treatment, prevention or suppression of pathological conditions, diseases and disorders susceptible of being improved by inhibition of PDE7.

Cyclic nucleotide phosphodiesterases (PDEs) comprise a superfamily of proteins that share the ability to hydrolyze cyclic nucleotides like cAMP (cyclic adenosine 3'-5'-monophosphate) and/or cGMP (cyclic-guanosine 3'-5'-monophosphate). Cyclic nucleotides are intracellular second messengers essential to integrate signals from many extracellular stimuli (e.g. hormones, neurotransmitters) into appropriate cellular responses. Inhibition of PDEs leads to an increase in the intracellular level of cyclic nucleotides, modulating many cellular signalling pathways and in some instances leading to beneficial therapeutic effects (*Trends in Medicinal Chemistry Drug News Perspect December* 2000 13 (10)).

Proteins within the phosphodiesterase superfamily share at least 40% sequence homology and a common catalytic domain. Among phosphodiesterases, homologies above 65% define phosphodiesterase families, where proteins show other common structural features. So far, 11 families have been described, each including one or more genes and several protein isoforms. For example, the PDE1 family includes at least three genes, PDE1A, PDE1B and PDE1C. PDE1A gives rise to two isoforms, PDE1A1 and PDE1A2 which have different tissue distribution (Dousa. 1999. *Kidney International* 55: 29-62).

Members of the PDE7 family specifically hydrolyze cAMP with high affinity ($K_m$~0.2 µM). Unlike other cAMP specific phosphodiesterases like PDE3 and PDE4, PDE7 proteins are not inhibited by cGMP. The first member of the PDE7 family, PDE7A2, was identified in 1993 (Michaeli et al. *J Biol Chem.* 1993 Jun. 15; 268(17):12925-32). To date, two genes and up to five isoforms have been described (Han et al. *J Biol Chem.* 1997 Jun. 27; 272(26):16152-7; Hetman et al. *Proc Natl Acad Sci USA.* 2000 Jan. 4; 97(1):472-6; Sasaki et al. *Biochem Biophys Res Commun.* 2000 May 19; 271(3): 575-83, U.S. Pat. No. 6,146,876).

PDE7 isoforms are expressed in many different human tissues, including airway epithelial cells, brain, heart, liver, pancreas, thyroid, skeletal muscle, and lymphoid tissue (Miró et al. *Synapse.* 2001 June; 40(3):201-14.; Fuhrmann et al. *Am J Respir Cell Mol Biol.* 1999 February; 20(2):292-302; Gardner et al. *Biochem Biophys Res Commun.* 2000 May 27; 272(1):186-92, Han et al. *J Biol Chem.* 1997 Jun. 27; 272(26): 16152-7; Bloom & Beavo. *Proc Natl Acad Sci USA.* 1996 Nov. 26; 93(24):14188-92; Hoffmann et al. *Cell Biochem Biophys.* 1998; 28(2-3):103-13.).

Among PDE7A isoforms, the PDE7A1 protein is expressed in B and T lymphocytes. In particular in CD4+ T cells, PDE7A1 has been shown to be required for cellular activation after T cell receptor dependent stimulation (Lee et al. *Cell Signal* 2002 March; 14(3):277-84; Nakata et al. *Clin Exp Immunol.* 2002 June; 128(3):460-6; Lee et al. *Cell Signal.* 2002 March; 14(3):277-84; Glavas et al. *Proc Natl Acad Sci USA.* 2001 May 22; 98(11):6319-24. Li et al. *Science.* 1999 Feb. 5; 283(5403):848-51; Kanda et al. *Biochem Pharmacol.* 2001 Aug. 15; 62(4):495-507). Even though isoforms of both PDE3 and PDE4 are also expressed in T lymphocytes, only PDE4 and PDE7 appear to be relevant for the functional response of these cells (Giembycz et al. *Br J Pharmacol.* 1996 August; 118(8):1945-58).

It has also been shown that increasing cAMP levels in leukemic cells using PDE4 inhibitors may result in the induction of apoptosis or programmed cell death leading to a therapeutic effect useful for the treatment of chronic lymphocytic leukemia (Lerner et al. *Leuk Lymphoma.* 2000 March; 37(1-2):39-51; Kim & Lerner. *Blood.* 1998 Oct. 1; 92(7):2484-94.).

In view of the tissue distribution and functional role of PDE7 proteins, PDE7 inhibitors of varied chemical structures have been disclosed for the treatment or prevention of pathological conditions, diseases and disorders susceptible to amelioration by inhibition of PDE7 proteins such as asthma, atopic dermatitis, chronic obstructive pulmonary disease, Crohn's disease, type I and type II diabetes, lymphoid leukemia and other forms of cancer, multiple sclerosis, alograft rejection after organ transplantation, psoriasis, rheumatoid arthritis and ulcerative colitis. In particular, given its relevance for T cell function, PDE7 inhibitors may be useful for the treatment of T cell mediated immune diseases and for treatment of diseases of the airway. See, for example, Bioorganic and Medicinal Chemistry Letters, 11 (2001) 1081-1083; J. Med. Chem., 2000, 43, 683-689; Drug Data Report 2002, 24(1): 76/WO 01/74786 A1; Drug Data Report 2002, 24(7): 639/WO 02/28847 A1; Drug Data Report 2002, 24(8): 703/WO 02/40449 A1; Drug Data Report 2002, 24(3): 262/ WO 01/98274 A2.

No compounds having PDE7 inhibition capacity have so far reached the market place but some have been tested biologically.

In spite of the large number of potent and selective inhibitors available for other PDEs like PDE4 and PDE5, some of which are undergoing clinical evaluation, there is still a need for potent PDE7 inhibitors, specifically those effective at low concentrations, preferably in the low nanomolar range.

We have now found that a novel series of 4-aminothieno [2,3-d]pyrimidine-6-carbonitrile derivatives are potent inhibitors of PDE7 enzymes and are therefore useful in the treatment or prevention of pathological conditions, diseases and disorders susceptible of amelioration by inhibition of PDE7 enzymes such as asthma, atopic dermatitis, chronic obstructive pulmonary disease, Crohn's disease, type I and type II diabetes, lymphoid leukemia and other forms of cancer, multiple sclerosis, alograft rejection after organ transplantation, psoriasis, rheumatoid arthritis and ulcerative colitis. In particular, given its relevance for T cell function, PDE7 inhibitors may be useful for the treatment of T cell mediated immune diseases.

The compounds of the present invention can also be used in combination with other drugs known to be effective in the treatment of these diseases. For example, they can be used in combination with one or more compounds selected from PDE4 inhibitors, $A_{2A}$ adenosine receptor antagonists, NSAIDs, COX-2 inhibitors, TNF-α inhibitors and steroids.

Accordingly, the present invention provides novel compounds of formula (I)

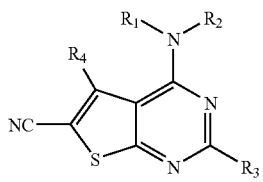

or pharmaceutically acceptable salts thereof wherein
$R_1$ and $R_2$ either
$R_1$ and $R_2$ either
  (a) independently represent:
    (i) a hydrogen atom
    (ii) a group selected from an alkyl, alkenyl or alkynyl groups, which are optionally substituted by one or more, for example 1, 2, 3 or 4, substituents selected from halogen atoms and hydroxy, alkoxy, aryloxy, alkylthio, carboxy, oxo, amino, mono- or di-alkylamino groups;
    (iii) a group of formula
    —$(CH_2)_n R^6$
      wherein n is an integer from 0 to 4 and $R^6$ represents a cycloalkyl or cycloalkenyl group
  or
  (b) $R_1$ and $R_2$ form, together with the nitrogen atom to which they are attached, a 3- to 8-membered ring comprising from 1 to 4 heteroatoms selected from nitrogen, oxygen and sulphur, which ring is optionally substituted by one or more, for example 1, 2, 3 or 4, substituents selected from halogen atoms and alkyl, hydroxy, alkoxy, acyl, hydroxycarbonyl, alkoxycarbonyl, alkylenedioxy, amino, mono- or di-alkylamino, mono- or di-alkylaminoacyl, nitro, cyano or trifluoromethyl groups;
$R_3$ is group of formula
—$(CH_2)_n$-G
  wherein n is an integer from 0 to 4 and G represents a monocyclic or bicyclic aryl or heteroaryl group comprising from zero to four heteroatoms which group is optionally substituted by one or more, for example 1, 2, 3 or 4, substituents selected from:
    (i) halogen atoms;
    (ii) alkyl and alkylene groups, which are optionally substituted by one or more, for example 1, 2, 3 or 4, substituents selected from halogen atoms; and
    (iii) phenyl, hydroxy, hydroxyalkyl, alkoxy, alkylenedioxy, aryloxy, alkylthio, amino, mono- or di-alkylamino, acylamino, nitro, acyl, hydroxycarbonyl, alkoxycarbonyl, cyano, difluoromethoxy or trifluoromethoxy groups;
$R_4$ represents a hydrogen atom or an alkyl or aryl group with the proviso that it is not 5-methyl-2-phenyl-4-morpholin-4-ylthieno[2,3-d]pyrimidine-6-carbonitrile Certain aminothieno[2,3-d]pyrimidine derivatives of similar structure, which do not fall within the scope of the present invention, have been disclosed in WO98/06722, WO00/59912, WO02/49650.

Other aspects of the present invention are a) a process for the preparation of the compounds b) pharmaceutical compositions comprising an effective amount of said compounds, c) the use of said compounds in the manufacture of a medicament for the treatment of diseases susceptible of being improved by inhibition of phosphodiesterases 7 (PDE7); and d) methods of treatment of diseases susceptible to amelioration by inhibition of phosphodiesterases 7 (PDE7), which methods comprise the administration of the compounds of the invention to a subject in need of treatment.

As used herein the term alkyl embraces optionally substituted, linear or branched radicals having 1 to 20 carbon atoms or, preferably 1 to 12 carbon atoms. More preferably alkyl radicals are "lower alkyl" radicals having 1 to 8, preferably 1 to 6 and more preferably 1 to 4 carbon atoms.

Examples include methyl, ethyl, n-propyl, i-propyl, n-butyl, sec-butyl, tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

When it is mentioned that alkyl radicals may be optionally substituted it is meant to include linear or branched alkyl radicals as defined above, which may be unsubstituted or substituted in any position by one or more substituents, for example by 1, 2 or 3 substituents. When two or more substituents are present, each substituent may be the same or different.

The substituent(s) are typically halogen atoms, preferably fluoride atoms, and hydroxy or unsubstituted alkoxy radicals.

As used herein, the term alkenyl embraces optionally substituted, linear or branched, mono or polyunsaturated radicals having 2 to 20 carbon atoms or, preferably 2 to 12 carbon atoms. The term alkenyl embraces radicals having "cis" and "trans" orientations, or alternatively, "E" and "Z" orientations. More preferably alkenyl radicals are "lower alkenyl" radicals having 2 to 8, preferably 2 to 6 and more preferably 2 to 4 carbon atoms. In particular it is preferred that the alkenyl radicals are mono or diunsaturated.

Examples include vinyl, allyl, 1-propenyl, isopropenyl, 1-butenyl, 2-butenyl, 3-butenyl, 1-pentenyl, 2-pentenyl, 3-pentenyl and 4-pentenyl radicals.

When it is mentioned that alkenyl radicals may be optionally substituted it is meant to include linear or branched alkenyl radicals as defined above, which may be unsubstituted or substituted in any position by one or more substituents, for example by 1, 2 or 3 substituents. When two or more substituents are present, each substituent may be the same or different.

The substituent(s) are typically halogen atoms, preferably fluoride atoms, and hydroxy or unsubstituted alkoxy radicals.

As used herein, the term alkynyl embraces optionally substituted, linear or branched, mono or polyunsaturated radicals having 2 to 20 carbon atoms or, preferably 2 to 12 carbon atoms. More preferably, alkynyl radicals are "lower alkynyl" radicals having 2 to 8, preferably 2 to 6 and more preferably 2 to 4 carbon atoms. In particular it is preferred that the alkynyl radicals are mono or diunsaturated.

Examples include 1-propynyl, 2-propynyl, 1-butynyl, 2-butynyl and 3-butynyl radicals.

When it is mentioned that alkynyl radicals may be optionally substituted it is meant to include linear or branched alkynyl radicals as defined above, which may be unsubstituted or substituted in any position by one or more substituents, for example by 1, 2 or 3 substituents. When two or more substituents are present, each substituent may be the same or different.

The substituent(s) are typically halogen atoms, preferably fluoride atoms, and hydroxy or unsubstituted alkoxy radicals.

As used herein, the term alkylene embraces divalent alkyl moieties typically having from 1 to 6, for example from 1 to 4, carbon atoms. Examples of $C_1$-$C_4$ alkylene radicals include methylene, ethylene, propylene, butylene, pentylene and hexylene radicals. An alkylene group is typically unsubstituted.

When an alkylene radical is present as a substituent on another radical it shall be deemed to be a single substituent, rather than a radical formed by two substituents.

As used herein, an alkylenedioxy group is an alkylene group as defined above linked to two oxygen atoms.

As used herein, the term alkoxy (or alkyloxy) embraces optionally substituted, linear or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms. An alkoxy group is typically unsubstituted or substituted with 1, 2 or 3 substituents selected from halogen atoms and hydroxy groups. Preferably it is unsubstituted.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term alkylthio embraces radicals containing an optionally substituted, linear or branched alkyl radicals of 1 to 10 carbon atoms attached to a divalent sulfur atom. More preferred alkylthio radicals are "lower alkylthio" radicals having 1 to 8, preferably 1 to 6 and more preferably 1 to 4 carbon atoms. An alkythio group is typically unsubstituted or substituted with 1, 2 or 3 substituents selected from halogen atoms and hydroxy groups. Preferably it is unsubstituted.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio and 2-hydroxypropylthio.

As used herein, the term monoalkylamino embraces radicals containing an optionally substituted, linear or branched alkyl radicals of 1 to 10 carbon atoms attached to a divalent —NH— radical. More preferred monoalkylamino radicals are "lower monoalkylamino" radicals having 1 to 8, preferably 1 to 6 and more preferably 1 to 4 carbon atoms. A monoalkylamino group is typically unsubstituted or substituted with 1, 2 or 3 substituents selected from halogen atoms and hydroxy groups. Preferably it is unsubstituted.

Preferred optionally substituted monoalkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyethylamino and 2-hydroxypropylamino.

As used herein, the term dialkylamino embraces radicals containing a trivalent nitrogen atoms with two optionally substituted, linear or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical. A dialkylamino group is typically unsubstituted or substituted on one or each alkyl moiety with 1, 2 or 3 substituents selected from halogen atoms and hydroxy groups. Preferably it is unsubstituted.

Preferred optionally substituted dialkylamino radicals include dimethylamino, diethylamino, methyl(ethyl)amino, di(n-propyl)amino, n-propyl(methyl)amino, n-propyl(ethyl) amino, di(i-propyl)amino, i-propyl(methyl)amino, i-propyl (ethyl)amino, di(n-butyl)amino, n-butyl(methyl)amino, n-butyl(ethyl)amino, n-butyl(i-propyl)amino, di(sec-butyl) amino, sec-butyl(methyl)amino, sec-butyl(ethyl)amino, sec-butyl(n-propyl)amino, sec-butyl(i-propyl)amino, di(t-butyl) amino, t-butyl(methyl)amino, t-butyl(ethyl)amino, t-butyl(n-propyl)amino, t-butyl(i-propyl)amino, trifluoromethyl (methyl)amino, trifluoromethyl(ethyl)amino, trifluoromethyl(n-propyl)amino, trifluoromethyl(i-propyl) amino, trifluoromethyl(n-butyl)amino, trifluoromethyl(sec-butyl)amino, difluoromethyl(methyl)amino, difluoromethyl (ethyl)amino, difluoromethyl(n-propyl)amino, difluoromethyl(i-propyl)amino, difluoromethyl(n-butyl)) amino, difluoromethyl(sec-butyl)amino, difluoromethyl(t-butyl)amino, difluoromethyl(trifluoromethyl)amino, hydroxymethyl(methyl)amino, ethyl(hydroxymethyl)amino, hydroxymethyl(n-propyl)amino, hydroxymethyl(i-propyl) amino, n-butyl(hydroxymethyl)amino, sec-butyl(hydroxymethyl)amino, t-butyl(hydroxymethyl)amino, difluoromethyl (hydroxymethyl)amino, hydroxymethyl(trifluoromethyl) amino, hydroxyethyl(methyl)amino, ethyl(hydroxyethyl) amino, hydroxyethyl(n-propyl)amino, hydroxyethyl(i-propyl)amino, n-butyl(hydroxyethyl)amino, sec-butyl (hydroxyethyl)amino, t-butyl(hydroxyethyl)amino, difluoromethyl(hydroxyethyl)amino, hydroxyethyl(trifluoromethyl)amino, hydroxypropyl(methyl)amino, ethyl(hydroxypropyl)amino, hydroxypropyl(n-propyl)amino, hydroxypropyl(i-propyl)amino, n-butyl(hydroxypropyl) amino, sec-butyl(hydroxypropyl)amino, t-butyl(hydroxypropyl)amino, difluoromethyl(hydroxypropyl)amino y hydroxypropyl(trifluoromethyl)amino.

As used herein, the term hydroxyalkyl embraces linear or branched alkyl radicals having 1 to 10 carbon atoms any one of which may be substituted with one or more hydroxyl radicals.

Examples of such radicals include hydroxymethyl, hydroxyethyl, hydroxypropyl, hydroxybutyl and hydroxyhexyl.

As used herein, the term alkoxycarbonyl embraces optionally substituted, linear or branched radicals each having alkyl portions of 1 to 10 carbon atoms and attached to an oxycarbonyl radical. More preferred alkoxycarbonyl radicals are "lower alkoxycarbonyl" radicals having 1 to 8, preferably 1 to 6 and more preferably 1 to 4 carbon atoms. An alkoxy carbonyl group is typically unsubstituted or substituted with 1, 2 or 3 substituents selected from halogen atoms and hydroxy groups. Preferably it is unsubstituted.

Preferred optionally substituted alkoxycarbonyl radicals include methoxycarbonyl, ethoxycarbonyl, n-propoxycarbonyl, i-propoxycarbonyl, n-butoxycarbonyl, sec-butoxycarbonyl, t-butoxycarbonyl, trifluoromethoxycarbonyl, difluoromethoxycarbonyl, hydroxymethoxycarbonyl, 2-hydroxyethoxycarbonyl and 2-hydroxypropoxycarbonyl.

As used herein, the term acyl embraces optionally substituted, linear or branched radicals having 1 to 20 carbon atoms or, preferably 1 to 12 carbon atoms attached to a carbonyl radical. More preferably acyl radicals are "lower acyl" radicals having 2 to 8, preferably 2 to 6 and more preferably 2 to 4 carbon atoms. Thus, it is typically a radical of formula —COR. An acyl group is typically unsubstituted.

Preferred optionally substituted acyl radicals include acetyl, propionyl, butiryl, isobutiryl, isovaleryl, pivaloyil, valeryl, lauryl, myristyl, stearyl and palmityl.

As used herein an alkoxyacyl group is an alkoxy group as defined above linked to an acyl group as defined above. An acylamino group is an acyl group as defined above linked to an amino group. A mono- or di-alkylaminoacyl group is a mono- or di-alkylamino group as defined above, linked to an acyl group as defined above.

As used herein, the term aryl radical embraces typically a $C_5$-$C_{14}$ monocyclic or polycyclic aryl radical such as phenyl, naphthyl, anthranyl and phenanthryl. A polycyclic radical is considered to be an aryl radical if at least one of the cycles is an aryl.

An aryl radical may be unsubstituted or substituted by one or more, for example 1, 2, 3 or 4, substituents. When an aryl radical carries 2 or more substituents, the substituents may be the same or different. The substituents are typically selected from halogen atoms, phenyl, hydroxy, hydroxyalkyl, alkoxy, alkylenedioxy, aryloxy, alkylthio, amino, mono- or di-alkylamino, acylamino, nitro, acyl, hydroxycarbonyl, alkoxycarbonyl, cyano, difluoromethoxy and trifluoromethoxy groups and alkyl and alkylene groups which are themselves unsubstituted or substituted by one or more halogen atoms. Where a phenyl group is present as a substituent, typically only one such phenyl substituent is present. Preferred substituents on an aryl group are unsubstituted $C_1$-$C_4$ alkoxy, unsubstituted $C_1$-$C_4$ alkyl, nitro, halogen, trifluoromethyl, unsubstituted $C_1$-$C_3$ alkylenedioxy and unsubstituted alkoxycarbonyl wherein the alkyl portion has from 1 to 4 carbon atoms.

As used herein the term aryloxy embraces an aryl group as defined above connected to an oxygen atom.

As used herein, the term heteroaryl radical embraces monocyclic or polycyclic 5- to 14-membered ring system comprising at least one heteroaromatic ring and containing at least one heteroatom selected from O, S and N. A heteroaryl radical may be a single ring or two or more fused rings wherein at least one ring contains a heteroatom. A polycyclic radical is considered to be an heteroaryl radical if at least one of the cycles is an heteroaryl.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, indolyl, indazolyl, purinyl, imidazolidinyl, pteridinyl and pyrazolyl radicals.

Oxadiazolyl, oxazolyl, pyridyl, pyrrolyl, imidazolyl, thiazolyl, thiadiazolyl, thienyl, furanyl, pyrazinyl and pyrimidinyl radicals are preferred.

A heteroaryl radical may be unsubstituted or substituted by one or more, for example 1, 2, 3 or 4, substituents. When a heteroaryl radical carries 2 or more substituents, the substituents may be the same or different. The substituents are typically selected from halogen atoms, phenyl, hydroxy, hydroxyalkyl, alkoxy, alkylenedioxy, aryloxy, alkylthio, amino, mono- or di-alkylamino, acylamino, nitro, acyl, hydroxycarbonyl, alkoxycarbonyl, cyano, difluoromethoxy and trifluoromethoxy groups and alkyl and alkylene groups which are themselves unsubstituted or substituted by one or more halogen atoms. Where a phenyl group is present as a substituent, typically only one such phenyl substituent is present. Preferred substituents on a heteroaryl group are unsubstituted $C_1$-$C_4$ alkoxy, unsubstituted $C_1$-$C_4$ alkyl, nitro, halogen, trifluoromethyl, unsubstituted $C_1$-$C_3$ alkylenedioxy and unsubstituted alkoxycarbonyl wherein the alkyl portion has from 1 to 4 carbon atoms. Preferably, a heteroaryl group is unsubstituted.

As used herein, the term cycloalkyl embraces saturated carbocyclic radicals and, unless otherwise specified, a cycloalkyl radical typically has from 3 to 7 carbon atoms.

Examples include cyclopropyl, cyclobutyl, cyclopentyl, cyclohexyl and cycloheptyl. It is preferably cyclopropyl, cyclopentyl or cyclohexyl. A cycloalkyl radical may be unsubstituted or substituted and is typically unsubstituted. When a cycloalkyl radical carries 2 or more substituents, the substituents may be the same or different.

As used herein, the term cycloalkenyl embraces partially unsaturated carbocyclic radicals and, unless otherwise specified, a cycloalkenyl radical typically has from 3 to 7 carbon atoms.

Examples include cyclobutenyl, cyclopentenyl, cyclohexenyl and cycloheptenyl. It is preferably cyclopentenyl or cyclohexenyl. A cycloalkenyl group may be unsubstituted or substituted and is typically unsubstituted. When a cycloalkenyl radical carries 2 or more substituents, the substituents may be the same or different.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

Typically when a cyclic radical is bridged by an alkylene radical, the bridging alkylene radical is attached to the ring at non-adjacent atoms.

As used herein, the term halogen atom embraces chlorine, fluorine, bromine or iodine atom typically a fluorine, chlorine or bromine atom, most preferably chlorine or fluorine. The term halo when used as a prefix has the same meaning.

Compounds containing one or more chiral centre may be used in enantiomerically or diastereoisomerically pure form, or in the form of a mixture of isomers.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkylamines, arylalkyl amines and heterocyclic amines.

Particular individual compounds of the invention include:
4-(4-Ethylpiperazin-1-yl)-5-methyl-2-phenylthieno[2,3-d]pyrimidine-6-carbonitrile
4-(4-Ethylpiperazin-1-yl)-2-(4-methoxyphenyl)-5-methylthieno[2,3-d]pyrimidine-6-carbonitrile
4-(Diethylamino)-5-methyl-2-phenylthieno[2,3-d]pyrimidine-6-carbonitrile
5-Methyl-2-phenyl-4-piperidin-1-ylthieno[2,3-d]pyrimidine-6-carbonitrile
5-Methyl-2-(4-nitrophenyl)-4-piperidin-1-ylthieno[2,3-d]pyrimidine-6-carbonitrile
2-(4-Methoxyphenyl)-5-methyl-4-piperidin-1-ylthieno[2,3d]pyrimidine-6-carbonitrile
5-Methyl-4-(4-methylpiperazin-1-yl)-2-(4-nitrophenyl)thieno[2,3-d]pyrimidine-6-carbonitrile
5-Methyl-2-phenyl-4-piperazin-1-ylthieno[2,3-d]pyrimidine-6-carbonitrile
2-(4-Methoxyphenyl)-5-methyl-4-(4-methylpiperazin-1-yl)thieno[2,3-d]pyrimidine-6-carbonitrile
4-(Diethylamino)-2-(4-methoxyphenyl)-5-methylthieno[2,3-d]pyrimidine-6-carbonitrile 2-(4-Methoxyphenyl)-5-methyl-4-pyrrolidin-1-ylthieno[2,3-d]pyrimidine-6-carbonitrile
2-(4-Methoxyphenyl)-5-methyl-4-piperazin-1-ylthieno[2,3-d]pyrimidine-6-carbonitrile
5-Methyl-2-(4-nitrophenyl)-4-piperazin-1-ylthieno[2,3-d]pyrimidine-6-carbonitrile
4-(Dibutylamino)-2-(4-methoxyphenyl)-5-methylthieno[2,3-d]pyrimidine-6-carbonitrile
2-(4-Chlorophenyl)-5-methyl-4-(4-methylpiperazin-1-yl)thieno[2,3-d]pyrimidine-6-carbonitrile
2-(3,4-Dimethoxyphenyl)-5-methyl-4-(4-methylpiperazin-1-yl)thieno[2,3-d]pyrimidine-6-carbonitrile
4-[Ethyl(methyl)amino]-2-(4-methoxyphenyl)-5-methylthieno[2,3-d]pyrimidine-6-carbonitrile
4-(Diethylamino)-5-methyl-2-(4-nitrophenyl)thieno[2,3-d]pyrimidine-6-carbonitrile
2-(4-Chlorophenyl)-4-(diethylamino)-5-methylthieno[2,3d]pyrimidine-6-carbonitrile
4-(Diethylamino)-2-(3,4-dimethoxyphenyl)-5-methylthieno[2,3-d]pyrimidine-6-carbonitrile
4-(Dimethylamino)-2-(4-methoxyphenyl)-5-methylthieno[2,3-d]pyrimidine-6-carbonitrile
2-(4-Methoxyphenyl)-5-methyl-4-morpholin-4-ylthieno[2,3-d]pyrimidine-6-carbonitrile
2-(4-Chlorophenyl)-5-methyl-4-morpholin-4-ylthieno[2,3-d]pyrimidine-6-carbonitrile
2-(4-Methoxyphenyl)-5-methyl-4-[methyl(prop-2-ynyl)amino]thieno[2,3-d]pyrimidine-6-carbonitrile
4-[(2-Hydroxyethyl)(methyl)amino]-2-(4-methoxyphenyl)-5-methylthieno[2,3-d]pyrimidine-6-carbonitrile
2-(3,4-Dimethoxyphenyl)-4-[ethyl(methyl)amino]-5-methylthieno[2,3-d]pyrimidine-6-carbonitrile
5-Methyl-2-(4-methylphenyl)-4-(4-methylpiperazin-1-yl)thieno[2,3-d]pyrimidine-6-carbonitrile
4-(Diethylamino)-5-methyl-2-[4-(trifluoromethyl)phenyl]thieno[2,3-d]pyrimidine-6-carbonitrile
4-[Allyl(methyl)amino]-2-(4-methoxyphenyl)-5-methylthieno[2,3-d]pyrimidine-6-carbonitrile
2-(3,4-Dimethoxyphenyl)-4-[(2-hydroxyethyl)(methyl)amino]-5-methylthieno[2,3-d]pyrimidine-6-carbonitrile
2-(3,4-Dimethoxyphenyl)-5-methyl-4-morpholin-4-ylthieno[2,3-d]pyrimidine-6-carbonitrile
5-Methyl-2-(4-methylphenyl)-4-morpholin-4-ylthieno[2,3-d]pyrimidine-6-carbonitrile
5-Methyl-4-(4-methylpiperazin-1-yl)-2-[4-(trifluoromethyl)phenyl]thieno[2,3-d]pyrimidine-6-carbonitrile
2-(1,3-Benzodioxol-5-yl)-5-methyl-4-(4-methylpiperazin-1-yl)thieno[2,3-d]pyrimidine-6-carbonitrile
4-(Diethylamino)-5-methyl-2-(4-methylphenyl)thieno[2,3-d]pyrimidine-6-carbonitrile
2-(1,3-Benzodioxol-5-yl)-4-(diethylamino)-5-methylthieno[2,3-d]pyrimidine-6-carbonitrile
2-(1,3-Benzodioxol-5-yl)-5-methyl-4-morpholin-4-ylthieno[2,3-d]pyrimidine-6-carbonitrile
4-[Ethyl(methyl)amino]-5-methyl-2-pyridin-4-ylthieno[2,3-d]pyrimidine-6-carbonitrile
4-[Ethyl(methyl)amino]-5-methyl-2-(3,4,5-trimethoxyphenyl)thieno[2,3-d]pyrimidine-6-carbonitrile
2-Benzyl-5-methyl-4-(4-methylpiperazin-1-yl)thieno[2,3-d]pyrimidine-6-carbonitrile
5-Methyl-4-morpholin-4-yl-2-pyridin-4-ylthieno[2,3-d]pyrimidine-6-carbonitrile
4-[(2-Hydroxyethyl)(methyl)amino]-5-methyl-2-pyridin-4-ylthieno[2,3-d]pyrimidine-6-carbonitrile
2-(1,3-Benzodioxol-5-yl)-4-[(2-hydroxymethyl)(methyl)amino]-5-methylthieno[2,3-d]pyrimidine-6-carbonitrile
4-[(2-Hydroxyethyl)(methyl)amino]-5-methyl-2-(4-methylphenyl)thieno[2,3-d]pyrimidine-6-carbonitrile
4-(Diethylamino)-5-methyl-2-pyridin-4-ylthieno[2,3-d]pyrimidine-6-carbonitrile
2-(3,4-Dimethoxyphenyl)-4-(dimethylamino)-5-methylthieno[2,3-d]pyrimidine-6-carbonitrile
2-(3,4-Dimethoxyphenyl)-5-methyl-4-(propylamino)thieno[2,3-d]pyrimidine-6-carbonitrile
4-(Diethylamino)-5-methyl-2-(3,4,5-trimethoxyphenyl)thieno[2,3-d]pyrimidine-6-carbonitrile
2-Benzyl-4-(diethylamino)-5-methylthieno[2,3-d]pyrimidine-6-carbonitrile
5-Methyl-4-(4-methylpiperazin-1-yl)-2-phenylthieno[2,3-d]pyrimidine-6-carbonitrile
5-Methyl-4-morpholin-4-yl-2-(3,4,5-trimethoxyphenyl)thieno[2,3-d]pyrimidine-6-carbonitrile
4-[(2-Hydroxyethyl)-methylamino]-5-methyl-2-(3,4,5-trimethoxyphenyl)thieno[2,3-d]pyrimidine-6-carbonitrile
2-(3,5-Dimethoxyphenyl)-5-methyl-4-(4-methylpiperazin-1-yl)thieno[2,3-d]pyrimidine-6-carbonitrile
4-Diethylamino-2-(3,5-dimethoxyphenyl)-5-methylthieno[2,3-d]pyrimidine-6-carbonitrile
2-(3,5-Dimethoxyphenyl)-4-(ethylmethylamino)-5-methylthieno[2,3-d]pyrimidine-6-carbonitrile
4-(6-Cyano-4-diethylamino-5-methylthieno[2,3-d]pyrimidin-2-yl)-benzoic acid methyl ester
4-[6-Cyano-4-(ethylmethylamino)-5-methylthieno[2,3-d]pyrimidin-2-yl]-benzoic acid methyl ester
2-Benzyl-5-methyl-4-morpholin-4-ylthieno[2,3-d]pyrimidine-6-carbonitrile
2-Benzyl-4-[(2-hydroxyethyl)methylamino]-5-methylthieno[2,3-d]pyrimidine-6-carbonitrile
5-Methyl-4-(4-methylpiperazin-1-yl)-2-(3,4,5-trimethoxyphenyl)thieno[2,3-d]pyrimidine-6-carbonitrile
Methyl 4-(6-cyano-5-methyl-4-morpholin-4-ylthieno[2,3-d]pyrimidin-2-yl)benzoate
Methyl 4-[6-cyano-5-methyl-4-(4-methylpiperazin-1-yl)thieno[2,3-d]pyrimidin-2-yl]benzoate
Methyl 4-[6-cyano-4-(dimethylamino)-5-methylthieno[2,3-d]pyrimidin-2-yl]benzoate
Methyl 4-{6-cyano-4-[(2-hydroxyethyl)(methyl)amino]-5-methylthieno[2,3-d]pyrimidin-2-yl}benzoate
5-methyl-4-(methylamino)-2-(3,4,5-trimethoxyphenyl)thieno[2,3-d]pyrimidine-6-carbonitrile
4-(Dimethylamino)-5-methyl-2-(3,4,5-trimethoxyphenyl)thieno[2,3-d]pyrimidine-6-carbonitrile
4-(Ethylamino)-5-methyl-2-(3,4,5-trimethoxyphenyl)thieno[2,3-d]pyrimidine-6-carbonitrile
5-Methyl-4-(propylamino)-2-(3,4,5-trimethoxyphenyl)thieno[2,3-d]pyrimidine-6-carbonitrile
4-(Butylamino)-5-methyl-2-(3,4,5-trimethoxyphenyl)thieno[2,3-d]pyrimidine-6-carbonitrile
4-(Isopropylamino)-5-methyl-2-(3,4,5-trimethoxyphenyl)thieno[2,3-d]pyrimidine-6-carbonitrile
4-(sec-Butylamino)-5-methyl-2-(3,4,5-trimethoxyphenyl)thieno[2,3-d]pyrimidine-6-carbonitrile
4-(Isobutylamino)-5-methyl-2-(3,4,5-trimethoxyphenyl)thieno[2,3-d]pyrimidine-6-carbonitrile
4-[(1-Ethylpropyl)amino]-5-methyl-2-(3,4,5-trimethoxyphenyl)thieno[2,3-d]pyrimidine-6-carbonitrile
4-(tert-Butylamino)-5-methyl-2-(3,4,5-trimethoxyphenyl)thieno[2,3-d]pyrimidine-6-carbonitrile
4-(Cyclopropylamino)-5-methyl-2-(3,4,5-trimethoxyphenyl)thieno[2,3-d]pyrimidine-6-carbonitrile
4-(Cyclobutylamino)-5-methyl-2-(3,4,5-trimethoxyphenyl)thieno[2,3-d]pyrimidine-6-carbonitrile 4-(Cyclopentylamino)-5-methyl-2-(3,4,5-trimethoxyphenyl)thieno[2,3-d]pyrimidine-6-carbonitrile
4-[Allyl(methyl)amino]-5-methyl-2-(3,4,5-trimethoxyphenyl)thieno[2,3-d]pyrimidine-6-carbonitrile
5-Methyl-4-[methyl(prop-2-ynyl)amino]-2-(3,4,5-trimethoxyphenyl)thieno[2,3-d]pyrimidine-6-carbonitrile
4-[(2-Hydroxyethyl)amino]-5-methyl-2-(3,4,5-trimethoxyphenyl)thieno[2,3-d]pyrimidine-6-carbonitrile
4-[(2-Methoxyethyl)amino]-5-methyl-2-(3,4,5-trimethoxyphenyl)thieno[2,3-d]pyrimidine-6-carbonitrile
4-{[2-(Dimethylamino)ethyl]amino}-5-methyl-2-(3,4,5-trimethoxyphenyl)thieno[2,3-d]pyrimidine-6-carbonitrile
5-Methyl-4-(3-methylpiperazin-1-yl)-2-(3,4,5-trimethoxyphenyl)thieno[2,3-d]pyrimidine-6-carbonitrile
4-(3,5-Dimethylpiperazin-1-yl)-5-methyl-2-(3,4,5-trimethoxyphenyl)thieno[2,3-d]pyrimidine-6-carbonitrile
4-(4-Acetylpiperazin-1-yl)-5-methyl-2-(3,4,5-trimethoxyphenyl)thieno[2,3-d]pyrimidine-6-carbonitrile
4-[(2-Aminoethyl)(methyl)amino]-5-methyl-2-(3,4,5-trimethoxyphenyl)thieno[2,3-d]pyrimidine-6-carbonitrile
N-[6-Cyano-5-methyl-2-(3,4,5-trimethoxyphenyl)thieno[2,3-d]pyrimidin-4-y]-beta-alanine
5-Methyl-4-(1H-pyrazol-1-yl)-2-(3,4,5-trimethoxyphenyl)thieno[2,3-d]pyrimidine-6-carbonitrile
4-(1H-Imidazol-1-yl)-5-methyl-2-(3,4,5-trimethoxyphenyl)thieno[2,3-d]pyrimidine-6-carbonitrile
5-Methyl-4-(2H-1,2,3-triazol-2-yl)-2-(3,4,5-trimethoxyphenyl)thieno[2,3-d]pyrimidine-6-carbonitrile
5-Methyl-4-(1H-1,2,4-triazol-1-yl)-2-(3,4,5-trimethoxyphenyl)thieno[2,3-d]pyrimidine-6-carbonitrile
2-(3,4-Dimethoxybenzyl)-5-methyl-4-morpholin-4-ylthieno[2,3-d]pyrimidine-6-carbonitrile
2-(3,4-Dimethoxybenzyl)-5-methyl-4-(4-methylpiperazin-1-yl)thieno[2,3-d]pyrimidine-6-carbonitrile
2-(3,4-Dimethoxybenzyl)-5-methyl-4-(methylamino)thieno[2,3d]pyrimidine-6-carbonitrile
2-(3,4-Dimethoxybenzyl)-4-(ethylamino)-5-methylthieno[2,3-d]pyrimidine-6-carbonitrile
2-(3,4-Dimethoxybenzyl)-5-methyl-4-(propylamino)thieno[2,3-d]pyrimidine-6-carbonitrile
4-(Cyclopropylamino)-2-(3,4-dimethoxybenzyl)-5-methylthieno[2,3-d]pyrimidine-6-carbonitrile
4-(Cyclobutylamino)-2-(3,4-dimethoxybenzyl)-5-methylthieno[2,3-d]pyrimidine-6-carbonitrile
2-(3,4-Dimethoxybenzyl)-4-(dimethylamino)-5-methylthieno[2,3-d]pyrimidine-6-carbonitrile
2-(3,4-Dimethoxybenzyl)-4-[ethyl(methyl)amino]-5-methylthieno[2,3-d]pyrimidine-6-carbonitrile
4-(Diethylamino)-2-(3,4-dimethoxybenzyl)-5-methylthieno[2,3-d]pyrimidine-6-carbonitrile
4-[Allyl(methyl)amino]-2-(3,4-dimethoxybenzyl)-5-methylthieno[2,3-d]pyrimidine-6-carbonitrile
2-(3,4-Dimethoxybenzyl)-5-methyl-4-[methyl(prop-2-ynyl)amino]thieno[2,3-d]pyrimidine-6-carbonitrile
2-(3,4-Dimethoxybenzyl)-4-[(2-hydroxyethyl)amino]-5-methylthieno[2,3-d]pyrimidine-6-carbonitrile
2-(3,4-Dimethoxybenzyl)-4-[(2-hydroxyethyl)(methyl)amino]-5-methylthieno[2,3-d]pyrimidine-6-carbonitrile
2-(3,4-Dimethoxybenzyl)-4-[(2-methoxyethyl)amino]-5-methylthieno[2,3-d]pyrimidine-6-carbonitrile
4-[[2-(Dimethylamino)ethyl](methyl)amino]-5-methyl-2-(3,4,5-trimethoxyphenyl)thieno[2,3-d]pyrimidine-6-carbonitrile
5-Methyl-4-morpholin-4-yl-2-(3,4,5-trimethoxybenzyl)thieno[2,3-d]pyrimidine-6-carbonitrile
5-Methyl-4-(4-methylpiperazin-1-yl)-2-(3,4,5-trimethoxybenzyl)thieno[2,3-d]pyrimidine-6-carbonitrile
5-Methyl-4-(methylamino)-2-(3,4,5-trimethoxybenzyl)thieno[2,3-d]pyrimidine-6-carbonitrile
4-(Ethylamino)-5-methyl-2-(3,4,5-trimethoxybenzyl)thieno[2,3-d]pyrimidine-6-carbonitrile
5-Methyl-4-(propylamino)-2-(3,4,5-trimethoxybenzyl)thieno[2,3-d]pyrimidine-6-carbonitrile
4-(Isopropylamino)-5-methyl-2-(3,4,5-trimethoxybenzyl)thieno[2,3-d]pyrimidine-6-carbonitrile
4-(sec-Butylamino)-5-methyl-2-(3,4,5-trimethoxybenzyl)thieno[2,3-d]pyrimidine-6-carbonitrile
4-[(1-Ethylpropyl)amino]-5-methyl-2-(3,4,5-trimethoxybenzyl)thieno[2,3-d]pyrimidine-6-carbonitrile
4-(tert-Butylamino)-5-methyl-2-(3,4,5-trimethoxybenzyl)thieno[2,3-d]pyrimidine-6-carbonitrile
4-(Cyclopropylamino)-5-methyl-2-(3,4,5-trimethoxybenzyl)thieno[2,3-d]pyrimidine-6-carbonitrile
4-(Cyclobutylamino)-5-methyl-2-(3,4,5-trimethoxybenzyl)thieno[2,3-d]pyrimidine-6-carbonitrile
4-(Dimethylamino)-5-methyl-2-(3,4,5-trimethoxybenzyl)thieno[2,3-d]pyrimidine-6-carbonitrile
4-[Ethyl(methyl)amino]-5-methyl-2-(3,4,5-trimethoxybenzyl)thieno[2,3-d]pyrimidine-6-carbonitrile
4-(Diethylamino)-5-methyl-2-(3,4,5-trimethoxybenzyl)thieno[2,3-d]pyrimidine-6-carbonitrile
4-[Allyl(methyl)amino]-5-methyl-2-(3,4,5-trimethoxybenzyl)thieno[2,3-d]pyrimidine-6-carbonitrile
5-Methyl-4-[methyl(prop-2-ynyl)amino]-2-(3,4,5-trimethoxybenzyl)thieno[2,3-d]pyrimidine-6-carbonitrile
4-[(2-Hydroxyethyl)amino]-5-methyl-2-(3,4,5-trimethoxybenzyl)thieno[2,3d]pyrimidine-6-carbonitrile
4-[(2-Methoxyethyl)amino]-5-methyl-2-(3,4,5-trimethoxybenzyl)thieno[2,3-d]pyrimidine-6-carbonitrile
4[(2-Hydroxyethyl)(methyl)amino]-5-methyl-2-(3,4,5-trimethoxybenzyl)thieno[2,3-d]pyrimidine-6-carbonitrile
5-methyl-4-(4-methylpiperazin-1-yl)-2-(2-phenylethyl)thieno[2,3-d]pyrimidine-6-carbonitrile
4-(Cyclobutylamino)-5-methyl-2-(2-phenylethyl)thieno[2,3-d]pyrimidine-6-carbonitrile
4-(Diethylamino)-5-methyl-2-(2-phenylethyl)thieno[2,3-d]pyrimidine-6-carbonitrile
5-Methyl-4-(4-methylpiperazin-1-yl)-2-(3-phenylpropyl)thieno[2,3-d]pyrimidine-6-carbonitrile
4-(Diethylamino)-5-methyl-2-(3-phenylpropyl)thieno[2,3-d]pyrimidine-6-carbonitrile
2-(3,5-Dimethoxy-phenyl)-4-[(2-hydroxy-ethyl)-methylamino]-5-methyl-thieno[2,3-d]pyrimidine-6-carbonitrile
2-(3,5-Dimethoxy-phenyl)-5-methyl-4-morpholin-4-ylthieno[2,3-d]pyrimidine-6-carbonitrile
2-(3,5-Dimethoxyphenyl)-4-(ethylamino)-5-methylthieno[2,3-d]pyrimidine-6-carbonitrile 4-(Isobutylamino)-5-methyl-2-(3,4,5-trimethoxybenzyl)thieno[2,3-d]pyrimidine-6-carbonitrile and pharmaceutically acceptable salts thereof.

According to one embodiment of the present invention in the compounds of formula (I) $R_1$ and $R_2$ either:

(a) independently represent hydrogen or groups selected from alkyl, alkenyl or alkynyl groups having from 1 to 4 carbon atoms which are optionally substituted by one hydroxy group or cycloalkyl group having from 3 to 6 carbon atoms;

or (b) (b) $R_1$ and $R_2$ form, together with the nitrogen atom to which they are attached, a 4- to 6-membered ring comprising from 1 to 2 heteroatoms selected from nitrogen, oxygen and sulphur, which ring is optionally substituted by one or two $C_1$-$C_4$ alkyl groups which are themselves unsubstituted or substituted by one hydroxy group.

Preferably, $R_1$ and $R_2$ either:

(a) independently represent groups selected from an alkyl, alkenyl or alkynyl groups having from 1 to 4 carbon atoms which are optionally substituted by one hydroxy group or cycloalkyl group having from 3 to 6 carbon atoms; or (b) $R_1$ and $R_2$ form, together with the nitrogen atom to which they are attached, a 4- to 6-membered ring comprising from 1 to 2 heteroatoms selected from nitrogen, oxygen and sulphur, which ring is optionally substituted by one or two $C_1$-$C_4$ alkyl groups which are themselves unsubstituted or substituted by one hydroxy group.

Most preferably $R_1$ either a) represents a hydrogen atom or an alkyl group having from 1 to 4 carbon atoms or b) forms together with $R^2$ and with the nitrogen atom to which they are attached, a 4- to 6-membered ring comprising from 1 to 2 heteroatoms selected from nitrogen and oxygen, which ring is optionally substituted by one or more substituents selected from halogen atoms and alkyl or acyl groups;

Also preferably $R_2$ either a) represents a group selected from an alkyl, alkenyl, alkynyl, cycloalkyl, hydroxyalkyl or di-alkylamino groups or b) forms together with $R_1$ and with the nitrogen atom to which they are attached, a 4- to 6-membered ring comprising from 1 to 2 heteroatoms selected from nitrogen and oxygen, which ring is optionally substituted by one or more substituents selected from halogen atoms and alkyl or acyl groups;

In another embodiment of the present invention $R_3$ represents a group of formula —(CH$_2$)$_n$-G wherein n is an integer from 0 to 4 and G represents a monocyclic aryl or heteroaryl group comprising zero or one heteroatoms, which aryl or heteroaryl group is optionally substituted by one or more, for example 1, 2, 3 or 4, substituents selected from:
(i) halogen atoms;
(ii) unsubstituted $C_1$-$C_8$ alkyl, unsubstituted $C_1$-$C_8$ alkoxy, unsubstituted $C_1$-$C_3$ alkylenedioxy, nitro, trifluoromethyl and unsubstituted alkoxycarbonyl groups having a $C_1$-$C_8$ alkyl portion.

More preferably $R_3$ represents a group selected from phenyl, pyridyl or benzyl groups which groups are optionally substituted by one or more, for example 1, 2, 3 or 4, substituents selected from:
(i) halogen atoms;
(ii) unsubstituted $C_1$-$C_8$ alkyl, unsubstituted $C_1$-$C_8$ alkoxy, unsubstituted $C_1$-$C_3$ alkylenedioxy, nitro, trifluoromethyl and unsubstituted $C_1$-$C_8$ alkoxycarbonyl groups.

In still another embodiment of the present invention $R_4$ is hydrogen, an unsubstituted $C_1$-$C_8$ alkyl or unsubstituted $C_5$-$C_{14}$ aryl group. Typically, $R_4$ represents an unsubstituted $C_1$-$C_4$ alkyl group. Preferably, $R_4$ represents a —CH$_3$ group.

Most preferred compounds of the invention are compounds of formula (I):

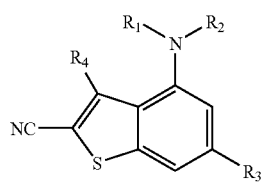

(I)

or pharmaceutically acceptable salts thereof wherein
$R_1$ and $R_2$ either:
(a) independently represent hydrogen or groups selected from alkyl, alkenyl or alkynyl groups having from 1 to 4 carbon atoms which are optionally substituted by one hydroxy group;

or
(b) $R_1$ and $R_2$ form, together with the nitrogen atom to which they are attached, a 4- to 6-membered ring comprising from 1 to 2 heteroatoms selected from nitrogen, oxygen and sulphur, which ring is optionally substituted by one or two $C_1$-$C_4$ alkyl groups which are themselves unsubstituted or substituted by one hydroxy group;

$R_3$ represents a group selected from phenyl, pyridyl or benzyl groups which groups are optionally substituted by one or more, for example 1, 2, 3 or 4, substituents selected from:
(i) halogen atoms;
(ii) unsubstituted $C_1$-$C_8$ alkyl), unsubstituted $C_1$-$C_8$ alkoxy, unsubstituted $C_1$-$C_3$ alkylenedioxy, nitro, trifluoromethyl and unsubstituted $C_1$-$C_8$ alkoxycarbonyl groups; and $R_4$ represents an unsubstituted $C_{1-4}$ alkyl group.

In another embodiment of the present invention $R_3$ represents a phenyl or benzyl group substituted by one, two or three $C_{1-6}$ alkoxy groups.

In a still more preferred embodiment of the present invention $R_1$ represents a hydrogen atom, $R_2$ represents
(i) a group selected from an alkyl, alkenyl or alkynyl groups, which are optionally substituted by one or more substituents selected from halogen atoms and hydroxy, alkoxy, aryloxy, alkylthio, hydroxycarbonyl, alkoxycarbonyl, mono- or di-alkylaminoacyl, oxo, amino, mono- or di-alkylamino groups; or
(ii) a group of formula —(CH$_2$)$_n$—R$^6$ wherein n is an integer from 0 to 4 and $R^6$ represents a cycloalkyl or cycloalkenyl group;

and $R_3$ represents a phenyl or benzyl group substituted by one, two or three $C_{1-6}$ alkoxy groups.

In another aspect the present invention encompasses a synthetic process for the preparation of the compounds of formula (I) which is depicted in Scheme 3 and comprises the steps of (a) reacting the thienopyrimidinone of formula (VI) under reflux with a chlorinating agent, (b) removing after cooling the excess of chlorinating agent, (c) optionally isolating the chlorothienopyrimidine of formula (VII) and (d) reacting the chlorothienopyrimidine of formula (VII) with an amine (VIII) in a closed atmosphere at temperatures ranging from 40° C. to 120° C.

The compounds of the present invention may be prepared by one of the processes described below:

SCHEME 1

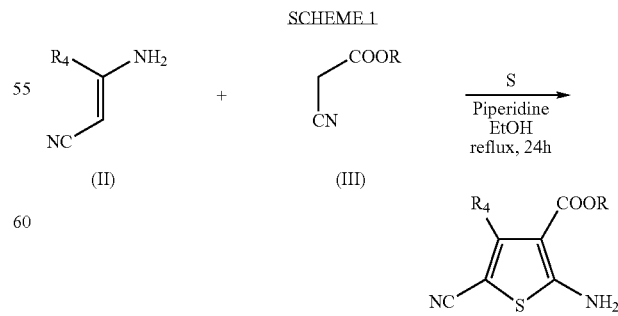

Following the teachings of GB 1 454 529 a cyano acetic acid ethyl ester (III), elemental sulphur and a catalytic amount of piperidine are added to a solution of a 3-amino α,β-unsaturated nitrile (II) in ethanol. The mixture is heated to 50-60° C. until the reaction starts, which is evidenced by an increase of the temperature of the mixture up to the region of 90-100° C. After the temperature begins to decrease, the mixture is refluxed for an additional 24 hours. The solid formed after cooling a 4-substituted 2-amino-5-cyano-thiophene-3-carboxylic acid alkyl ester (IV)] is collected by filtration, and recrystallized from ethanol.

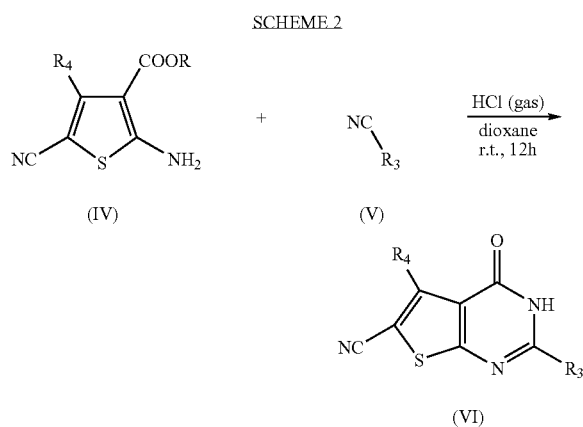

A stream of dry hydrogen chloride is passed for 2 hours through a mixture of the 4-substituted-2-amino-5-cyano-thiophene-3-carboxylic acid alkyl ester (IV) and the corresponding nitrile (V) in dioxane. The reaction is stirred at room temperature for 12 hours, the solvent is removed under reduced pressure and the residue is triturated with diethyl ether. The precipitate obtained is filtered, dried and the corresponding thienopyrimidinone (VI) is used in the next reaction step without further purification.

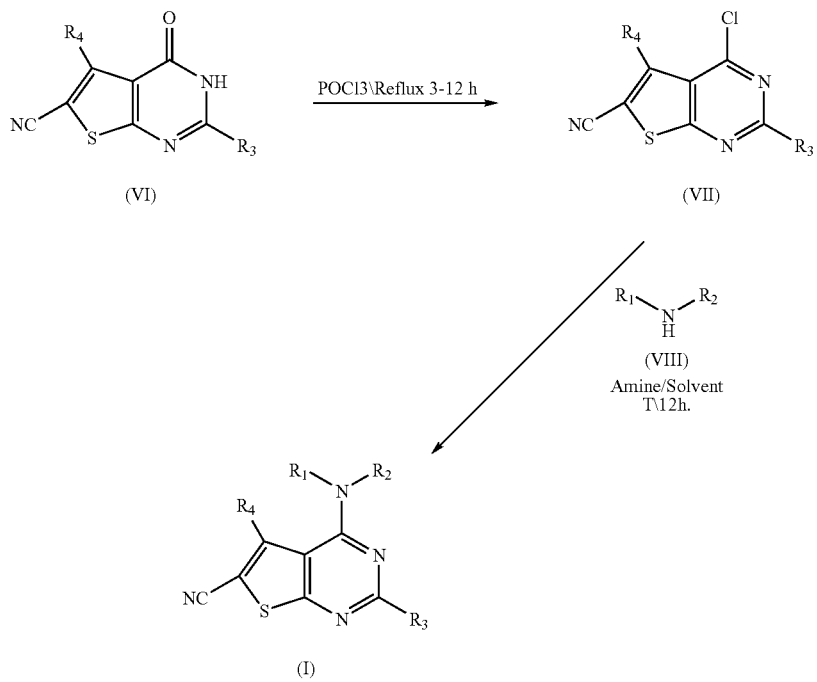

A solution of the corresponding thienopyrimidinone (VI) in phosphorous oxychloride is refluxed for 3-12 h. After cooling, POCl₃ is removed under reduced pressure, the residue is dissolved in dichloromethane, and the organic layer is washed with a saturated aqueous solution of NaHCO₃, water, then brine. The organic layer is dried over MgSO₄, filtered and evaporated to yield the corresponding crude of 4-chlorothieno[2,3-d]pyrimidine (VII), which is used in the next reaction step without further purification.

An amine (VIII) is added to a solution of the 4-chlorothieno[2,3-d]pyrimidine (VII) in either ethanol or a mixture of acetonitrile and a base (for example an alkaline carbonate or diisopropylethylamine) in a closable bottle. The bottle is closed with a polypropylene cap, and heated overnight in a conventional oven at a temperature comprised between 40° and 120° C., preferably between 60 and 85° C. After cooling, the solvent is removed under reduced pressure, and the residue is purified by flash chromatography to provide the final thieno[2,3-d]pyrimidin-4-ylamine (I).

Pharmacological Activity

PDE7 Assay Procedure

All compounds are resuspended in DMSO at a stock concentration of 10 mM. The compounds are tested at concentrations ranging from 1 mM to 1 nM in order to calculate an $IC_{50}$. All dilutions are performed in 96 well plates.

For each reaction, 10 microliters of the diluted compounds are poured into "low binding" assay plates. 80 microliters of a reaction mixture containing 50 mM Tris pH 7.5, 8.3 mM $MgCl_2$, 1.7 mM EGTA, and 15 nM 3',5'[3H]-cAMP (around 150000 dpm) are added to each well. The reaction is initiated by adding 10 microliters of a solution containing PDE7 to the reaction mixture. The plate is then incubated under stirring for 1 hour at room temperature. After incubation the reaction is stopped with 50 microlitres (0.89 mg) of PDE SPA beads (Amersham Pharmacia Biotech RPNQ0150), and the resulting mixture is allowed to settle for 20 minutes before counting in a microtitre plate counter.

Using the assay described above the $IC_{50}$ of all compounds in the examples was determined to be smaller than 10 micromolar and the compounds of Examples 2-7 9-11, 13-17, 20-22, 24-27, 31, 33-39, 41-49, 51-57, 60-62, 64-85, 87-93, 95-109, 111-126, 128-129, 131-135 showed and $IC_{50}$ smaller than 1 micromolar.

The results of PDE7 inhibition show that the compounds of formula (I) are potent inhibitors of phosphodiesterase 7 (PDE7) and are therefore useful in the treatment or prevention of pathological conditions, diseases and disorders susceptible of amelioration by inhibition of PDE7, such as asthma, atopic dermatitis, chronic obstructive pulmonary disease, Crohn's disease, type I and type II diabetes, lymphoid leukemia and other forms of cancer, multiple sclerosis, alograft rejection after organ transplantation, psoriasis, rheumatoid arthritis and ulcerative colitis.

Some of the compounds of the present invention are not only potent PDE7 inhibitors but are also selective over other cAMP specific phosphodiesterases such as PDE3 or PDE4. Compounds which show a particularly good selectivity are those where the $R_3$ group is selected from phenyl or benzyl groups substituted by one, two or three $C_{1-6}$ alkoxy groups.

The compounds of the present invention can also be used in combination with other drugs known to be effective in the treatment of these diseases. For example, they can be used in combination with one or more compounds selected from PDE4 inhibitors, $A_{2A}$ adenosine receptor antagonists, NSAIDs, COX-2 inhibitors, TNF-α inhibitors and steroids.

Accordingly, another embodiment of the invention is the use of the compounds of formula (I) in the manufacture of a medicament for treatment or prevention of pathological conditions, diseases and disorders susceptible of amelioration by inhibition of PDE7, as well as a method for treating a subject afflicted with a pathological condition or disease susceptible to amelioration by inhibition of PDE7, which comprises administering to said subject an effective amount of a compound of formula (I).

The present invention also provides pharmaceutical compositions which comprise, as an active ingredient, at least a compound of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent and a flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The present invention will be further illustrated by the following examples. The examples are given by way of illustration only and are not to be construed as a limiting.

$^1$H NMR spectra were recorded either at 200 or 300 MHz and $^{13}$C NMR spectra were recorded at 75 MHz, using a Varian Unity 300 instrument. Chemical shifts are reported as δ values (ppm). The low-resolution mass spectra (MS) were obtained in a HPLC-MS Agilent 1100-MSD-20, as CI (CH$_4$). Melting points were recorded uncorrected using a Perkin Elmer DSC-7 apparatus. Infrared spectra were recorded in a Perkin-Elmer IR-FT Spectrum 2000 spectrophotometer, either on KBr pellets or on a CHCl$_3$ film and spectral bands are reported in cm$^{-1}$. Elemental Analysis was performed on a Heraeus CHN—O rapid instrument.

PREPARATION EXAMPLES

Preparation 1

2-Amino-5-cyano-4-methylthiophene-3-carboxylic acid ethyl ester

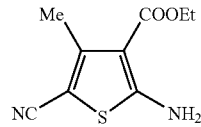

To a solution of 3-aminocrotonitrile (0.01 mol) in 30 ml of ethanol, elemental sulphur (0.01 mol), cyanoacetic acid ethyl ester (0.01 mol) and a catalytic amount of piperidine were added. The mixture was initially heated to 50-60° C. until the reaction commenced when the temperature of the mixture was increased to 90-100° C. When the reaction temperature began to fall, the mixture was refluxed for 24 hours. The solid formed after cooling was collected by filtration, and recrystallized from ethanol to yield the title compound (65% yield) as a brown solid.

m.p. 200-202° C.; $^1$H-NMR (CDCl$_3$, 300 MHz) δ 6.60 (bs, 2H), 4.32 (q, J=7.1 Hz, 2H), 2.49 (s, 3H), 1.38 (t, J=7.1 Hz, 3H).

Preparation 2

5-Methyl-4-oxo-2-phenyl-3,4-dihydrothieno[2,3-d]pyrimidine-6-carbonitrile

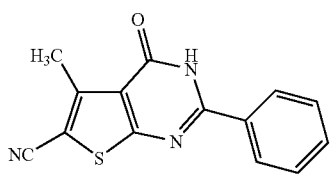

A stream of dry hydrogen chloride was passed through a mixture of 2-amino-5-cyano-4-methylthiophene-3-carboxylic acid ethyl ester (0.003 mol) and benzonitrile (0.0045 mol) in 20 ml. of dioxane for 2 hours. Then, the reaction was stirred at room temperature for 12 hours, subsequently, the solvent was removed under reduced pressure and the residue was triturated with diethyl ether. A precipitate was obtained, filtered and dried to yield (92% yield) the title compound as a brown solid.

$^1$H-NMR (DMSO-$d_6$, 300 MHz) δ 13.02 (bs, 1H), 8.21 (d, J=6.6 Hz, 2H), 7.66-7.61 (m, 3H), 2.73 (s, 3H); IR (KBr) 3415, 2219, 1663, 1539, 700 cm$^{-1}$; MS (API-ES−, m/z) 266.0 (M−1).

Preparation 3

5-Methyl-2-(4-nitrophenyl)-4-oxo-3,4-dihydrothieno[2,3-d]pyrimidine-6-carbonitrile

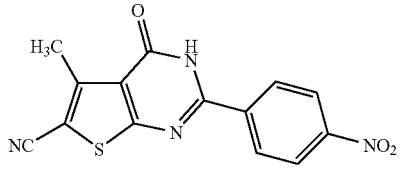

Obtained as a brown solid (47%) from 2-amino-5-cyano-4-methylthiophene-3-carboxylic acid ethyl ester and 4-nitrobenzonitrile following the experimental procedure described in preparation 2.

$^1$H-NMR (DMSO-$d_6$, 300 MHz) δ 13.26 (bs, 1H), 8.29 (d, J=8.6 Hz, 2H), 8.08 (d, J=8.6 Hz, 2H), 2.69 (s, 3H); MS (API-ES−, m/z) 311.0 (M−1).

Preparation 4

2-(4-Methoxyphenyl)-5-methyl-4-oxo-3,4-dihydrothieno[2,3-d]pyrimidine-6-carbonitrile

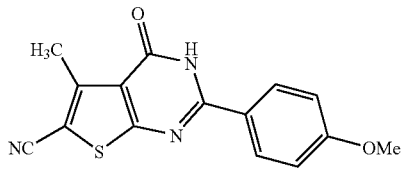

Obtained as a brown solid (99%) from 2-amino-5-cyano-4-methylthiophene-3-carboxylic acid ethyl ester and 4-methoxybenzonitrile following the experimental procedure described in preparation 2.

$^1$H-NMR (CDCl$_3$, 300 MHz) δ 10.21 (bs, 1H), 7.84 (d, J=8.4 Hz, 2H), 6.91 (d, J=8.4 Hz, 2H), 3.88 (s, 3H), 2.56 (t, 3H).

Preparation 5

5-Methyl-2-(4-methylphenyl)-4-oxo-3,4-dihydrothieno[2,3-d]pyrimidine-6-carbonitrile

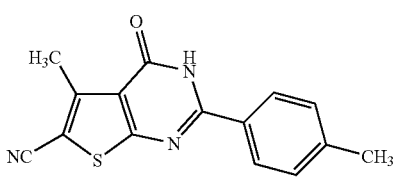

Obtained as a brown solid (72%) from 2-amino-5-cyano-4-methylthiophene-3-carboxylic acid ethyl ester and 4-methylbenzonitrile following the experimental procedure described in preparation 2.

$^1$H-NMR (CDCl$_3$, 200 MHz) δ 10.30 (bs, 1H), 7.97 (d, J=7.7 Hz, 2H), 7.29 (d, J=7.7 Hz, 2H), 2.78 (s, 3H), 2.45 (s, 3H).

Preparation 6

5-Methyl-4-oxo-2-[4-(trifluoromethyl)phenyl]-3,4-dihydrothieno[2,3-d]pyrimidine-6-carbonitrile

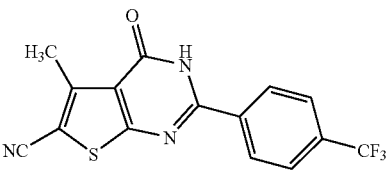

Obtained as a brown solid (81%) from 2-amino-5-cyano-4-methylthiophene-3-carboxylic acid ethyl ester and 4-trifluoromethylbenzonitrile following the experimental procedure described in preparation 2.

$^1$H-NMR (CDCl$_3$, 300 MHz) δ 13.00 (bs, 1H), 8.12 (d, J=8.0 Hz, 2H), 7.65 (d, J=8.0 Hz, 2H), 2.56 (t, 3H).

Preparation 7

2-(4-Chlorophenyl)-5-methyl-4-oxo-3,4-dihydrothieno[2,3-d]pyrimidine-6-carbonitrile

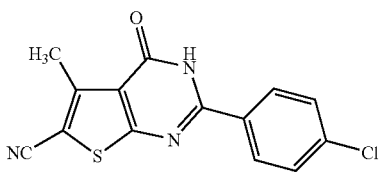

Obtained as a brown solid (84%) from 2-amino-5-cyano-4-methylthiophene-3-carboxylic acid ethyl ester and 4-chlorobenzonitrile following the experimental procedure described in preparation 2.

$^1$H-NMR (CDCl$_3$, 200 MHz) δ 13.16 (bs, 1H), 7.73 (d, J=8.7 Hz, 2H), 7.41 (d, J=8.7 Hz, 2H), 2.78 (s, 3H).

Preparation 8

2-(3,4-Dimethoxyphenyl)-5-methyl-4-oxo-3,4-dihydrothieno[2,3-d]pyrimidine-6-carbonitrile

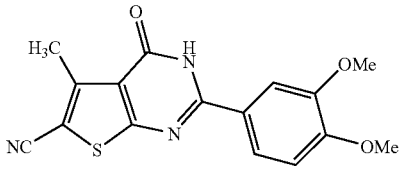

Obtained as a brown solid (99%) from 2-amino-5-cyano-4-methylthiophene-3-carboxylic acid ethyl ester and 3,4-dimethoxybenzonitrile following the experimental procedure described in preparation 2.

$^1$H-NMR (DMSO-d$_6$, 300 MHz) δ 12.62 (bs, 1H), 8.09 (d, J=8.4 Hz, 1H), 8.04 (s, 1H), 6.94 (d, J=8.4 Hz, 1H), 2.56 (s, 3H).

Preparation 9

2-(1,3-Benzodioxol-5-yl)-5-methyl-4-oxo-3,4-dihydrothieno[2,3-d]pyrimidine-6-carbonitrile

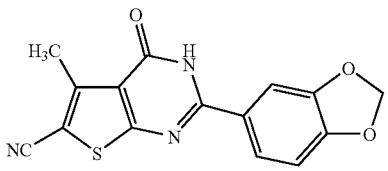

Obtained as a brown solid (22%) from 2-amino-5-cyano-4-methylthiophene-3-carboxylic acid ethyl ester and 1,3-benzodioxole-5-carbonitrile following the experimental procedure described in preparation 2.

$^1$H-NMR (CDCl$_3$, 300 MHz) δ 13.0 (bs, 1H), 7.79 (d, J=7.5 Hz, 1H), 7.7 (s, 1H), 7.08 (d, J=7.5 Hz, 1H), 6.15 (s, 2H), 2.65 (s, 3H).

Preparation 10

5-Methyl-4-oxo-2-pyridin-4-yl-3,4-dihydrothieno[2,3-d]pyrimidine-6-carbonitrile

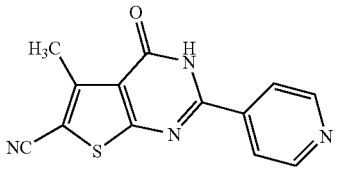

Obtained as a brown solid (63%) from 2-amino-5-cyano-4-methylthiophene-3-carboxylic acid ethyl ester and isonicotinonitrile following the experimental procedure described in preparation 2.

$^1$H-NMR (DMSO-d$_6$, 300 MHz) δ 13.14 (bs, 1H), 8.77 (bs, 2H), 8.05 (bs, 2H), 2.67 (s, 3H).

Preparation 11

2-Benzyl-5-methyl-4-oxo-3,4-dihydrothieno[2,3-d]pyrimidine-6-carbonitrile

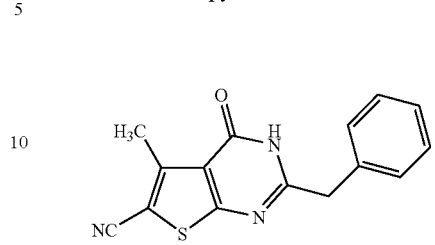

Obtained as a brown solid (65%) from 2-amino-5-cyano-4-methylthiophene-3-carboxylic acid ethyl ester and phenylacetonitrile following the experimental procedure described in preparation 2.

$^1$H-NMR (CDCl$_3$, 300 MHz) δ 10.80 (bs, 1H), 7.34-7.28 (s, 5H), 4.06 (s, 2H), 2.71 (s, 3H).

Preparation 12

5-Methyl-4-oxo-2-(4-benzoic acid methyl ester)-3,4-dihydrothieno[2,3-]pyrimidine-6-carbonitrile

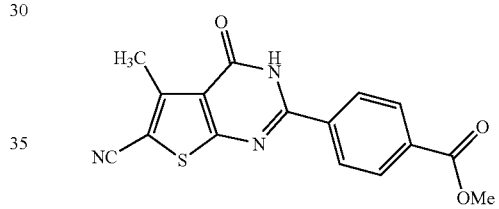

Obtained as a brown solid (85%) from 2-amino-5-cyano-4-methylthiophene-3-carboxylic acid ethyl ester and methyl 4-cyanobenzoate following the experimental procedure described in preparation 2.

m.p.>250° C.; $^1$H-NMR (DMSO-d6, 300 MHz) δ 12.90 (bs, 1H), 8.51 (d, J=8.35 Hz, 2H), 8.10 (d, J=8.35 Hz, 2H), 3.94 (s, 3H), 2.81 (s, 3H).

Preparation 13

5-Methyl-4-oxo-2-(3,4,5-trimethoxyphonyl)-3,4-dihydrothieno[2,3-d]pyrimidine-6-carbonitrile

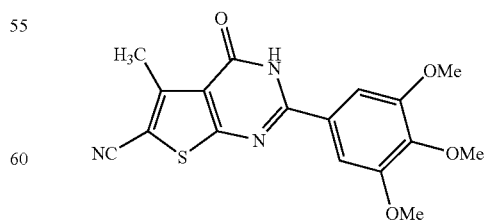

Obtained as a brown solid (63%) from 2-amino-5-cyano-4-methylthiophene-3-carboxylic acid ethyl ester and 3,4,5-trimethoxybenzonitrile following the experimental procedure described in preparation 2.

m.p.>250° C.; ¹H-NMR (DMSO-d6, 300 MHz) δ 12.96 (bs, 1H), 7.73 (s, 2H), 3.90 (s, 6H), 3.87 (s, 3H), 2.81 (s, 3H).

Preparation 14

2-(3,4-Dimetoxi-bencil)-5-metil-4-oxo-3,4-dihidro-tieno[2,3-d]pirimidin-6-carbonitrilo

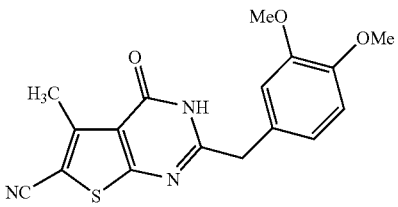

Obtained as a brown solid (47%) from 2-amino-5-cyano-4-methylthiophene-3-carboxylic acid ethyl ester and 3,4-dimethoxyphenylacetonitrile following the experimental procedure described in preparation 2.

m.p.:>250° C.; ¹H-NMR (DMSO-d6, 300 MHz): δ (ppm) 12.40 (bs, 1H), 6.95-6.89 (m, 2H), 6.77-6.73 (m, 1H), 4.5 (s, 2H), 3.83 (s, 3H), 3.79 (s, 3H), 2.66 (s, 3H).

Preparation 15

5-Metil-4-oxo-2-(3,4,6-trimetoxibencil)-3,4-dihidro-tieno[2,3-d]pirimidin-6-carbonitrilo

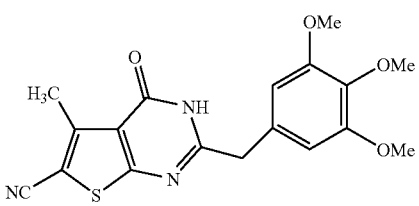

Obtained as a brown solid (69%) from 2-amino-5-cyano-4-methylthiophene-3-carboxylic acid ethyl ester and 3,4,5-trimethoxyphenylacetonitrile following the experimental procedure described in preparation 2.

m.p.:>250° C.; ¹H-NMR (CDCl₃, 300 MHz): δ (ppm) 10.80 (s, 1H), 6.27 (s, 2H), 4.23 (s, 2H), 3.83 (s, 6H), 3.82 (s, 3H), 2.85 (s, 3H).

Preparation 16

5-Metil-4-oxo-2-(feniletil)-3,4-dihidrotieno[2,3-d]pirimidin-6-carbonitrilo

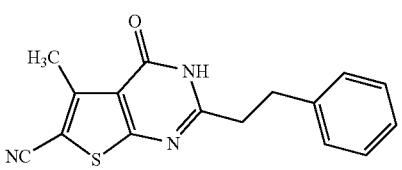

Obtained as a brown solid (69%) from 2-amino-5-cyano-4-methylthiophene-3-carboxylic acid ethyl ester and 3-phenylpropanenitrile following the experimental procedure described in preparation 2.

m.p.:>250° C.; ¹H-NMR (CDCl₃, 300 MHz): δ (ppm) 7.37-7.22 (m, 5H), 3.16-2.93 (m, 4H), 22.62 (s, 3H).

Preparation 17

5-Metil-4-oxo-2-(fenilpropil)-3,4-dihidrotieno[2,3-d]pirimidin-6-carbonitrilo

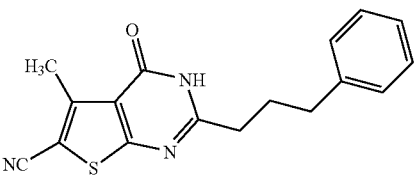

Obtained as a brown solid (94%) from 2-amino-5-cyano-4-methylthiophene-3-carboxylic acid ethyl ester and 4-phenylbutanenitrile following the experimental procedure described in preparation 2.

m.p.:>250° C.; ¹H-NMR (CDCl₃, 300 MHz): δ (ppm) 11.6 (s, 1H), 7.28-7.14 (m, 5H), 3.06 (t, J=7.2 Hz, 2H), 2.85 (s, 3H), 2.72 (t, J=7.2 Hz, 2H), 2.27-2.15 (m, 2H).

EXAMPLES

Following the synthetic method described under scheme 3 a solution of the corresponding thienopyrimidinone (VI) (0.18 mmol) in phosphorous oxychloride (7 ml) was refluxed for 3-12 h. After cooling, POCl₃ was removed under reduced pressure, the residue was dissolved in dichloromethane (20 ml), and the organic layer was washed with a saturated aqueous solution of NaHCO₃, water and brine. Then, the organic layer was dried over MgSO₄, filtered and evaporated to yield the corresponding crude 4-chlorothieno[2,3-d]pyrimidine (VII), which was used in the next reaction step without further purification.

The corresponding amine (VIII) (1.3 eq.) was added to a solution of 0.27 mmol of the 4-chlorothieno[2,3-d]pyrimidine (VII) in 25 ml of ethanol in a closable bottle. The bottle was closed with a polypropylene cap, and heated in a conventional oven at 75° C. over-night. After cooling, the solvent was removed under reduced pressure, and the residue was purified by flash chromatography to provide the final thieno[2,3-d]pyrimidin-4-ylamine (I).

Example 1

4-(4-Ethylpiperazin-1-yl)-5-methyl-2-phenylthieno[2,3-d]pyrimidine-6-carbonitrile

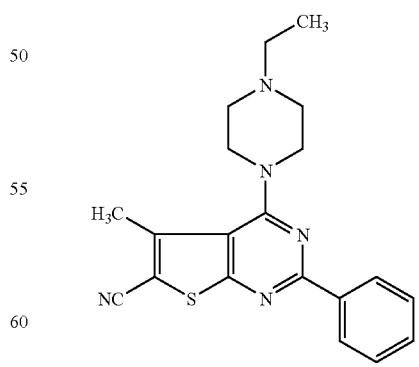

m.p. 178-179° C.; ¹H-NMR (CDCl₃, 300 MHz) δ 8.49-8.45 (m, 2H), 7.50-7.47 (m, 3H), 3.66 (t, 4H, J=4.4 Hz), 2.73 (s, 3H), 2.65 (t, 4H, J=4.4 Hz), 2.49 (q, 2H, J=7.1 Hz), 1.14 (t, 3H, J=7.1 Hz); IR (KBr) 2969, 2212, 1533, 1491, 1446, 1261 cm⁻¹; MS (API-ES+, m/z) 364 (M+1)⁺. Anal. Calcd. for $C_{20}H_{21}N_5S$ (363.480): C, 66.09; H, 5.82; N, 19.27. Found: C, 65.36; H, 6.86; N, 19.05. Yield=52%.

Example 2

4-(4-Ethylpiperazin-1-yl)-2-(4-methoxyphenyl)-5-methylthieno[2,3-d]pyrimidine-6-carbonitrile

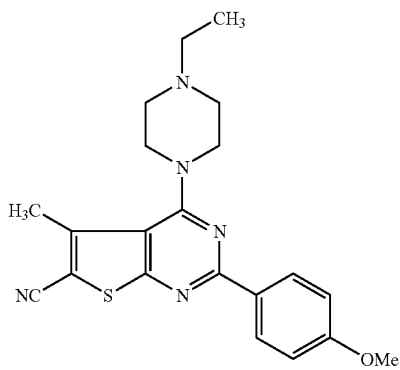

m.p.: 173-175° C.; $^1$H-NMR (CDCl$_3$, 200 MHz) δ 8.43 (d, 2H, J=8.7 Hz), 6.99 (d, 2H, J=8.7 Hz), 3.89 (s, 3H), 3.65 (t, 4H, J=4.6 Hz), 2.72 (s, 3H), 2.65 (t, 4H, J=4.6 Hz), 2.50 (q, 2H, J=7.1 Hz), 1.15 (t, 3H, J=7.1 Hz); IR (KBr) 2812, 2211, 1533, 1252, 1165 cm$^{-1}$; MS (API-ES+, m/z) 394 (M+1)$^+$. Anal. Calcd. for $C_{21}H_{23}N_5OS$ (393.506): C, 64.10; H, 5.89; N, 17.80. Found: C, 63.80; H, 5.94; N, 17.37. Yield=24%.

Example 3

4-(Diethylamino)-5-methyl-2-phenylthieno[2,3-d]pyrimidine-6-carbonitrile

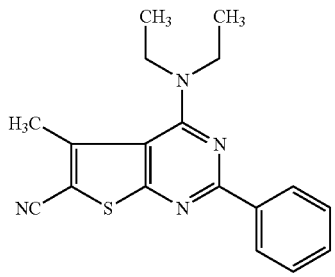

$^1$H-NMR (CDCl$_3$, 300 MHz) δ 8.43-8.46 (m, 2H); 7.45-7.47 (m, 3H), 3.60 (q, J=7.1 Hz, 4H), 2.70 (s, 3H), 1.23 (t, J=7.1 Hz, 6H); MS (API-ES+, m/z) 323 (M+1)$^+$. $C_{18}H_{18}N_4S$ (322.428), Yield=52%.

Example 4

5-Methyl-2-phenyl-4-piperidin-1-ylthieno[2,3-d]pyrimidine-6-carbonitrile

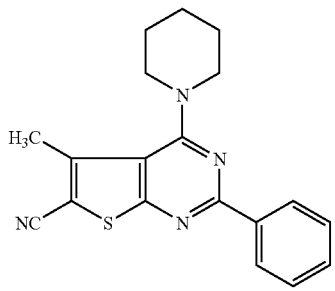

m.p. 142-144° C.; $^1$H-NMR (CDCl$_3$, 300 MHz) δ 8.45-8.48 (m, 2H), 7.45.7.47 (m, 3H), 3.52-4.55 (m, 4H), 2.71 (s, 3H), 1.74-1.77 (m, 6H). $C_{19}H_{18}N_4S$ (334.439), Yield=36%.

Example 5

5-Methyl-2-(4-nitrophenyl)-4-piperidin-1-ylthieno[2,3-d]pyrimidine-6-carbonitrile

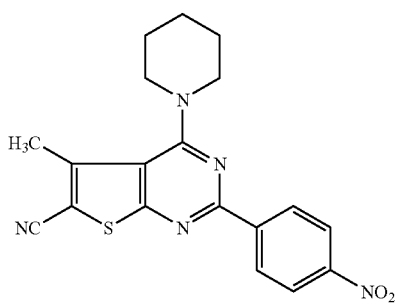

$^1$H-NMR (CDCl$_3$, 300 MHz) δ 8.62 (d, J=8.6 Hz, 2H), 8.29 (d, J=8.6 Hz, 2H), 3.57 (bs, 4H), 2.72 (s, 3H), 1.76 (bs, 6H). $C_{19}H_{17}N_5O_2S$ (379.437), Yield=20%.

Example 6

2-(4-Methoxyphenyl)-5-methyl-4-piperidin-1-ylthieno[2,3-d]pyrimidine-6-carbonitrile

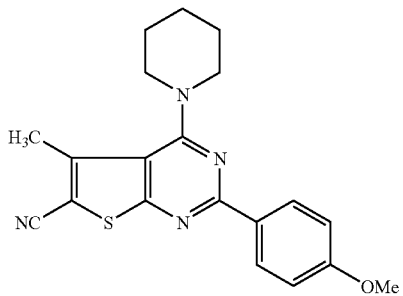

m.P. 202-204° C.; $^1$H-NMR (CDCl$_3$, 300 MHz), δ 8.42 (d, J=8.6 Hz, 2H), 6.97 (d, J=8.6 Hz, 2H), 3.87 (bs, 3H), 3.51 (bs, 4H), 2.70 (s, 3H), 1.75 (bs, 6H). Anal. Calcd. for $C_{20}H_{20}N_4OS$ (364.465): C, 65.91; H, 5.53; N, 15.37. Found: C, 66.74 H, 6.46; N, 15.27. Yield=15%.

Example 7

5-Methyl-4-(4-methylpiperazin-1-yl)-2-(4-nitrophenyl)thieno[2,3-d]pyrimidine-6-carbonitrile

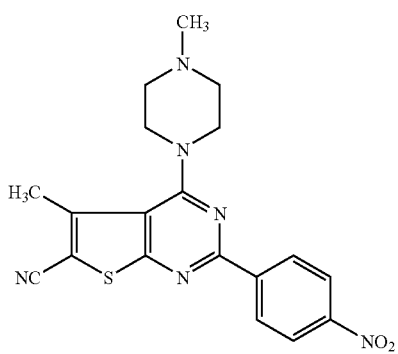

$^1$H-NMR (CDCl$_3$, 300 MHz) δ 8.63 (d, J=8.72 Hz, 2H), 8.31 (d, J=8.72 Hz, 2H), 3.68-3.65 (m, 4H), 2.73 (s, 3H), 2.63-2.60 (m, 4H), 2.36 (s, 3H); IR CHCl$_3$ ($v_{max}$) 3392, 2969, 2939, 2925, 2212, 1594, 1532, 1519, 1464, 1418, 1341, 1292, 1180, 1132, 1106, 1045, 994, 870, 844, 794, 762, 736, 709 cm⁻¹; MS (API-ES+, m/z) 395.1 (M+1)⁺. Anal. Calcd. for C$_{19}$H$_{18}$N$_6$O$_2$S (394.451): C, 57.85; H, 4.60; N, 21.31. Found: C, 49.04; H, 5.17; N, 14.08. Yield=57%.

Example 8

5-Methyl-2-phenyl-4-piperazin-1-ylthieno[2,3-d]pyrimidine-6-carbonitrile

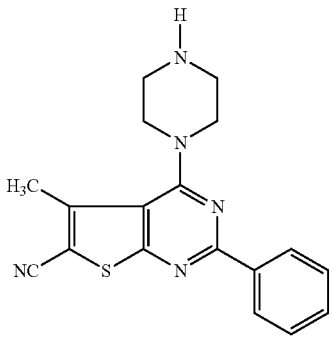

M.P. 251-253° C.; ¹H-NMR (CDCl$_3$, 200 MHz) δ 8.46-8.44 (m, 2H), 7.50-7.48 (m, 3H), 3.72-3.66 (m, 4H), 3.20-3.16 (m, 4H), 2.73 (s, 3H); IR CHCl$_3$ (ν$_{max}$) 3432, 2926, 2211, 1635, 1532, 1490, 1438, 1403, 1377, 1362, 1330, 1298, 1258, 1229, 1183, 1171, 1143, 1120, 1055, 1025, 862, 772, 706, 665 cm⁻¹. Anal. Calcd. for C$_{18}$H$_{17}$N$_5$S (335.427): C, 64.45; H, 5.11; N, 20.88. Found: C, 58.03; H, 4.87; N, 17.74. Yield=58%.

Example 9

2-(4-Methoxyphenyl)-5-methyl-4-(4-methylpiperazin-1-yl)thieno[2,3-d]pyrimidine-6-carbonitrile

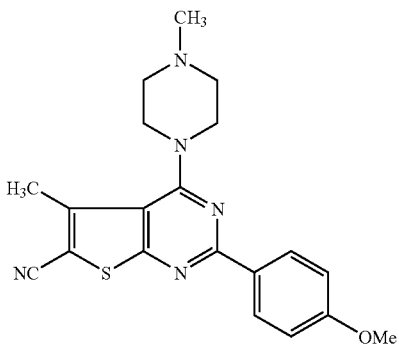

M.P.>250° C.; ¹H-NMR (CDCl$_3$, 200 MHz) δ 8.40 (d, J=8.84 Hz, 2H), 6.97 (d, J=8.84 Hz, 2H), 3.87 (s, 3H), 3.66-3.62 (m, 4H), 2.71 (s, 3H), 2.66-2.62 (m, 4H), 2.37 (s, 3H); IR CHCl$_3$ (ν$_{max}$) 3316, 2963, 2818, 2729, 2488, 2218, 1653, 1635, 1604, 1582, 1522, 1495, 1468, 1427, 1417, 1400, 1381, 1334, 1303, 1285, 1247, 1196, 1171, 1146, 1105, 1088, 1068, 1047, 1022, 1000, 975, 846, 792, 777, 746 cm⁻¹. Anal. Calcd. for C$_{20}$H$_{21}$N$_5$OS (379.480): C, 63.20; H, 5.58; N, 18.46. Found: C, 64.27; H, 5.71; N, 18.20. Yield=46%.

Example 10

4-(Diethylamino)-2-(4-methoxyphenyl)-5-methylthieno[2,3-d]pyrimidine-6-carbonitrile

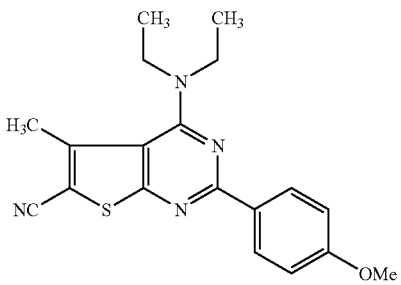

M.P. 154-156° C.; ¹H-NMR (CDCl$_3$, 200 MHz) δ 8.41 (d, J=9.0 Hz, 2H), 6.97 (d, J=9.0 Hz, 2H), 3.87 (s, 3H), 3.59 (q, J=6.8 Hz, 4H), 2.69 (s, 3H), 1.23 (t, J=6.8 Hz, 6H); IR (KBr) 3413, 2212, 1605, 1538, 1245, 1021, 848 cm⁻¹. Anal. Calcd. for C$_{19}$H$_{20}$N$_4$OS (352.454): C, 64.75; H, 5.72; N, 15.90. Found: C, 64.67; H, 5.86; N, 16.22. Yield=44%.

Example 11

2-(4-Methoxyphenyl)-5-methyl-4-pyrrolidin-1-ylthieno[2,3-d]pyrimidine-6-carbonitrile

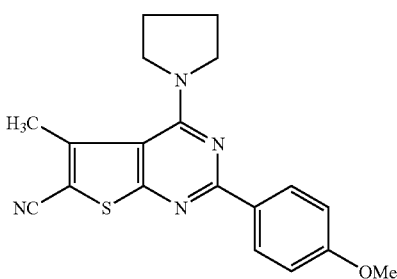

M.P. 176-178° C.; ¹H-NMR (CDCl$_3$, 300 MHz) δ 8.40 (d, 2H, J=8.7 Hz), 6.97 (d, 2H, J=8.7 Hz), 3.87 (s, 3H), 3.82-2.97 (m, 4H), 2.69 (s, 3H), 1.99-1.96 (m, 4H); IR (KBr) 2972, 2206, 1607, 1500, 1395, 1248, 1025 cm⁻¹. Anal. Calcd. for C$_{19}$H$_{18}$N$_4$OS (350.439): C, 65.12; H, 5.18; N, 15.99. Found: C, 65.30; H, 5.38; N, 19.32. Yield=43%.

Example 12

2-(4-Methoxyphenyl)-5-methyl-4-piperazin-1-ylthieno[2,3-d]pyrimidine-6-carbonitrile

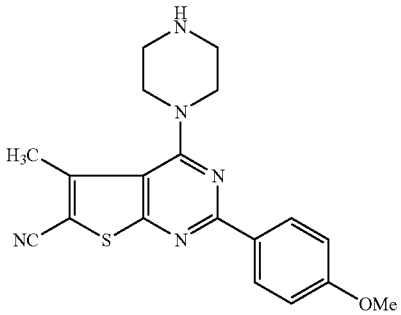

M.P. 210-212° C.; ¹H-NMR (CDCl₃, 200 MHz) δ 8.36 (2H, d, J=9.0 Hz, H-phenyl), 7.07 (d, J=9.0 Hz, 2H), 3.83 (s, 3H), 3.64-3.58 (m, 4H), 3.02-2.96 (m, 4H), 2.67 (s, 3H); IR (KBr) 3432, 2210, 1605, 1533, 1492, 1436, 1336, 1253, 1166, 1026, 980, 848, 794 cm⁻¹. Anal. Calcd. for $C_{19}H_{19}N_5OS$ (365.453): C, 62.44; H, 5.24; N, 19.16. Found: C, 60.72; H, 5.44; N, 19.44. Yield=36%.

Example 13

5-Methyl-2-(4-nitrophenyl)-4-piperazin-1-ylthieno[2,3-d]pyrimidine-6-carbonitrile

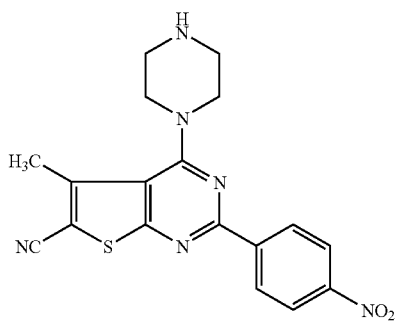

M.P. 250° C.; ¹H-NMR (CDCl₃, 300 MHz) δ 8.43 (d, J=8.8 Hz, 2H), 8.33 (d, J=8.8 Hz, 2H), 3.50-3.45 (m, 4H), 3.36-3.31 (m, 4H), 2.67 (s, 3H); IR (KBr) 3447, 3090, 2219, 1667, 1551, 1521, 1482, 1428, 1379, 1337, 1295, 1211, 1107, 1042, 1004, 870, 845, 709, 647, 538 cm⁻¹. Anal. Calcd. for $C_{18}H_{16}N_6O_2S$ (380.425): C, 56.83; H, 4.24; N, 22.09. Found: C, 56.79; H, 4.76; N, 22.79. Yield=62%.

Example 14

4-(Dibutylamino)-2-(4-methoxyphenyl)-5-methylthieno[2,3-d]pyrimidine-6-carbonitrile

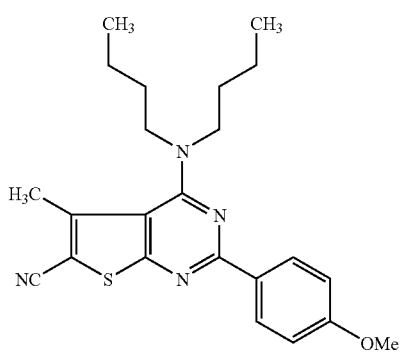

M.P. 96-98° C.; ¹H-NMR (CDCl₃, 300 MHz) δ 8.42 (d, 2H, J=8.9 Hz), 6.99 (d, 2H, J=8.9 Hz), 3.88 (s, 3H), 3.55 (t, 4H, J=7.2 Hz), 2.69 (s, 3H), 1.63 (q, 4H, J=7.2 Hz), 1.25 (hex, 4H, J=7.2 Hz), 0.88 (t, 6H, J=7.2 Hz); IR (KBr) 2957, 2210, 1606, 1531, 1334, 1251 cm⁻¹. Anal. Calcd. for $C_{23}H_{28}N_4OS$ (408.561): C, 67.61; H, 6.91; N, 13.71. Found: C, 67.87; H, 6.89; N, 13.53. Yield=38%.

Example 15

2-(4-Chlorophenyl)-5-methyl-4-(4-methylpiperazin-1-yl)thieno[2,3-d]pyrimidine-6-carbonitrile

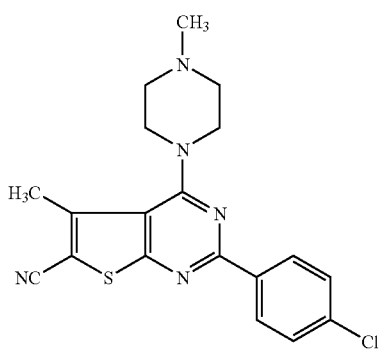

M.p. 209-210° C.; ¹H-NMR (CDCl₃, 200 MHz) δ 8.41 (d, 2H, J=8.5 Hz), 7.45 (d, 2H, J=8.5 Hz), 3.66 (t, 4H, J=4.6 Hz), 2.74 (s, 3H), 2.63 (t, 4H, J=4.6 Hz), 2.36 (s, 3H); IR (KBr) 2937, 2212, 1532, 1446, 1264, 1089 cm⁻¹; MS (API-ES+, m/z) 384 (M+1)⁺. Anal. Calcd. for $C_{19}H_{18}ClN_5S$ (383.899): C, 59.44; H, 4.73; N, 18.24. Found: C, 59.12; H, 4.79; N, 18.53. Yield=30%.

Example 16

2-(3,4-Dimethoxyphenyl)-5-methyl-4-(4-methylpiperazin-1-yl)thieno[2,3-d]pyrimidine-6-carbonitrile

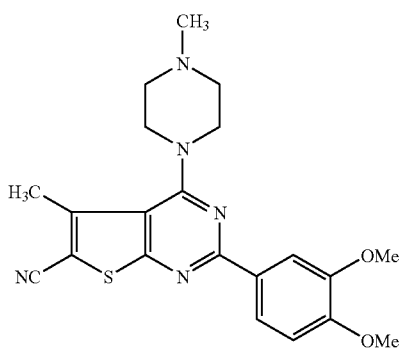

M.P. 208-209° C.; ¹H-NMR (CDCl₃, 200 MHz) δ 8.12 (dd, 1H, J=8.4, 1.8 Hz), 8.05 (d, 1H, J=1.8 Hz), 6.98 (d, 1H, J=8.4 Hz), 4.03 (s, 3H), 3.98 (s, 3H), 3.64 (t, 4H, J=4.6 Hz), 2.74 (s, 3H), 2.64 (t, 4H, J=4.6 Hz), 2.39 (s, 3H); IR (KBr) 2933, 2210, 1517, 1456, 1251, 1025 cm⁻¹; MS (API-ES+, m/z) 384 (M−CN+1)⁺. Anal. Calcd. for $C_{12}H_{23}N_5O_2S$ (409.506): C, 61.59; H, 5.66; N, 17.10. Found: C, 55.24; H, 5.64; N, 16.71. Yield=16%.

Example 17

4-[Ethyl(methyl)amino]-2-(4-methoxyphenyl)-5-methylthieno[2,3-d]pyrimidine-6-carbonitrile

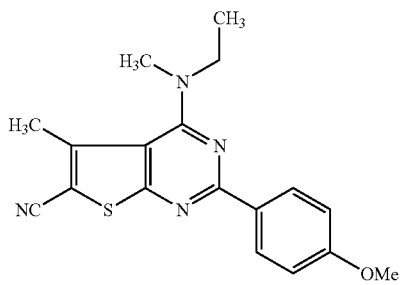

M.P. 122-123° C.; $^1$H-NMR (CDCl$_3$, 300 MHz) δ 8.42 (d, 2H, J=8.9 Hz), 6.98 (d, 2H, J=8.9 Hz), 3.89 (s, 3H), 3.64 (q, 2H, J=7.1 Hz), 3.14 (s, 3H), 2.70 (s, 3H), 1.32 (t, 3H, J=7.1 Hz); IR (KBr) 2933, 2209, 1606, 1582, 1395, 1250 cm$^{-1}$; MS (API-ES+, m/z) 339 (M+1)$^+$. Anal. Calcd. for C$_{18}$H$_{18}$N$_4$OS (338.428): C, 63.88; H, 5.36; N, 16.56. Found: C, 63.83; H, 5.37; N, 16.55. Yield=58%.

Example 18

4-(Diethylamino)-5-methyl-2-(4-nitrophenyl)thieno[2,3-d]pyrimidine-6-carbonitrile

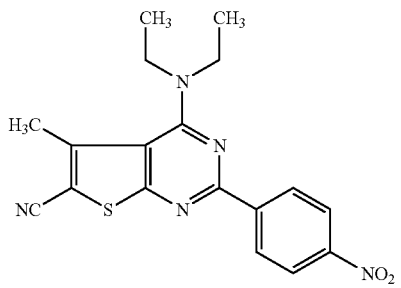

$^1$H-NMR (CDCl$_3$, 200 MHz) δ 8.61 (d, J=9.0 Hz, 2H), 8.30 (d, J=9.0 Hz, 2H), 3.64 (q, J=6.9 Hz, 4H), 2.71 (s, 3H), 1.26 (t, J=6.9 Hz, 6H); IR (KBr) 3429, 2925, 2360, 2208, 1730, 1596, 1535, 1276, 714 cm$^{-1}$. C$_{18}$H$_{17}$N$_5$O$_2$S (367.426). Yield=44%.

Example 19

2-(4-Chlorophenyl)-4-(diethylamino)-5-methylthieno[2,3-d]pyrimidine-6-carbonitrile

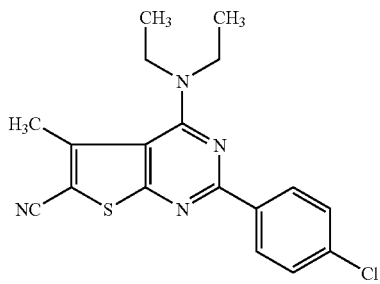

$^1$H-NMR (CDCl$_3$, 200 MHz) δ 8.38 (d, J=8.7 Hz, 2H), 7.42 (d, J=8.7 Hz, 2H), 3.58 (q, J=6.9 Hz, 4H), 2.69 (s, 3H), 1.23 (t, J=6.9 Hz, 6H); IR (KBr) 3394, 2969, 2921, 2860, 2360, 2211, 1531, 849, 736 cm$^{-1}$. Anal. Calcd. for C$_{18}$H$_{17}$ClN$_4$S (356.873): C, 60.58; H, 4.80; N, 15.70. Found: C, 59.41; H, 5.66; N, 12.68. Yield=45%.

Example 20

4-(Diethylamino)-2-(3,4-dimethoxyphenyl)-5-methylthieno[2,3-d]pyrimidine-6-carbonitrile

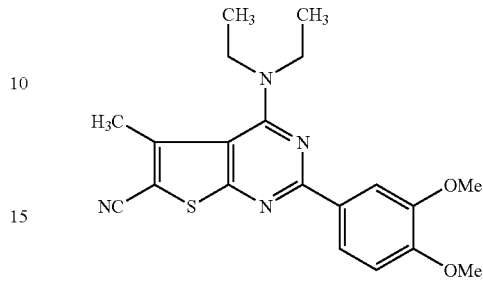

M.P. 159-161° C.; $^1$H-NMR (CDCl$_3$, 200 MHz) δ 8.02-8.11 (m, 2H); 6.94 (d, J=8.4 Hz, 1H), 3.99 (s, 3H), 3.94 (s, 3H), 3.58 (q, J=6.9 Hz, 4H), 2.68 (s, 3H), 1.23 (t, J=6.9 Hz, 6H); IR (KBr) 3448, 2987, 2213, 1516, 1018, 796 cm$^-$. Anal. Calcd. for C$_{20}$H$_{22}$N$_4$O$_2$S (382.480): C, 62.80; H, 5.80; N, 14.65. Found: C, 61.23; H, 5.76; N, 14.04. Yield=22%.

Example 21

4-(Dimethylamino)-2-(4-methoxyphenyl)-5-methylthieno[2,3-d]pyrimidine-6-carbonitrile

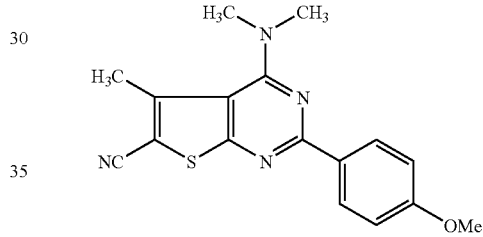

M.p. 123-125° C.; $^1$H-NMR (CDCl$_3$, 300 MHz) δ 8.42 (d, J=8.7 Hz, 2H), 6.96 (d, J=8.7 Hz, 2H), 3.86 (s, 3H), 3.26 (s, 6H), 2.70 (s, 3H); IR (KBr) 3419, 2926, 2853, 2206, 1606, 1512, 839 cm$^{-1}$. C$_{17}$H$_{16}$N$_4$OS (324.401). Yield=23%.

Example 22

2-(4-Methoxyphenyl)-5-methyl-4-morpholin-4-ylthieno[2,3-d]pyrimidine-6-carbonitrile

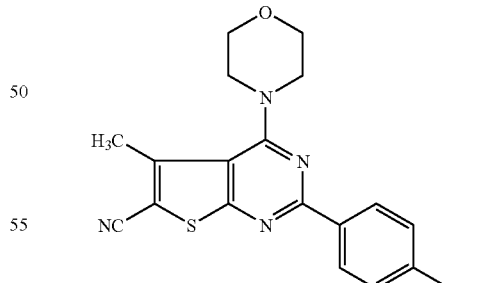

M.p. 204-206° C.; $^1$H-NMR (CDCl$_3$, 200 MHz) δ 8.41 (d, J=8.8 Hz, 2H), 6.97 (d, J=8.8 Hz, 2H), 3.92-3.88 (m, 4H), 3.87 (s, 3H), 3.60-3.56 (m, 4H), 2.72 (s, 3H); IR (KBr) 3438, 2964, 2837, 2210, 1605, 1583, 1533, 1489, 1464, 1426, 1400, 1380, 1363, 1326, 1301, 1252, 1235, 1189, 1162, 1118, 1067, 1030, 985, 926, 869, 847, 796, 748, 698, 672, 635, 614, 563, 484 cm$^{-1}$. Anal. Calcd. for C$_{19}$H$_{18}$N$_4$O$_2$S (366.438): C, 62.28; H, 4.95; N, 15.29. Found: C, 58.38; H, 4.76; N, 14.32. Yield=55%.

Example 23

2-(4-Chlorophenyl)-5-methyl-4-morpholin-4-ylthieno[2,3-d]pyrimidine-6-carbonitrile

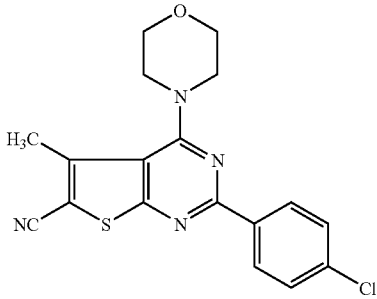

M.p. 205-207° C.; $^1$H-NMR (CDCl$_3$, 300 MHz) δ 8.40 (d, J=8.50 Hz, 2H), 7.43 (d, J=8.50 Hz, 2H), 3.91-3.88 (m, 4H), 3.61-3.60 (m, 4H), 2.72 (s, 3H). Anal. Calcd. for C$_{18}$H$_{15}$ClN$_4$OS (370.857): C, 58.30; H, 4.08; N, 15.11. Found: C, 42.51; H, 6.56; N, 11.03. Yield=69%.

Example 24

2-(4-Methoxyphenyl)-5-methyl-4-[methyl(prop-2-ynyl)amino]thieno[2,3-d]pyrimidine-6-carbonitrile

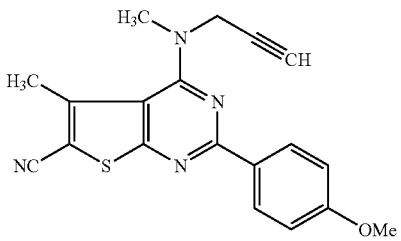

M.p. 160-171° C.; $^1$H-NMR (CDCl$_3$, 300 MHz) δ 8.42 (d, J=9.10 Hz, 2H), 6.96 (d, J=9.10 Hz, 2H), 4.26 (d, J=2.35 Hz), 3.85 (s, 3H), 3.18 (s, 3H), 2.72 (s, 3H), 2.02 (s, 1H). Anal. Calcd. for C$_{19}$H$_{16}$N$_4$OS (348.423): C, 65.50; H, 4.63; N, 16.08. Found: C, 63.56; H, 4.84; N, 11.03. Yield=39%.

Example 25

4-[(2-Hydroxyethyl)(methyl)amino]-2-(4-methoxyphenyl)-5-methylthieno[2,3-d]pyrimidine-6-carbonitrile

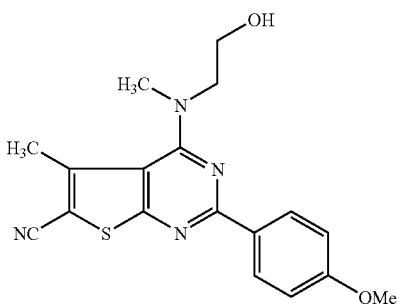

M.P. 144-146° C.; $^1$H-NMR (CDCl$_3$, 300 MHz) δ 8.25 (d, J=8.74 Hz, 2H), 6.90 (d, J=8.74 Hz, 2H), 3.93 (t, J=4.6 Hz, 2H), 3.82 (t, J=4.6 Hz, 2H), 3.80 (s, 3H), 3.15 (s, 3H), 2.62 (s, 3H). Anal. Calcd. for C$_{18}$H$_{18}$N$_4$O$_2$S (354.427): C, 61.00; H, 5.12; N, 15.81. Found: C, 60.74; H, 5.31; N, 14.78. Yield=43%.

Example 26

2-(3,4-Dimethoxyphenyl)-4-[ethyl(methyl)amino]-5-methylthieno[2,3-d]pyrimidine-6-carbonitrile

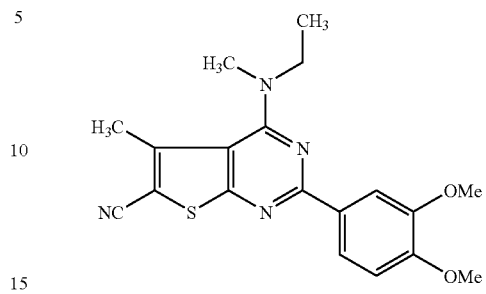

M.P. 133-135° C.; $^1$H-NMR (CDCl$_3$, 200 MHz) δ 8.11 (dd, 1H, J=8.4, 2.0 Hz), 8.05 (d, 1H, J=2.0 Hz), 6.96 (d, 1H, J=8.4 Hz), 4.01 (s, 3H), 3.96 (s, 3H), 3.65 (q, 2H, J=7.0 Hz), 3.15 (s, 3H), 2.71 (s, 3H), 1.33 (t, 3H, J=7.0 Hz); IR (KBr) 2210, 1601, 1538, 1418, 1339, 1271, 1024 cm$^{-1}$. Anal. Calcd. for C$_{19}$H$_{20}$N$_4$O$_2$S (368.454): C, 61.94; H, 5.47; N, 15.21. Found: C, 60.34; H, 5.42; N, 14.09. Yield=50%.

Example 27

5-Methyl-2-(4-methylphenyl)-4-(4-methylpiperazin-1-yl)thieno[2,3-d]pyrimidine-6-carbonitrile

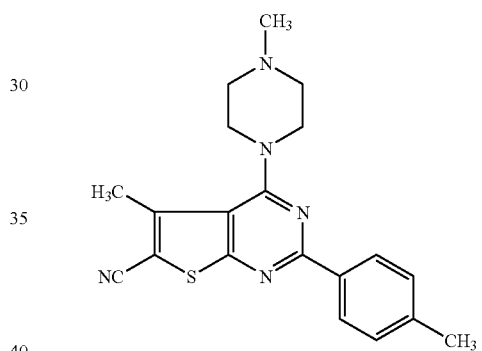

M.P. 207-209° C.; $^1$H-NMR (CDCl$_3$, 200 MHz) δ 8.36 (d, 2H, J=8.2 Hz), 7.29 (d, 2H, J=8.2 Hz), 3.65 (t, 4H, J=4.6 Hz), 2.74 (s, 3H), 2.63 (t, 4H, J=4.6 Hz), 2.44 (s, 3H), 2.38 (s, 3H); IR (KBr) 2797, 2211, 1533, 1492, 1363, 1172 cm$^{-1}$. Anal. Calcd. for C$_{20}$H$_{21}$N$_5$S (363.480): C, 66.09; H, 5.82; N, 19.27. Found: C, 64.11; H, 5.77; N, 18.45. Yield=34%.

Example 28

4-(Diethylamino)-5-methyl-2-[4-(trifluoromethyl)phenyl]thieno[2,3-d]pyrimidine-6-carbonitrile

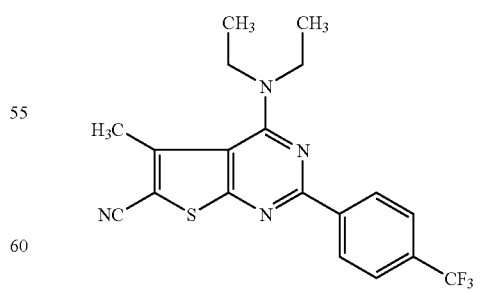

$^1$H-NMR (CDCl$_3$, 200 MHz) δ 8.55 (d, J=8.2 Hz, 2H), 7.71 (d, J=8.2 Hz, 2H), 3.63 (q, J=6.9 Hz, 4H), 2.71 (s, 3H), 1.25 (t, J=6.9 Hz, 6H); IR (KBr) 3419, 2976, 2926, 2209, 1535, 1517, 1325, 1116, 854, 695 cm$^{-1}$. C$_{19}$H$_{17}$F$_3$N$_4$S (390.426). Yield=33%.

Example 29

4-[Allyl(methyl)amino]-2-(4-methoxyphenyl)-5-methylthieno[2,3-d]pyrimidine-6-carbonitrile

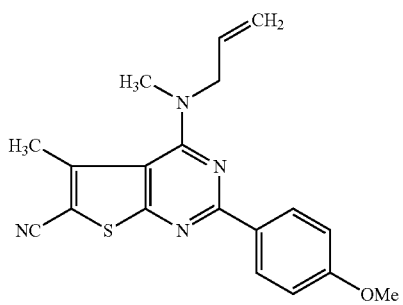

M.P. 126-128° C.; ¹H-NMR (CDCl₃, 200 MHz) δ 8.40 (d, J=8.4 Hz, 2H), 6.96 (d, J=8.4 Hz, 2H), 5.92-6.00 (m, 1H), 5.27-5.37 (m, 2H), 4.17 (d, J=5.4 Hz, 2H), 3.87 (s, 3H), 3.09 (s, 3H), 2.70 (s, 3H); IR (KBr) 3433, 2962, 2916, 2360, 2206, 1533, 1251, 1168, 847, 790 cm⁻¹. Anal. Calcd. for $C_{19}H_{18}N_4OS$ (350.439): C, 65.12; H, 5.18; N, 15.99. Found: C, 65.70; H, 6.13; N, 13.52. Yield=23%.

Example 30

2-(3,4-Dimethoxyphenyl)-4-[(2-hydroxyethyl)(methyl)amino]-5-methylthieno[2,3-d]pyrimidine-6-carbonitrile

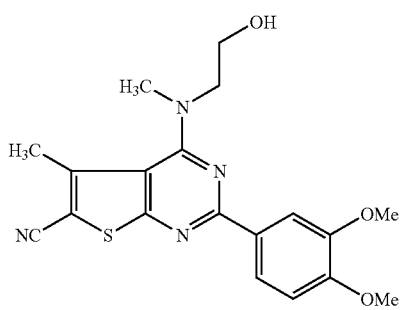

¹H-NMR (CDCl₃, 300 MHz) δ 7.87-7.78 (m, 2H), 7.09 (d, J=8.45 Hz, 1H), 4.88 (m, 2H), 4.03 (m, 2H), 3.84 (s, 6H), 2.65 (s, 3H), 2.48 (s, 3H); MS (API-ES+, m/z) 385.1 (M+1)⁺. $C_{19}H_{20}N_4O_3S$ (384.453). Yield=9%.

Example 31

2-(3,4-Dimethoxyphenyl)-5-methyl-4-morpholin-4-ylthieno[2,3-d]pyrimidine-6-carbonitrile

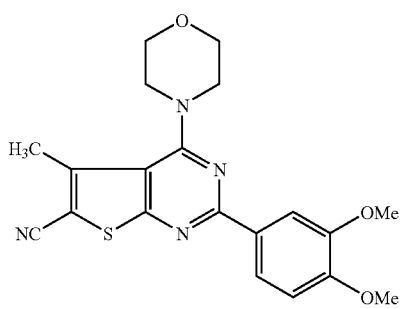

M.P. 194-196° C.; ¹H-NMR (CDCl₃, 300 MHz) δ 8.11-8.02 (m, 3H), 6.95 (d, J=8.46 Hz, 1H), 4.00 (s, 3H), 3.95 (s, 3H), 3.92-3.88 (m, 4H), 3.60-3.56 (m, 4H), 2.72 (s, 3H); IR (KBr) 3448, 2963, 2838, 2361, 2209, 1600, 1535, 1492, 1463, 1407, 1378, 1339, 1267, 1252, 1230, 1183, 1136, 1113, 1064, 1024, 990, 915, 876, 861, 827, 790, 768, 740, 676 cm⁻¹. Anal. Calcd. for $C_{20}H_{20}N_4O_3S$ (396.464): C, 60.59; H, 5.08; N, 14.13. Found: C, 60.04; H, 5.09; N, 13.94. Yield=47%.

Example 32

5-Methyl-2-(4-methylphenyl)-4-morpholin-4-ylthieno[2,3-d]pyrimidine-6-carbonitrile

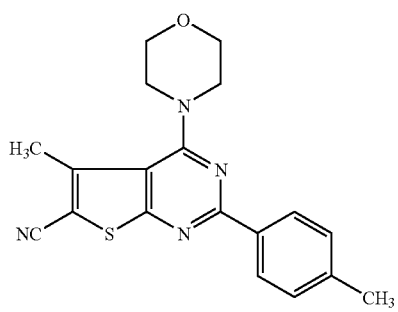

M.P. 206-207° C.; ¹H-NMR (CDCl₃, 300 MHz) δ 8.34 (d, J=8.14 Hz, 2H), 7.27 (d, J=8.14 Hz, 2H), 3.91-3.88 (m, 4H), 3.61-3.58 (m, 4H), 2.72 (s, 3H), 2.41 (s, 3H); IR (KBr) 3447, 3023, 2982, 2928, 2863, 2210, 1605, 1524, 1489, 1441, 1377, 1329, 1267, 1170, 1112, 987, 868, 791, 735 cm⁻¹. Anal. Calcd. for $C_{19}H_{18}N_4OS$ (350.439): C, 65.12; H, 5.18; N, 15.99. Found: C, 59.65; H, 4.85; N, 14.64. Yield=92%.

Example 33

5-Methyl-4-(4-methylpiperazin-1-yl)-2-[4-(trifluoromethyl)phenyl]thieno[2,3-d]pyrimidine-6-carbonitrile

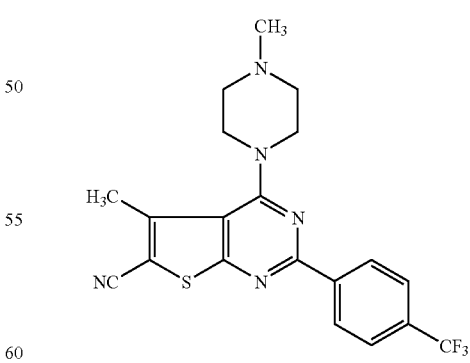

M.P. 187-189° C.; ¹H-NMR (CDCl₃, 200 MHz) δ 8.58 (d, J=8.2 Hz, 2H), 7.73 (d, J=8.2 Hz, 2H), 3.67 (t, J=4.6 Hz, 4H), 2.74 (s, 3H), 2.63 (t, J=4.6 Hz, 4H), 2.38 (s, 3H). Anal. Calcd. for $C_{20}H_{18}F_3N_5S$ (417.452): C, 57.54; H, 4.35; N, 16.78. Found: C, 57.75; H, 4.76; N, 15.98. Yield=29%.

Example 34

2-1,3-Benzodioxol-5-yl)-5-methyl-4-(4-methylpiperazin-1-yl)thieno[2,3-d]pyrimidine-6-carbonitrile

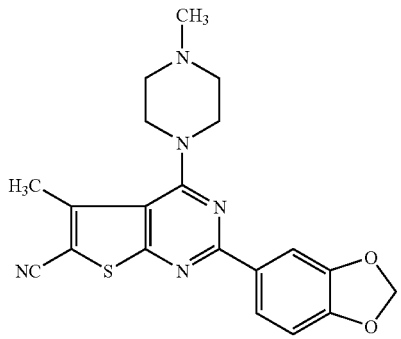

M.P. 196-197° C.; $^1$H-NMR (CDCl$_3$, 200 MHz) δ 8.07 (d, J=8.4 Hz, 1H), 7.92 (s, 1H), 6.89 (d, J=8.2 Hz, 1H), 6.04 (s, 2H), 3.61 (t, J=4.6 Hz, 4H), 2.71 (s, 3H), 2.61 (t, J=4.6 Hz, 4H), 2.37 (s, 3H). Anal. Calcd. for C$_{20}$H$_{19}$N$_5$O$_2$S (393.463): C, 61.05; H, 4.87; N, 17.80. Found: C, 59.92; H, 4.91; N, 17.26. Yield=43%.

Example 35

4-(Diethylamino)-5-methyl-2-(4-methylphenyl)thieno[2,3-d]pyrimidine-6-carbonitrile

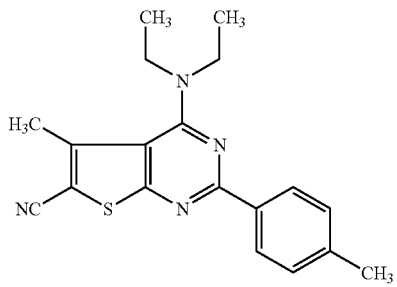

$^1$H-NMR (CDCl$_3$, 300 MHz) δ 8.33 (d, J=8.0 Hz, 2H), 7.24 (d, J=8.0 Hz, 2H), 3.58 (q, J=6.9 Hz, 4H), 2.69 (s, 3H), 2.41 (s, 3H), 1.22 (t, J=6.9 Hz, 6H); IR (KBr) 3440, 2970, 2928, 2209, 1534, 734 cm$^{-1}$. C$_{19}$H$_{20}$N$_4$S (336.455). Yield=32%.

Example 36

2-(1,3-Benzodioxol-5-yl)-4-(diethylamino)-5-methylthieno[2,3-d]pyrimidine-6-carbonitrile

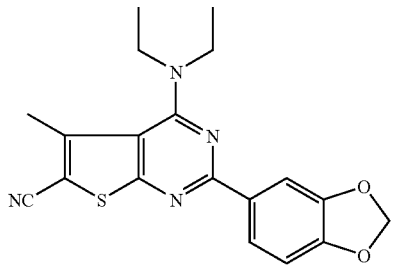

M.P. 199-201° C.; $^1$H-NMR (CDCl$_3$, 300 MHz) δ 8.06 (d, J=8.2 Hz, 1H), 7.92 (s, 1H), 6.88 (d, J=8.2 Hz, 1H), 6.02 (s, 2H), 3.58 (q, J=6.9 Hz, 4H), 2.67 (s, 3H), 1.22 (t, J=6.9 Hz, 6H); IR (KBr) 3440, 2972, 2901, 2205, 1531, 1445, 1035, 928, 737 cm$^{-1}$. Anal. Calcd. for C$_{19}$H$_{18}$N$_4$O$_2$S (366.438): C, 62.28; H, 4.95; N, 15.29. Found: C, 63.84; H, 5.67; N, 14.28. Yield=17%.

Example 37

2-(1,3-Benzodioxol-5-yl)-5-methyl-4-morpholin-4-ylthieno[2,3-d]pyrimidine-6-carbonitrile

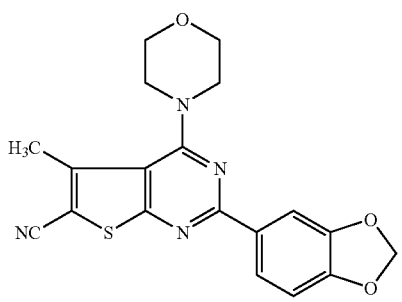

M.P. 197-198° C.; $^1$H-NMR (CDCl$_3$, 300 MHz) δ 8.07 (dd, J=8.24 y 1.65 Hz, 1H), 7.92 (d, J=1.65 Hz, 1H), 6.89 (d, J=8.24 Hz, 1H), 6.03 (s, 2H), 3.90-3.87 (m, 4H), 3.59-3.50 (m, 4H), 2.71 (s, 3H); IR (KBr) 3445, 2960, 2901, 2858, 2207, 1376, 1358, 1324, 1257, 1231, 1178, 1149, 1111, 1066, 917, 878, 862, 827, 811, 789, 738, 713 cm$^{-1}$. Anal. Calcd. for C$_{19}$H$_{16}$N$_4$O$_3$S (380.422): C, 59.99; H, 4.24; N, 14.73. Found: C, 58.82; H, 4.20; N, 14.25. Yield=57%.

Example 38

4-[Ethyl(methyl)amino]-5-methyl-2-pyridin-4-ylthieno[2,3-d]pyrimidine-6-carbonitrile

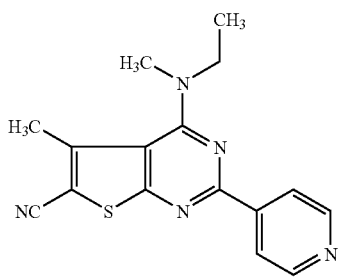

M.p. 162-164° C.; $^1$H-NMR (CDCl$_3$, 200 MHz) δ 8.75 (d, J=6.2 Hz, 2H), 8.28 (d, J=6.2 Hz, 2H), 3.70 (q, J=7.0 Hz, 2H), 3.9 (s, 3H), 2.73 (s, 3H), 1.35 (t, J=7.0 Hz, 3H); IR (KBr) 2970, 2212, 1599, 1539, 1381, 1181, 1024 cm$^{-1}$. Anal. Calcd. for C$_{16}$H$_{15}$N$_5$S (309.390): C, 62.11; H, 4.89; N, 22.64. Found: C, 61.46; H, 4.83; N, 21.87. Yield=55%.

Example 39

4-[Ethyl(methyl)amino]-5-methyl-2-(3,4,5-trimethoxyphenyl)thieno[2,3-d]pyrimidine-6-carbonitrile

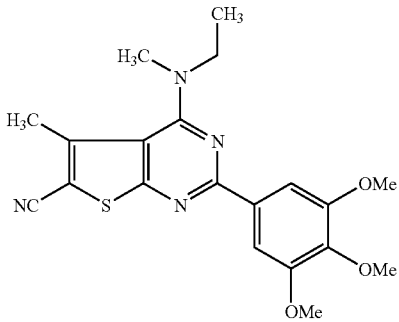

M.P. 163-164° C.; $^1$H-NMR (CDCl$_3$, 200 MHz) δ 7.78 (s, 2H), 3.99 (s, 6H), 3.93 (s, 3H), 3.67 (q, J=7.2 Hz, 2H), 3.16 (s, 3H), 2.72 (s, 3H), 1.35 (t, J=7.2 Hz, 3H); IR (KBr) 2937, 2210, 1537, 1391, 1127 cm$^{-1}$. Anal. Calcd. for C$_{20}$H$_{22}$N$_4$O$_3$S (398.480): C, 60.28; H, 5.56; N, 14.06. Found: C, 59.98; H, 5.43; N, 13.95. Yield=55%.

Example 40

2-Benzyl-5-methyl-4-(4-methylpiperazin-1-yl)thieno[2,3-d]pyrimidine-6-carbonitrile

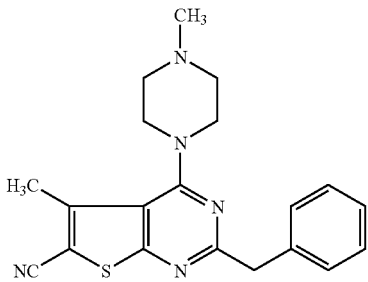

Oil; $^1$H-NMR (CDCl$_3$, 200 MHz) δ 7.42-7.24 (m, 5H), 4.17 (s, 2H), 3.53 (t, J=4.6 Hz, 4H), 2.67 (s, 3H), 2.53 (t, J=4.6 Hz, 4H), 2.34 (s, 3H); IR (KBr) 2934, 2212, 1532, 1261, 1140 cm$^{-1}$. Anal. Calcd. for C$_{20}$H$_{21}$N$_5$S (363.480): C, 66.09; H, 5.82; N, 19.27. Found: C, 64.48; H, 5.90; N, 19.51. Yield=81%.

Example 41

5-Methyl-4-morpholin-4-yl-2-pyridin-4-ylthieno[2,3-d]pyrimidine-6-carbonitrile

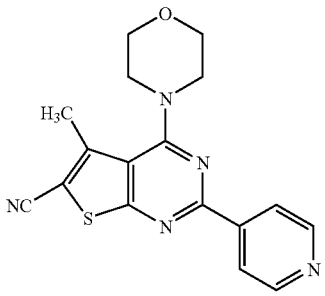

M.P.>250° C.; $^1$H-NMR (CDCl$_3$, 200 MHz) δ 8.75 (d, J=5.51 Hz, 2H), 8.27 (d, J=5.51 Hz, 2H), 3.92-3.88 (m, 4H), 3.66-3.62 (m, 4H), 2.74 (s, 3H); IR (KBr) 3434, 2950, 2922, 2852, 2210, 1448, 1427, 1401, 1379, 1367, 1324, 1301, 1242, 1181, 1110, 1053, 1011, 984, 916, 869, 846, 789 cm$^{-1}$. Anal. Calcd. for C$_{17}$H$_{15}$N$_5$OS (337.400): C, 60.52; H, 4.48; N, 20.76. Found: C, 58.97; H, 4.50; N, 20.05. Yield=53%.

Example 42

4-[(2-Hydroxyethyl)(methyl)amino]-5-methyl-2-pyridin-4-ylthieno[2,3-d]pyrimidine-6-carbonitrile

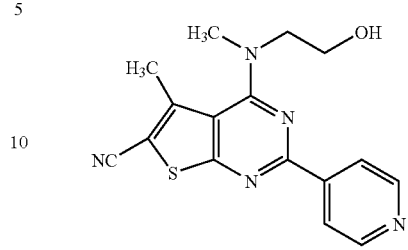

M.P. 194-195° C.; $^1$H-NMR (CDCl$_3$, 200 MHz) δ 8.73 (d, J=6.15 Hz, 2H), 8.30 (d, J=6.15 Hz, 2H), 3.64-3.57 (m, 2H), 3.53-3.48 (m, 2H), 3.38 (s, 3H), 2.76 (s, 3H); IR (KBr) 3279, 2215, 1601, 1566, 1534, 1518, 1492, 1439, 1400, 1371, 1331, 1270, 1155, 1123, 1069, 1038, 1000, 845, 795, 748, 702, 672 cm$^{-1}$. Anal. Calcd. for C$_{16}$H$_{15}$N$_5$OS (325.389): C, 59.06; H, 4.65; N, 21.52. Found: C, 48.32; H, 4.02; N, 21.90. Yield=40%.

Example 43

2-(1,3-Benzodioxol-5-yl)-4-[(2-hydroxyethyl)(methyl)amino]-5-methylthieno[2,3-d]pyrimidine-6-carbonitrile

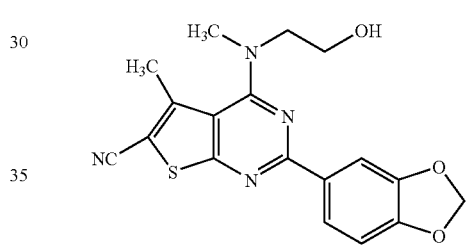

M.P. 195-197° C.; $^1$H-NMR (CDCl$_3$, 300 MHz) δ 7.99 (dd, J=8.24 y 1.65 Hz, 1H), 7.86 (d, J=1.65 Hz, 1H), 6.89 (d, J=8.24 Hz, 1H), 6.02 (s, 2H), 4.01-3.97 (m, 2H), 3.91-3.87 (m, 2H), 3.22 (s, 3H), 2.71 (s, 3H); IR (KBr) 3548, 3426, 2901, 2206, 1735, 1625, 1539, 1501, 1444, 1404, 1377, 1363, 1343, 1324, 1249, 1192, 1109, 1076, 1059, 1032, 1009, 953, 933, 914, 878, 833, 812, 792, 738, 713 cm$^{-1}$. Anal. Calcd. for C$_{18}$H$_{16}$N$_4$O$_3$S (368.411): C, 58.68; H, 4.38; N, 15.21. Found: C, 57.66; H, 4.56; N, 15.01. Yield=39%.

Example 44

4-[(2-Hydroxyethyl)(methyl)amino]-5-methyl-2-(4-methylphenyl)thieno[2,3-d]pyrimidine-6-carbonitrile

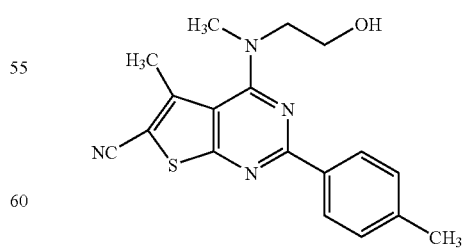

$^1$H-NMR (CDCl$_3$, 300 MHz) δ 8.35 (d, J=8.24 Hz, 2H), 7.49 (d, J=8.24 Hz, 2H), 4.00-3.97 (m, 2H), 3.91-3.88 (m, 2H), 3.22 (s, 3H), 2.70 (s, 3H), 2.40 (s, 3H); IR (KBr) 3457, 3413, 2960, 2921, 2211, 1670, 1610, 1535, 1495, 1436, 1408, 1391, 1375, 1331, 1302, 1173, 1125, 1050, 1028, 1005, 835, 788, 736, 692 cm$^{-1}$. Anal. Calcd. for C$_{18}$H$_{18}$N$_4$OS (338.428): C, 63.88; H, 5.36; N, 16.56. Found: C, 62.71; H, 5.68; N, 16.26. Yield=42%.

Example 45

4-(Diethylamino)-5-methyl-2-pyridin-4-ylthieno[2,3-d]pyrimidine-6-carbonitrile

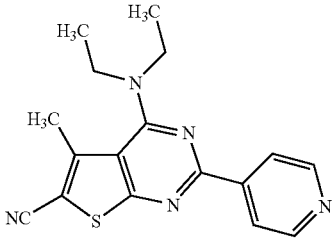

M.P. 169-171° C.; $^1$H-NMR (CDCl$_3$, 300 MHz) δ 8.75 (d, J=6.0 Hz, 2H); 8.26 (d, J=6.0 Hz, 2H), 3.63 (q, J=7.1 Hz, 4H), 2.70 (s, 3H), 1.25 (t, J=7.1 Hz, 6H); IR (KBr) 3423, 2924, 2212, 1597, 1535, 842, 785 cm$^{-1}$. Anal. Calcd. for C$_{17}$H$_{17}$N$_5$S (323.417): C, 63.13; H, 5.30; N, 21.65. Found: C, 63.97; H, 5.40; N, 21.47. Yield=8%.

Example 46

2-(3,4-Dimethoxyphenyl)-4-(dimethylamino)-5-methylthieno[2,3-d]pyrimidine-6-carbonitrile

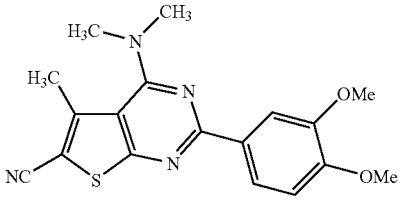

M.P. 198-200° C.; $^1$H-NMR (CDCl$_3$, 200 MHz) δ 8.10 (d, J=8.4 Hz, 1H), 8.03 (s, 1H), 6.93 (d, J=8.4 Hz, 1H), 4.00 (s, 3H), 3.94 (s, 3H), 3.17 (s, 6H), 2.71 (s, 3H); IR (KBr) 3440, 2110, 1667, 1602, 1456, 1024, 790 cm$^{-1}$. C$_{18}$H$_{18}$N$_4$O$_2$S (354.427). Yield=12%.

Example 47

2-(3,4-Dimethoxyphenyl)-5-methyl-4-(propylamino)thieno[2,3-d]pyrimidine-6-carbonitrile

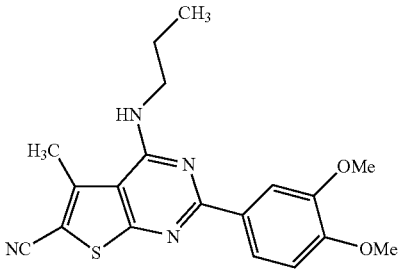

M.P. 179-181° C.; $^1$H-NMR (CDCl$_3$, 200 MHz) δ 8.09 (d, J=8.4 Hz, 1H), 8.04 (s, 1H), 6.94 (d, J=8.4 Hz, 1H), 5.53 (bs, 1H), 4.00 (s, 3H), 3.95 (s 3H), 3.62-3.74 (m, 2H), 2.77 (s, 3H), 1.72-1.85 (m, 2H), 1.06 (t, J=7.4 Hz, 3H); IR (KBr) 3440, 2926, 2204, 1671, 1556, 1269, 785 cm$^{-1}$. Anal. Calcd. for C$_{19}$H$_{20}$N$_4$O$_2$S (368.454): C, 61.94; H, 5.47; N, 15.21. Found: C, 60.97; H, 6.00; N, 15.11. Yield=6%.

Example 48

4-(Diethylamino)-5-methyl-2-(3,4,5-trimethoxyphenyl)thieno[2,3-d]pyrimidine-6-carbonitrile

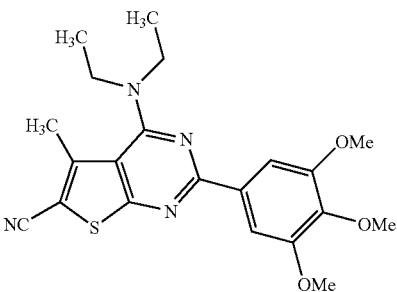

$^1$H-NMR (CDCl$_3$, 200 MHz) δ 7.76 (s, 2H), 3.97 (s, 6H), 3.91 (s, 3H), 3.59 (q, J=7.1 Hz, 4H), 2.70 (s, 3H), 1.25 (t, J=7.1 Hz, 6H); IR (KBr) 3438, 2962, 2936, 2210, 1737, 1531, 1127, 858, 713 cm$^{-1}$. Anal. Calcd. for C$_{21}$H$_{24}$N$_4$O$_3$S (412.506): C, 61.14; H, 5.86; N, 13.58. Found: C, 61.00; H, 6.44; N, 13.92. Yield=33%.

Example 49

2-Benzyl-4-(diethylamino)-5-methylthieno[2,3-d]pyrimidine-6-carbonitrile

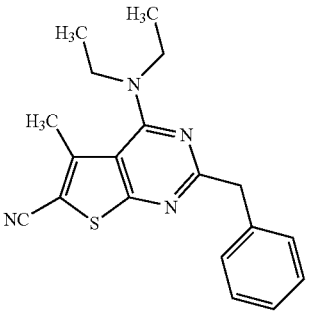

$^1$H-NMR (CDCl$_3$, 200 MHz) δ 7.17-7.38 (m, 5H), 4.13 (s, 2H), 3.51 (q, J=6.9 Hz, 4H), 2.62 (s, 3H), 1.12 (t, J=6.9 Hz, 6H), IR (KBr) 3369, 1727, 1534, 1494, 794 cm$^{-1}$. C$_{19}$H$_{20}$N$_4$S (336.455). Yield=12%.

Example 50

5-Methyl-4-(4-methyl-piperazin-1-yl)-2-phenyl-thieno[2,3-d-]pyrimidine-6-carbonitrile

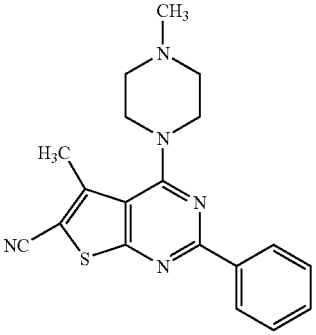

M.P. 223-225° C.; $^1$H-NMR (CDCl$_3$, 300 MHz) δ 8.48-8.40 (m, 3H), 7.49-7.46 (m, 3H), 3.69-3.63 (m, 4H), 2.72 (s, 3H), 2.66-2.62 (m, 4H), 2.38 (s, 3H); IR (KBr) 3416, 2969, 2921, 2212, 1532, 1445, 1402, 1377, 1360, 1326, 1298, 1172, 1141, 1063, 1027, 998, 861, 772, 705, 691, 680, 661 cm$^{-1}$.

Anal. Calcd. for $C_{19}H_{19}N_5S$ (349.454): C, 65.30; H, 5.48; N, 20.04. Found: C, 62.32; H, 5.27; N, 20.75. Yield=42%.

Example 51

5-Methyl-4-morpholin-4-yl-2-(3,4,5-trimethoxy-phenyl)-thieno[2,3-d]pyrimidine-6-carbonitrile

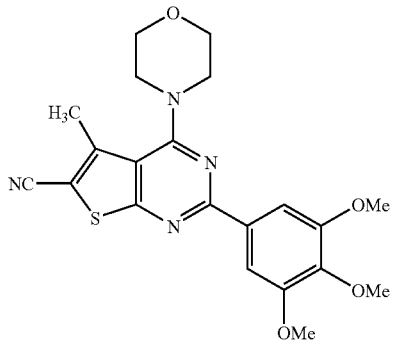

M.P.>250° C.; $^1$H-NMR (CDCl$_3$, 300 MHz) δ 7.76 (s, 2H), 3.97 (s, 6H), 3.92 (s, 3H), 3.91-3.88 (m, 4H), 3.59-3.56 (m, 4H), 2.73 (s, 3H); IR (KBr) 3391, 2922, 2846, 2359, 2209, 1592, 1291, 1225, 1156, 986, 792, 733 cm$^{-1}$. Anal. Calcd. for $C_{21}H_{22}N_4O_4S$ (426.490): C, 59.14; H, 5.20; N, 13.14. Found: C, 56.47; H, 5.96; N, 13.72. Yield=55%

Example 52

4-[(2-Hydroxy-ethyl)-methyl-amino]-5-methyl-2-(3,4,5-trimethoxy-phenyl)-thieno[2,3-d]pyrimidine-6-carbonitrile

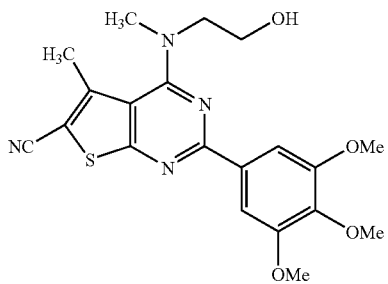

M.P. 164-166° C.; $^1$H-NMR (CDCl$_3$, 300 MHz) δ 7.68 (s, 2H), 3.99 (t, J=4.64 Hz, 2H), 3.96 (s, 6H), 3.90 (s, 3H), 3.88 (t, J=4.64 Hz, 2H), 2.72 (s, 3H); IR (KBr) 3513, 2935, 2210, 2203, 1692, 1591, 1538, 1501, 1463, 1391, 1224, 1004, 925, 789, 717 cm$^{-1}$. Anal. Calcd. for $C_{20}H_{22}N_4O_4S$ (414.479): C, 57.96; H, 5.35; N, 13.52. Found: C, 58.96; H, 5.96; N, 13.72. Yield=19%.

Example 53

2-3,5-Dimethoxy-phenyl)-5-methyl-4-(4-methyl-piperazin-1-yl)-thieno[2,3-d]pyrimidine-6-carbonitrile

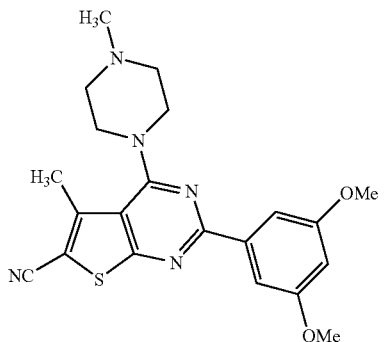

$^1$H-NMR (CDCl$_3$, 300 MHz) δ 7.64 (s, 2H), 6.59 (d, 1H), 3.87 (s, 6H), 3.61 (bs, 4H), 2.71 (s, 3H), 2.59 (bs, 4H), 2.34 (s, 3H); IR (KBr) 3440, 2938, 2210, 1740, 1591, 1534, 1150, 792 cm$^{-1}$. Anal. Calcd. for $C_{21}H_{23}N_5O_2S$ (409.506): C, 61.59; H, 5.66; N, 17.10. Found: C, 61.05; H, 5.78; N, 17.78. Yield=42%.

Example 54

4-Diethylamino-2-(3,5-dimethoxy-phenyl)-5-methyl-thieno[2,3-d]pyrimidine-6-carbonitrile

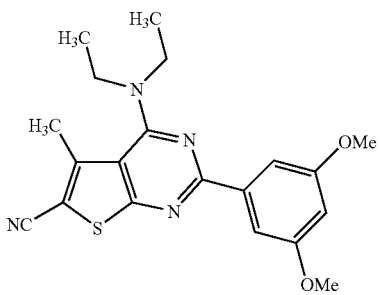

$^1$H-NMR (CDCl$_3$, 300 MHz) δ 7.64 (s, J=2.3 Hz, 2H), 6.58 (t, J=2.3 Hz, 1H), 3.87 (s, 6H), 3.59 (c, J=6.9 Hz, 4H), 2.69 (s, 3H), 1.23 (t, J=6.9 Hz, 6H); IR (KBr) 3399, 2976, 2934, 2211, 1522, 1442, 1199, 1067, 738 cm$^{-1}$. Anal. Calcd. for $C_{20}H_{22}N_4O_2S$ (382.480): C, 62.80; H, 5.80; N, 14.65. Found: C, 62.36; H, 5.87; N, 14.82. Yield=44%.

Example 55

2-(3,5-Dimethoxy-phenyl)-4-(ethyl-methyl-amino)-5-methyl-thieno[2,3-d]pyrimidine-6-carbonitrile

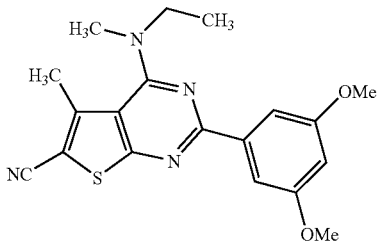

M.P. 145-148° C.; $^1$H-NMR (CDCl$_3$, 300 MHz) δ 7.65 (d, J=2.34 Hz, 2H), 6.59 (t, J=2.34 Hz, 1H), 3.88 (s, 6H), 3.64 (dd, J=7.04 Hz, 4.07 Hz, 2H), 3.14 (s, 3H), 2.70 (s, 3H), 1.31 (t, J=7.04 Hz, 3H); IR NaCl ($v_{max}$) 2210, 1521, 1497, 1442, 1391, 1202, 1064 cm$^{-1}$. Anal. Calcd. for $C_{19}H_{20}N_4O_2S$ (368.454): C, 61.94; H, 5.47; N, 15.21. Found: C, 61.04; H, 5.64; N, 15.85. Yield=50%.

Example 56

4-(6-Cyano-4-diethylamino-5-methyl-thieno[2,3-d]pyrimidin-2-yl)-benzoic acid methyl ester

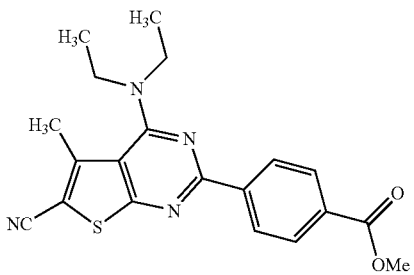

¹H-NMR (CDCl₃, 300 MHz) δ 8.49 (d, J=8.2 Hz, 2H), 8.11 (d, J=8.2 Hz, 2H), 3.94 (s, 3H), 3.63 (c, J=7.2 Hz, 4H), 2.71 (s, 3H), 1.25 (t, J=7.2 Hz, 6H). IR (KBr) 3393, 3295, 2213, 1714, 1531, 1274, 1017, 717 cm⁻¹. Anal. Calcd. for $C_{20}H_{20}N_4O_2S$ (380.465): C, 63.14; H, 5.30; N, 14.73. Found: C, 60.89; H, 5.47; N, 14.39. Yield=24%.

Example 57

4-[6-Cyano-4-ethyl-methyl-amino)-5-methyl-thieno[2,3d]pyrimidin-2-yl]-benzoic acid methyl ester

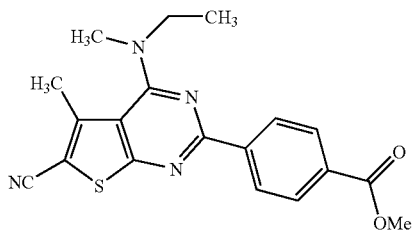

M.P. 125-128° C.; ¹H-NMR (CDCl₃, 300 MHz) δ 8.51 (d, J=8.35 Hz, 2H), 8.10 (d, J=8.35 Hz, 2H), 3.94 (s, 3H), 3.67 (dd, J=14.22 Hz, 7.18 Hz, 2H), 3.16 (s, 3H), 1.35 (t, J=14.22 Hz, 3H); IR (KBr) 2211, 1721, 1643, 1536, 1496, 1277, 1103, 1015, 719 cm⁻¹. Anal. Calcd. for $C_{19}H_{18}N_4O_2S$ (366.438): C, 62.28; H, 4.95; N, 15.29. Found: C, 59.28; H, 5.13; N, 15.22. Yield=57%.

Example 58

2-Benzyl-5-methyl-4-morpholin-4-yl-thieno[2,3-d]pyrimidine-6-carbonitrile

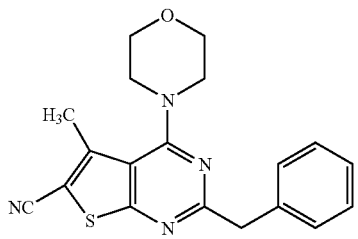

M.P. 88-90° C.; ¹H-NMR (CDCl₃, 300 MHz) δ 7.38-7.35 (m, 2H), 7.30-7.25 (m, 2H), 7.22-7.17 (m, 1H), 4.16 (s, 2H), 3.80-3.76 (m, 4H), 3.51-3.47 (m, 4H), 2.65 (s, 3H); IR (KBr) 3385, 3061, 3028, 2963, 2498, 1532, 1298, 1093, 997, 861, 798, 696 cm⁻¹. Anal. Calcd. for $C_{19}H_{18}N_4OS$ (350.439): C, 65.12; H, 5.18; N, 15.99. Found: C, 63.16; H, 5.47; N, 15.39. Yield=59%.

Example 59

2-Benzyl-4-[(2-hydroxy-ethyl)-methyl-amino]-5-methyl-thieno[2,3-d]pyrimidine-6-carbonitrile

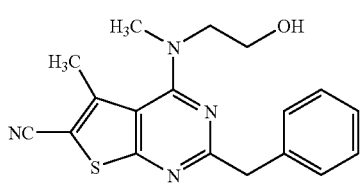

¹H-NMR δ 7.42-7.30 (m, 4H), 7.27-7.23 (m, 1H), 4.15 (s, 2H), 3.89 (t, J=4.64 Hz, 2H), 3.76 (t, J=4.64 Hz, 2H), 3.19 (s, 3H), 2.69 (s, 3H); IR (KBr) 3401, 3085, 3028, 2924, 1503, 1257, 1074, 1029, 800, 784, 695 cm⁻¹. Anal. Calcd. for $C_{18}H_{18}N_4OS$ (338.428): C, 63.88; H, 5.36; N, 16.56. Found: C, 63.32; H, 5.05; N, 16.55. Yield=43%.

Example 60

5-Methyl-4-(4-methyl-piperazin-1-yl)-2-3,4,5-trimethoxy-phenyl)-thieno[2,3-d]pyrimidine-4-carbonitrile

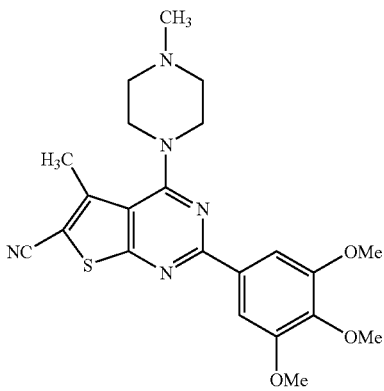

¹H-NMR (CDCl₃, 300 MHz) δ 7.77 (s, 2H), 3.98 (s, 6H), 3.92 (s, 3H), 3.65-3.62 (m, 4H), 2.73 (s, 3H), 2.68-2.63 (m, 4H), 2.39 (s, 3H); IR (KBr) 3384, 2925, 2851, 2360, 1733, 1590, 1507, 1259, 1124, 998, 779 cm⁻¹. $C_{22}H_{25}N_5O_3S$ (439.532). Yield=75%.

Example 61

Methyl 4-(6-cyano-6-methyl-4-morpholin-4-ylthieno[2,3-d]pyrimidin-2-yl)benzoate

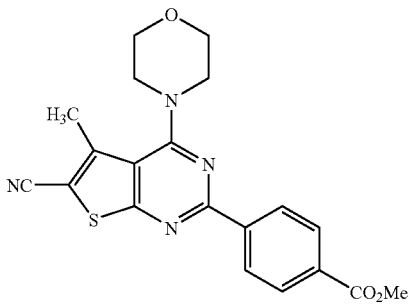

¹H-NMR (CDCl₃, 200 MHz): δ (ppm) 8.52 (d, J=8.3 Hz, 2H), 8.13 (d, J=8.3 Hz, 2H), 3.94 (s, 3H), 3.93-3.88 (m, 4H), 3.65-3.60 (m, 4H), 2.74 (s, 3H). Yield=75%.

Example 62

Methyl 4-[6-cyano-5-methyl-4-(4-methylpiperazin-1-yl)thieno[2,3-d]pyrimidin-2-yl]benzoate

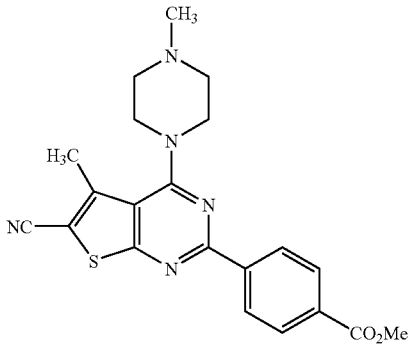

¹H-NMR (CDCl₃, 300 MHz): δ (ppm) 8.46 (d, J=7.1 Hz, 2H), 8.24 (d, J=7.1 Hz, 2H), 3.95 (s, 3H), 3.62 (bs, 4H), 2.78

Example 63

Methyl 4-[6-cyano-4-(dimethylamino)-5-methylthieno[2,3-d]pyrimidin-2-yl]benzoate

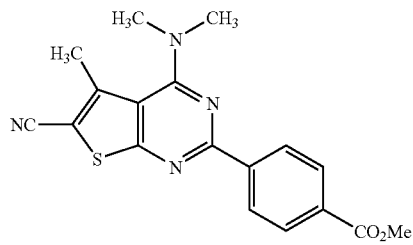

$^1$H-NMR (CDCl$_3$, 300 MHz): δ (ppm) 8.55 (d, J=8.5 Hz, 2H), 8.14 (d, J=8.5 Hz, 2H), 3.96 (s, 3H), 3.23 (s, 6H), 2.75 (s, 3H). IR (KBr): ν$_{máx}$ (cm$^{-1}$) 2360, 2341, 2211, 1719, 1540, 1519, 1497, 1276. Yield=82%.

Example 64

Methyl 4-{6-cyano-4-[(2-hydroxyethyl)(methyl)amino]-5-methylthieno[2,3-d]pyrimidin-2-yl}benzoate

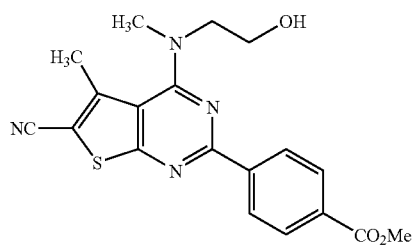

$^1$H-NMR (CDCl$_3$, 300 MHz): δ (ppm) 8.43 (d, J=8.4 Hz, 2H), 8.10 (d, J=8.4 Hz, 2H), 4.02-3.98 (m, 2H), 3.93 (s, 3H), 3.94-3.84 (m, 2H), 3.25 (s, 3H), 2.72 (s, 3H). Yield=40%.

Example 65

5-methyl-4-(methylamino)-2-(3,4,5-trimethoxyphenyl)thieno[2,3-d]pyrimidine-6-carbonitrile

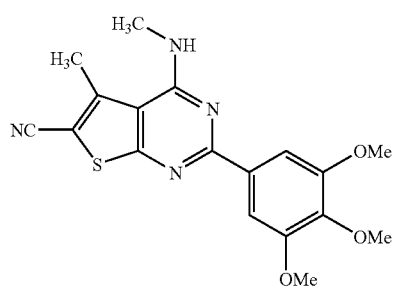

$^1$H-NMR (CDCl$_3$, 300 MHz): δ (ppm) 7.79 (s, 2H), 5.52 (bs, 1H), 3.97 (s, 6H), 3.91 (s, 3H), 3.28 (d, J=4.8 Hz, 3H), 2.77 (s, 3H). IR (KBr): ν$_{máx}$ (cm$^{-1}$) 3439, 2923, 2852, 1728, 1576, 1128, 788. Yield=13%.

Example 66

4-(Dimethylamino)-5-methyl-2-(3,4,5-trimethoxyphenyl)thieno[2,3-d]pyrimidine-6-carbonitrile

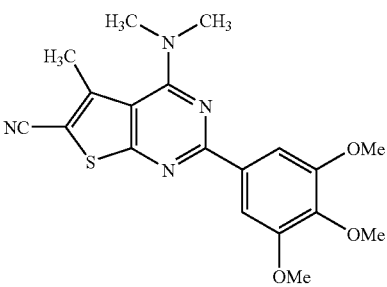

$^1$H-NMR (CDCl$_3$, 300 MHz): δ (ppm) 7.79 (s, 2H), 3.99 (s, 6H), 3.93 (s, 3H), 3.20 (s, 6H), 2.74 (s, 3H). IR (KBr): vmáx (cm$^{-1}$) 2951, 2928, 2206, 1542, 1503, 1464, 1384, 1340, 1220, 1127, 997. Yield=81%.

Example 67

4-Ethylamino)-5-methyl-2-(3,4,5-trimethoxyphenyl)thieno[2,3-d]pyrimidine-6-carbonitrile

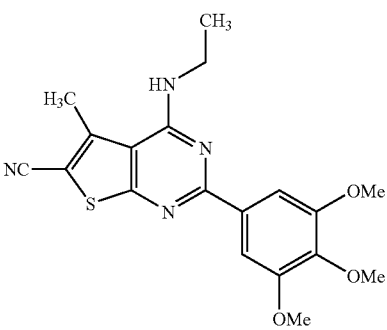

$^1$H-NMR (CDCl$_3$, 300 MHz): δ (ppm) 7.77 (s, 2H), 5.40 (bs, 1H), 3.97 (s, 6H), 3.91 (s, 3H), 3.79-3.75 (m, 2H), 2.77 (s, 3H), 1.39 (t, J=7.1 Hz, 3H). IR (KBr): ν$_{máx}$ (cm$^{-1}$) 3443, 2955, 2207, 1575, 1400, 1344, 1127, 788. Yield=52%.

Example 68

5-Methyl-4-(propylamino)-2-3,4,5-trimethoxyphenyl)thieno[2,3-d]pyrimidine-6-carbonitrile

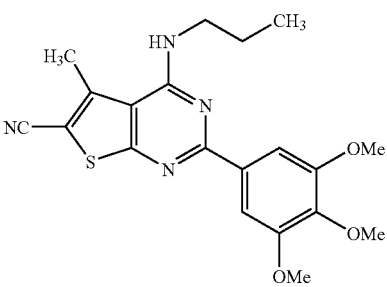

$^1$H-NMR (CDCl$_3$, 300 MHz): δ (ppm) 7.79 (s, 2H), 5.63 (m, 1H), 3.99 (s, 6H), 3.93 (s, 3H), 3.72 (m, 2H), 2.79 (s, 3H), 1.82 (m, 2H), 1.08 (t, J=7.4 Hz, 3H). IR (KBr): ν$_{máx}$ (cm$^{-1}$) 3594, 3526, 2957, 2211, 1508, 11224, 1126. HPLC-MS (API-ES+, m/z) 399.1 (M+1)$^+$. Yield=77%.

(From previous page continuation:)
(s, 3H), 2.60 (bs, 4H), 2.42 (s, 3H). IR (KBr): ν$_{máx}$ (cm$^{-1}$) 3395, 2925, 2209, 1719, 1536, 1324, 11183, 719. Yield=45%.

Example 69

4-(Butylamino)-5-methyl-2-(3,4,5-trimethoxyphenyl)thieno[2,3-d]pyrimidine-6-carbonitrile

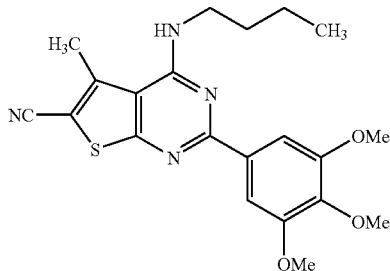

M.P.: 192-194° C.; $^1$H-NMR (CDCl$_3$, 300 MHz): δ (ppm) 7.79 (s, 2H), 5.60 (bs, 1H), 3.99 (s, 6H), 3.93 (s, 3H), 3.76 (m, 2H), 2.78 (s, 3H), 1.77 (m, 2H), 1.52 (m, 2H), 1.02 (t, J=7.2 Hz, 3H). IR (KBr): ν$_{máx}$ (cm$^{-1}$) 3428, 2955, 2872, 2212, 1222, 1174, 1129, 1088, 731, 722. HPLC-MS (API-ES+, m/z) 413.0 (M+1)$^+$. Yield=75%.

Example 70

4-(Isopropylamino)-5-methyl-2-(3,4,5-trimethoxyphenyl)thieno[2,3-d]pyrimidine-6-carbonitrile

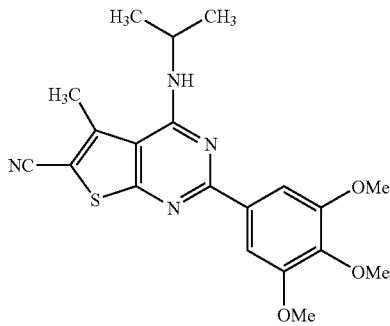

M.P. 191-193° C. $^1$H-NMR (CDCl$_3$, 300 MHz): δ (ppm) 7.76 (s, 2H), 5.36 (bs, 1H), 4.58-4.43 (m, 1H), 3.97 (s, 6H), 3.91 (s, 3H), 2.76 (s, 3H), 1.32 (d, J=5.9 Hz, 6H). IR (KBr): ν$_{máx}$ (cm$^{-1}$) 3444, 2969, 2933, 2212, 1551, 1399, 1128. HPLC-MS (API-ES+, m/z) 399.1 (M+1)$^+$. Yield=75%.

Example 71

4-(sec-Butylamino)-5-methyl-2-(3,4,5-trimethoxyphenyl)thieno[2,3-d]pyrimidine-6-carbonitrile

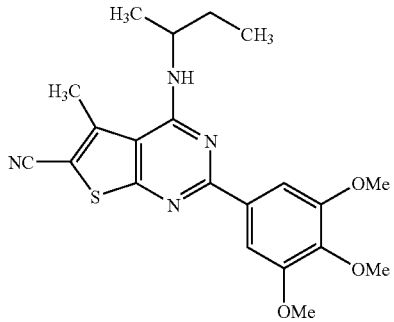

M.P.: 91-93° C. $^1$H-NMR (CDCl$_3$, 300 MHz): δ (ppm) 7.76 (s, 2H), 5.35 (d, J=6.9 Hz, 1H), 4.47-4.41 (m, 1H), 3.97 (s, 6H), 3.91 (s, 3H), 2.76 (s, 3H), 1.80-1.73 (m, 2H), 1.36 (d, J=6.4 Hz, 3H), 1.03 (t, J=7.4 Hz, 3H). IR (KBr): ν$_{máx}$ (cm$^{-1}$) 3464, 2962, 2832, 2205, 1553, 1398, 1343, 1133, 1006, 789, 732. HPLC-MS (API-ES+, m/z) 413.1 (M+1)$^+$. Yield=41%.

Example 72

4-(Isobutylamino)-5-methyl-2-(3,4,5-trimethoxyphenyl)thieno[2,3-d]pyrimidine-6-carbonitrile

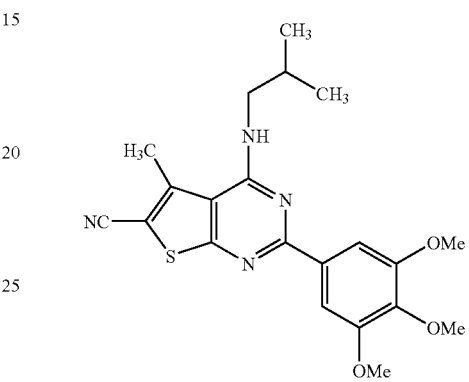

M.P.: 182-184° C.; $^1$H-NMR (CDCl$_3$, 300 MHz): δ (ppm) 7.76 (s, 2H), 5.67 (t, J=5.4 Hz, 1H), 3.97 (s, 6H), 3.90 (s, 3H), 3.55 (t, J=6.2 Hz, 2H), 2.76 (s, 3H), 2.12 (m, 1H), 1.03 (d, J=6.9 Hz, 6H). IR (KBr): ν$_{m\ áx}$ (cm$^{-1}$) 3447, 3431, 2952, 2210, 1551, 1507, 1084, 789, 731. HPLC-MS (API-ES+, m/z) 413.3 (M+1)$^+$. Yield=95%.

Example 73

4-[(1-Ethylpropyl)amino]-5-methyl-2-(3,4,5-trimethoxyphenyl)thieno[2,3-d]pyrimidine-6-carbonitrile

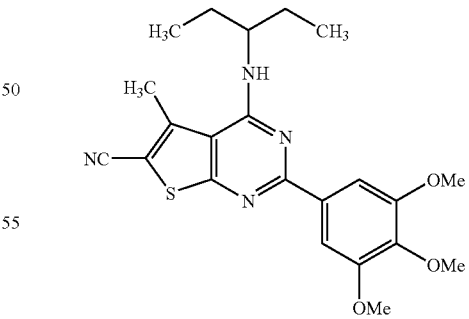

M.P.: 226-228° C.; $^1$H-NMR (CDCl$_3$, 300 MHz): δ (ppm) 7.76 (s, 2H), 5.33 (d, J=7.6 Hz, 1H), 4.36-4.33 (m, 1H), 3.97 (s, 6H), 3.96 (s, 3H), 2.76 (s, 3H), 1.78-1.53 (m, 4H), 1.01 (t, J=7.4 Hz, 6H). IR (KBr): ν$_{máx}$ (cm$^{-1}$) 3465, 2965, 2205, 1553, 1507, 1398, 1132, 1005, 789, 617. HPLC-MS (API-ES+, m/z) 427.1 (M+1)$^+$. Yield=67%.

Example 74

4-(tert-Butylamino)-5-methyl-2-(3,4,5-trimethoxyphenyl)thieno[2,3-d]pyrimidine-6-carbonitrile

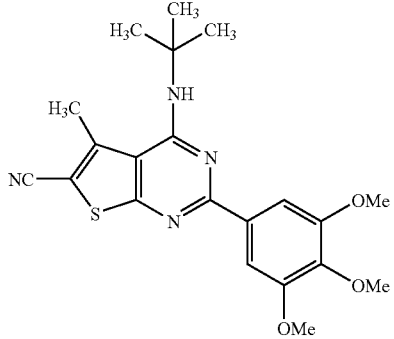

M.P.: 195-197° C.; $^1$H-NMR (CDCl$_3$, 300 MHz): δ (ppm) 7.77 (s, 2H), 5.51 (bs, 1H), 3.97 (s, 6H), 3.92 (s, 3H), 2.75 (s, 3H), 1.64 (s, 9H). IR (KBr): ν$_{máx}$ (cm$^{-1}$) 3468, 2952, 2209, 1553, 1508, 1401, 1129, 1009, 789, 731. HPLC-MS (API-ES+, m/z) 413.2 (M+1)$^+$. Yield=75%.

Example 75

4-(Cyclopropylamino)-5-methyl-2-(3,4,5-trimethoxyphenyl)thieno[2,3-d]pyrimidine-6-carbonitrile

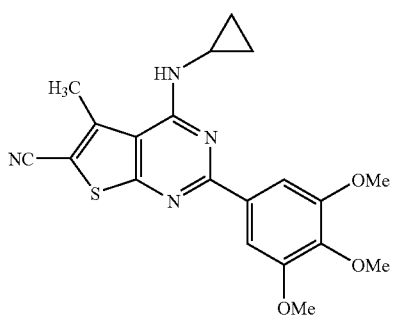

$^1$H-NMR (CDCl$_3$, 300 MHz): δ (ppm) 7.86 (s, 2H), 5.75 (s, 1H), 3.97 (s, 6H), 3.39 (s, 3H), 3.06 (m. 1H), 2.73 (s, 3H), 0.99 (dd, J=6.6 Hz, 2H), 0.72 (dd, J=6.6 Hz, 2H). IR (KBr): ν$_{máx}$ (cm$^{-1}$) 2209, 1556, 1505, 1445, 1400, 1342, 1233, 1176, 1131, 865, 789, 732. Yield=55%;

Example 76

4-Cyclobutylamino)-5-methyl-2-(3,4,5-trimethoxyphenyl)thieno[2,3-d]pyrimidine-6-carbonitrile

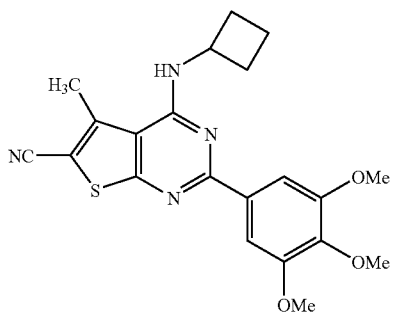

$^1$H-NMR (CDCl$_3$, 300 MHz): δ (ppm) 7.78 (s, 2H), 5.63 (d, J=5.5 Hz, 1H), 4.75 (m, 1H), 3.99 (s, 6H), 3.92 (s, 3H), 2.78 (s, 3H), 2.58 (m, 2H), 2.04 (m, 2H), 1.94 (m, 2H). IR (KBr): ν$_{máx}$ (cm$^{-1}$) 2350, 2202, 1565, 1505, 1447, 1399, 1341, 1125, 859, 787. Yield=55%.

Example 77

4-(Cyclopentylamino)-5-methyl-2-(3,4,5-trimethoxyphenyl)thieno[2,3-d]pyrimidine-6-carbonitrile

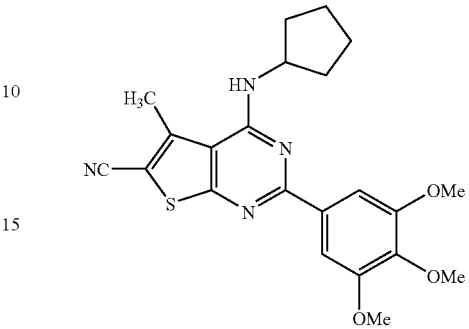

M.P.: 218-220° C.; $^1$H-NMR (CDCl$_3$, 300 MHz): δ (ppm) 7.78 (s, 2H), 5.50 (d, J=6.0 Hz, 1H), 4.67-4.60 (m, 1H), 3.96 (s, 6H), 3.90 (s, 3H), 2.74 (s, 3H), 2.40.22 (m, 2H), 1.77-1.49 (m, 6H). IR (KBr): ν$_{máx}$ (cm$^-$) 3477, 2962, 2936, 2866, 2070, 1553, 1372, 1125, 790, 732. HPLC-MS (API-ES+, m/z) 425.1 (M+1)$^+$. Yield=63%.

Example 78

4-[Allyl(methyl)amino]-5-methyl-2-(3,4,5-trimethoxyphenyl)thieno[2,3-d]pyrimidine-6-carbonitrile

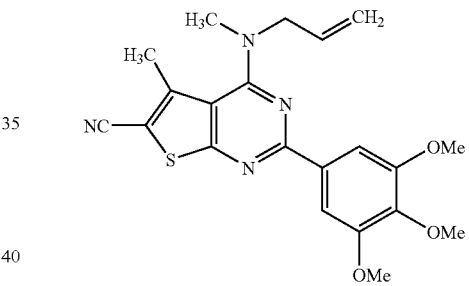

M.P.: 162-164° C.; $^1$H-NMR (CDCl$_3$, 200 MHz): δ (ppm) 7.75 (s, 2H), 6.10-5.92 (m, 1H), 5.38-5.33 (m, 2H), 4.19-4.16 (m, 2H), 3.96 (s, 6H), 3.90 (s, 3H), 3.11 (s, 3H), 2.71 (s, 3H). IR (KBr): ν$_{máx}$ (cm$^{-1}$) 3365, 2361, 1728, 1536, 1133, 1007, 784. Yield=38%.

Example 79

5-Methyl-4-[methyl(prop-2-ynyl)amino]-2-3,4,5-trimethoxyphenyl)thieno[2,3-d]pyrimidine-6-carbonitrile

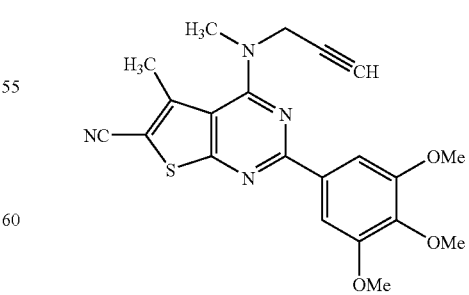

$^1$H-NMR (CDCl$_3$, 200 MHz): δ (ppm) 7.83 (s, 2H), 4.28 (bs, 2H), 3.97 (s, 6H), 3.91 (s, 3H), 3.21 (s, 3H), 2.75 (s, 3H), 2.33 (bs, 1H). IR (KBr): ν$_{máx}$ (cm$^{-1}$) 3293, 3246, 2993, 2939, 2826, 2359, 2212, 1537, 1462, 733. Yield=42%.

Example 80

4-[(2-Hydroxyethyl)amino]-5-methyl-2-(3,4,5-tri-methoxyphenyl)thieno[2,3-d]pyrimidine-6-carbonitrile

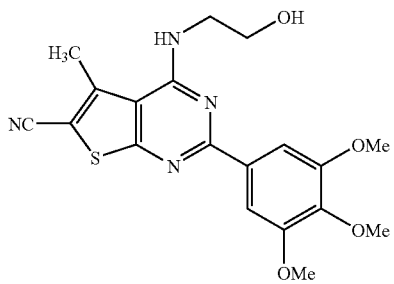

$^1$H-NMR (CDCl$_3$, 200 MHz): δ (ppm) 7.71 (s, 2H), 6.10 (bs, 1H), 3.97 (s, 6H), 3.96-3.91 (m, 4H), 3.91 (s, 3H), 2.78 (s, 3H). IR (KBr): ν$_{máx}$ (cm$^{-1}$) 3494, 3453, 2212, 1651, 1582, 1556, 1511, 1222, 1180, 735. HPLC-MS (API-ES+, m/z) 401.1 (M+1)$^+$. Yield=43%.

Example 81

4-[2-Methoxyethyl)amino]-5-methyl-2-3,4,5-tri-methoxyphenyl)thieno[2,3-d]pyrimidine-6-carbonitrile

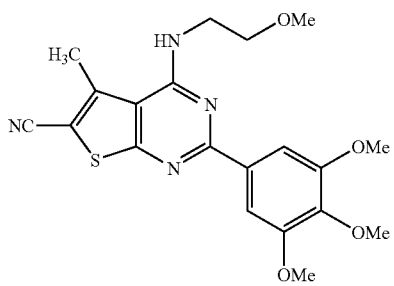

$^1$H-NMR (CDCl$_3$; 200 MHz): δ (ppm) 7.74 (s, 2H), 6.02 (ta, 1H), 3.96 (s, 6H), 3.94-3.88 (m, 2H), 3.90 (s, 3H), 3.68 (t, J=5.0 Hz, 2H), 3.43 (s, 3H), 2.75 (s, 3H). IR (KBr): ν$_{máx}$ (cm$^{-1}$) 3500, 3406, 2924, 2205, 1715, 1569, 1555, 1511, 1447, 1224, 730. HPLC-MS (API-ES+, m/z) 415.1 (M+1)$^+$. Yield=42%.

Example 82

4-{[2-(Dimethylamino)ethyl]amino}-5-methyl-2-(3,4,5-trimethoxyphenyl)thieno[2,3-d]pyrimidine-6-carbonitrile

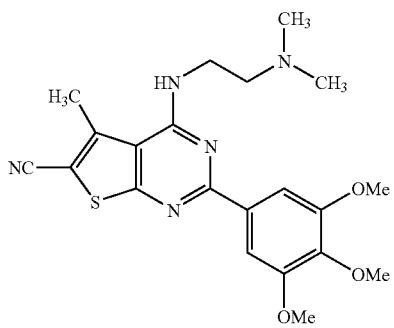

$^1$H-NMR (CDCl$_3$, 200 MHz): δ (ppm) 7.73 (s, 2H), 6.72 (bs, 1H), 3.98 (s, 6H), 3.94 (s, 3H), 3.72 (m, 2H), 2.75 (s, 3H), 2.65 (bs, 2H), 2.34 (s, 6H). IR (KBr): ν$_{máx}$ (cm$^{-1}$) 3429, 2943, 2825, 2773, 2360, 2341, 2209, 1570, 1508, 1448, 1223, 1127, 732. HPLC-MS (API-ES+, m/z) 426.1 (M+1)$^+$. Yield=36%.

Example 83

5-Methyl-4-(3-methylpiperazin-1-yl)-2-(3,4,5-tri-methoxyphenyl)thieno[2,3-d]pyrimidine-6-carbonitrile

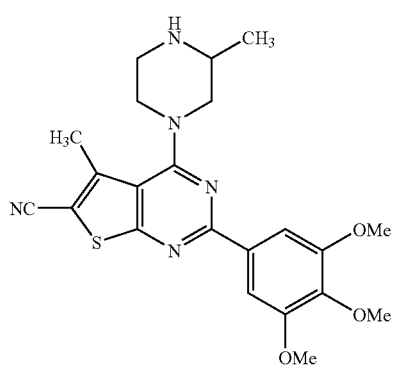

M.P.: 213-215° C.; $^1$H-NMR (CDCl$_3$, 200 MHz): δ (ppm) 7.75 (s, 2H), 3.96 (s, 6H), 3.90 (s, 3H), 3.88 (da, 1H), 3.25 (td, J=11.0 y 3.5 Hz, 1H), 3.09 (m, 3H), 2.82 (dd, J=12.6 y 10.6 Hz, 1H), 2.70 (s, 3H), 1.11 (d, J=6.2 Hz, 3H). IR (KBr): ν$_{máx}$ (cm$^{-1}$) 2209, 1533, 1498, 1394, 1344, 1223, 1126, 1005, 733. HPLC-MS (API-ES+, m/z) 440.2 (M+1)$^+$. Yield=44

Example 84

4-(3,5-Dimethylpiperazin-1-yl)-5-methyl-2-(3,4,6-trimethoxyphenyl)thieno[2,3-d]pyrimidine-6-carbonitrile

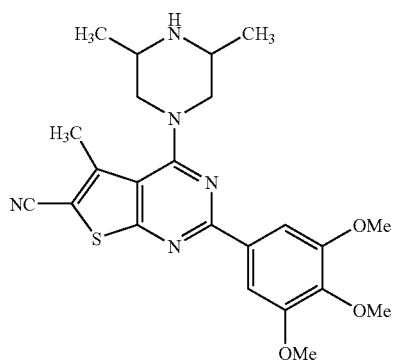

M.P.: 186-188° C.; $^1$H-NMR (CDCl$_3$, 200 MHz): δ (ppm) 7.75 (s, 2H), 4.04 (s, 6H), 3.96 (s, 3H), 3.89 (s, 1H), 3.87 (s, 1H), 3.12 (bs, 2H), 2.82 (t, J=11 Hz, 2H), 2.69 (s, 3H), 1.12 (d, J=6.2 Hz, 6H). IR (KBr): ν$_{máx}$ (cm$^{-1}$) 3321, 2961, 2933, 2831, 2212, 1591, 1395, 1126, 1005, 861, 786, 717. HPLC-MS (API-ES+, m/z) 454.2 (M+1)$^+$. Yield=17%.

Example 85

4-(4-Acetylpiperazin-1-yl)-5-methyl-2-(3,4,5-trimethoxyphenyl)thieno[2,3-d]pyrimidine-6-carbonitrile

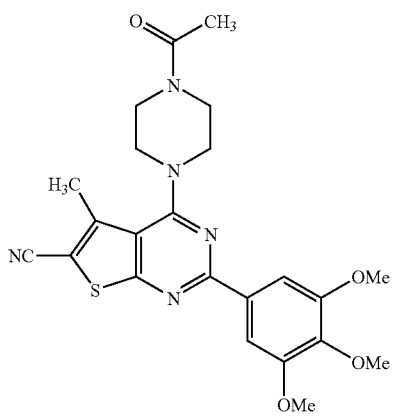

M.P.: 211-213° C.; $^1$H-NMR (CDCl$_3$, 200 MHz): δ (ppm) 7.75 (s, 2H), 3.97 (s, 6H), 3.92 (s, 3H), 3.69 (bs, 2H), 3.59 (bs, 2H), 3.55 (bs, 2H), 3.54 (bs, 2H), 2.74 (s, 3H), 2.16 (s, 3H). IR (KBr): ν$_{máx}$ (cm$^{-1}$) 3433, 2914, 2211, 1639, 1535, 1432, 1258, 1132, 998, 792. Yield=53%.

Example 86

4-[(2-Aminoethyl)(methyl)amino]-5-methyl-2-(3,4,5-trimethoxyphenyl)thieno[2,3-d]pyrimidine-6-carbonitrile

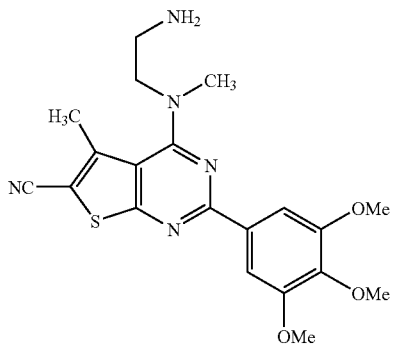

M.P.: >290° C.; $^1$H-NMR (CDCl$_3$, 300 MHz): δ (ppm) 7.78 (s, 2H), 6.68 (ta, 2H), 3.99 (s, 6H), 3.92 (s, 3H), 3.77 (ca, 2H), 2.97 (ta, 2H), 2.77 (s, 3H), 2.50 (s, 3H). IR (KBr): ν$_{máx}$ (cm$^{-1}$) 3427, 1575, 1506, 1446, 1396, 1221, 1126, 1001, 788, 668. HPLC-MS (API-ES+, m/z) 414.3 (M+1)$^+$. Yield=45%.

Example 87

N-[6-Cyano-5-methyl-2-(3,4,5-trimethoxyphenyl)thieno[2,3-d]pyrimidin-4-yl]-beta-alanine

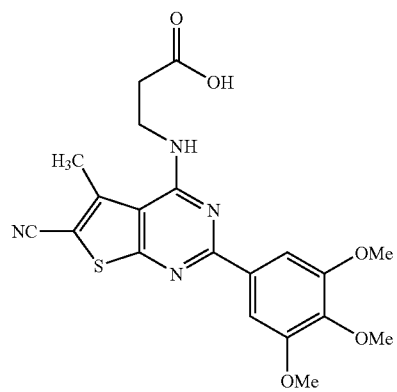

M.P.: 222-225° C.; $^1$H-NMR (CDCl$_3$, 200 MHz): δ (ppm) 7.79 (bs, 2H), 5.51 (bs, 4H), 3.95 (bs, 6H), 3.86 (bs, 3H), 2.79 (bs, 3H), 2.17 (bs, 1H). IR (KBr): ν$_{máx}$ (cm$^{-1}$) 3 440, 2947, 2211, 1713, 1551, 1400, 1126, 789, 733. HPLC-MS (API-ES+, m/z) 429.2 (M+1)$^+$. Yield=25%.

Example 88

5-Methyl-4-(1H-pyrazol-1-yl)-2-(3,4,5-trimethoxyphenyl)thieno[2,3-d]pyrimidine-6-carbonitrile

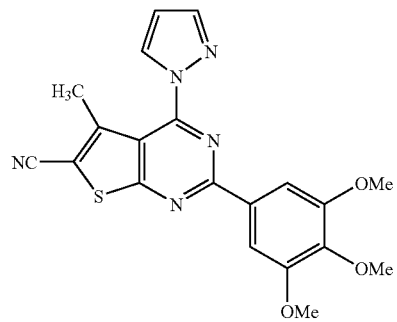

M.P.: 209-214° C.; $^1$H-NMR (CDCl$_3$, 200 MHz): δ (ppm) 8.52 (bs, 1H), 7.88 (bs, 1H), 7.80 (s, 2H), 6.62 (bs, 1H), 3.99 (s, 6H), 3.93 (s, 3H), 2.66 (s, 3H). IR (KBr): ν$_{máx}$ (cm$^{-1}$) 3433, 2934, 2836, 2216, 1520, 1492, 1235, 1225, 1185, 635. HPLC-MS (API-ES+, m/z) 408 (M+1)$^+$. Yield=66%.

Example 89

4-(1H-Imidazol-1-yl)-5-methyl-2-(3,4,5-trimethoxyphenyl)thieno[2,3-d]pyrimidine-6-carbonitrile

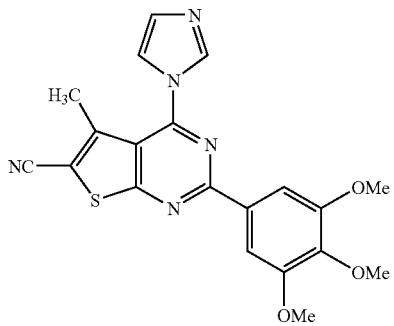

M.P.: 238-240° C.; $^1$H-NMR (CDCl$_3$, 200 MHz): δ (ppm) 8.04 (bs, 1H), 7.80 (s, 2H), 7.44 (bs, 1H), 7.34 (bs, 1H), 3.98 (s, 6H), 3.94 (s, 3H), 2.39 (s, 3H). IR (KBr): ν$_{máx}$ (cm$^{-1}$) 3425, 3123, 2933, 2218, 1556, 1408, 1128, 1004, 711. HPLC-MS (API-ES+, m/z) 408.1 (M+1)$^+$. Yield=33%;

Example 90

5-Methyl-4-(2H-1,2,3-triazol-2-yl)-2-(3,4,5-trimethoxyphenyl)thieno[2,3-d]pyrimidine-6-carbonitrile

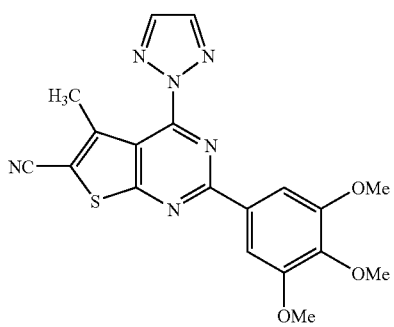

M.P.: 208-210° C.; $^1$H-NMR (CDCl$_3$, 200 MHz): δ (ppm) 8.05 (s, 2H), 7.82 (s, 2H), 3.97 (s, 6H), 3.92 (s, 3H), 2.31 (s, 3H). IR (KBr): ν$_{máx}$ (cm$^{-1}$) 3439, 2939, 2216, 1558, 1520, 1398, 1126, 1000, 839, 713. HPLC-MS (API-ES+, m/z) 409.1 (M+1)$^+$. Yield=32%.

Example 91

5-Methyl-4-(1H-1,2,4-triazol-1-yl)-2-(3,4,5-trimethoxyphenyl)thieno[2,3-d]pyrimidine-6-carbonitrile

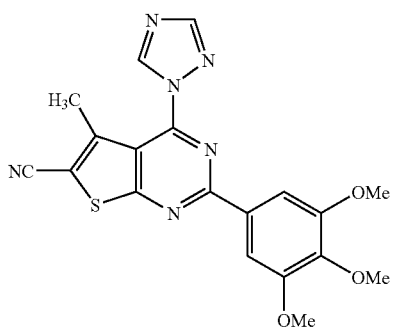

M.P.: 236-240° C.; $^1$H-NMR (CDCl$_3$, 300 MHz): δ (ppm) 9.11 (s, 1H), 8.25 (s, 1H), 7.78 (s, 2H), 3.98 (s, 6H), 3.94 (s, 3H), 2.63 (s, 3H). IR (KBr): ν$_{máx}$ (cm$^{-1}$) 3435, 2939, 2214, 1560, 1507, 1491, 1178, 1126. HPLC-MS (API-ES+, m/z) 409.2 (M+1)$^+$. Yield=60%.

Example 92

2-(3,4-Dimethoxybenzyl)-5-methyl-4-morpholin-4-ylthieno[2,3-d]pyrimidine-6-carbonitrile

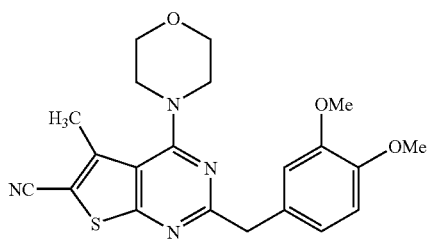

M.P.: 67-70° C.; $^1$H-NMR (CDCl$_3$, 300 MHz): δ (ppm) 6.95 (s, 1H), 6.91 (d, J=8.0 Hz, 1H), 6.77 (d, J=8.0 Hz, 1H), 4.09 (s, 2H), 3.85 (s, 3H), 3.82 (s, 3H), 3.81 (t, J=4.0 Hz, 4H), 3.49 (t, J=4.0 Hz, 4H). IR (KBr): ν$_{máx}$ (cm$^{-1}$) 2960, 2855, 2212, 1534, 1495, 1442, 730. HPLC-MS (API-ES+, m/z) 411.1 (M+1)$^+$. Yield=46%.

Example 93

2-3,4-Dimethoxybenzyl)-5-methyl-4-(4-methylpiperazin-1-yl)thieno[2,3-d]pyrimidine-6-carbonitrile

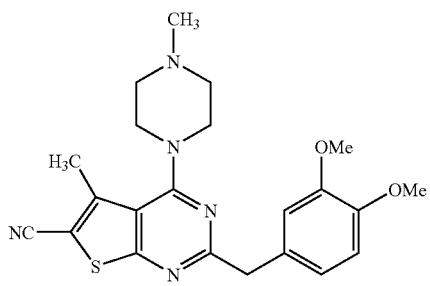

$^1$H-NMR (CDCl$_3$, 300 MHz): δ (ppm) 7.24-6.94 (m, 2H), 6.90-6.79 (m, 1H), 4.08 (s, 2H), 3.83 (d, J=4.8 Hz, 6H), 3.54-3.49 (m, 4H), 2.64 (s, 3H), 2.54-2.49 (m, 4H), 2.32 (s, 3H). IR (KBr): ν$_{máx}$ (cm$^{-1}$) 3435, 2935, 2839, 2791, 2211, 1534, 1261, 1140, 1028, 729. Yield=58%.

Example 94

2-(3,4-Dimethoxybenzyl)-5-methyl-4-(methylamino)thieno[2,3-d]pyrimidine-6-carbonitrile

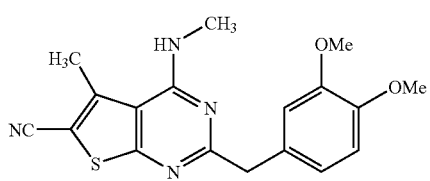

M.P.: 161-163° C.; $^1$H-NMR (CDCl$_3$, 300 MHz): δ (ppm) 7.00 (s, 1H), 6.94 (d, J=8.2 Hz, 1H), 6.77 (d, J=8.2 Hz, 1H), 5.45 (bs, 1H), 4.04 (s, 2H), 3.85 (s, 3H), 3.82 (s, 3H), 3.14 (d, J=4.9 Hz, 3H), 2.70 (s, 3H). IR (KBr): ν$_{máx}$ (cm$^{-1}$) 3416, 1926, 2212, 1676, 1578, 1512, 1230, 1026, 753. Yield=60%.

Example 95

2-(3,4-Dimethoxybenzyl)-4-(ethylamino)-5-methylthieno[2,3-d]pyrimidine-6-carbonitrile

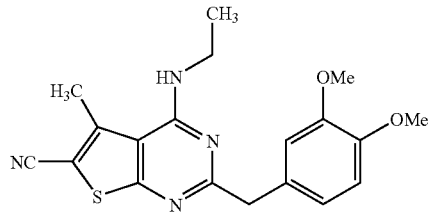

M.P.: 125-126° C.; $^1$H-NMR (CDCl$_3$, 300 MHz): δ (ppm) 7.23 (s, 1H), 6.95 (d, J=8.2 Hz, 1H), 6.77 (d, J=8.2 Hz, 1H), 5.44 (ta, 1H), 4.01 (s, 2H), 3.85 (s, 3H), 3.82 (s, 3H), 3.66-3.61 (m, 2H), 2.70 (s, 3H), 1.27 (t, J=7.3 Hz, 3H). IR (KBr): ν$_{máx}$ (cm$^{-1}$) 3436, 2931, 2214, 1577, 1506, 1445, 1398, 1270, 1025, 808, 765. Yield=48%.

Example 96

2-(3,4-Dimethoxybenzyl)-5-methyl-4-propylamino)thieno[2,3-d]pyrimidine-6-carbonitrile

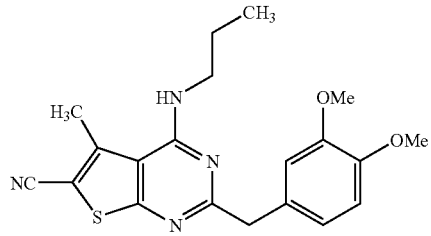

$^1$H-NMR (CDCl$_3$, 300 MHz): δ (ppm) 6.99 (s, 1H), 6.96 (d, J=7.9 Hz, 1H), 6.76 (s, J=7.9 Hz, 1H), 5.54 (bs, 1H), 4.04 (s, 2H), 3.87 (s, 3H), 3.85 (s, 3H), 3.60 (c, J=6.9 Hz, 2H), 2.73 (s, 3H), 1.68 (m, 2H), 1.00 (t, J=7.1 Hz, 3H). IR (KBr): ν$_{máx}$ (cm$^{-1}$) 3433, 2961, 2210, 1572, 1549, 1508, 1448, 1260, 1234, 1154, 1028, 731, 559. HPLC-MS (API-ES+, m/z) 383.1 (M+1)$^+$. Yield=85%.

Example 97

4-(Cyclopropylamino)-2-(3,4-dimethoxybenzyl)-5-methylthieno[2,3-d]pyrimidine-6-carbonitrile

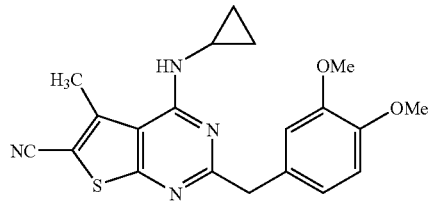

$^1$H-NMR (CDCl$_3$, 300 MHz): δ (ppm) 7.00 (s, 1H), 6.97 (d, J=8.0 Hz, 1H), 6.77 (d, J=8.0 Hz, 1H), 5.63 (bs, 1H), 4.05 (s, 2H), 3.84 (s, 3H), 3.82 (s, 3H), 2.96 (m, 1H), 2.64 (s, 3H), 0.89 (m, 2H), 0.56 (m, 2H). IR (KBr): ν$_{máx}$ (cm$^{-1}$) 3433, 2961, 2210, 1572, 1549, 1508, 1448, 1260, 1234, 1154, 1028, 731, 559. HPLC-MS(API-ES+, m/z) 388.1 (M+1)$^+$. Yield=83%.

Example 98

4-(Cyclobutylamino)-2-(3,4-dimethoxybenzyl)-5-methylthieno[2,3-d]pyrimidine-6-carbonitrile

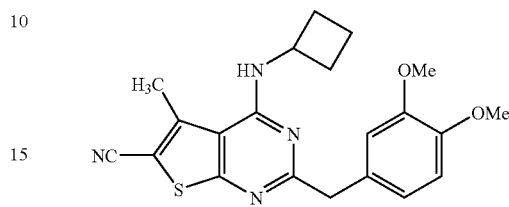

$^1$H-NMR (CDCl$_3$, 300 MHz): δ (ppm) 6.95 (s, 1H), 6.91 (d, J=8.0 Hz, 1H), 6.76 (d, J=8.0 Hz, 1H), 5.55 (d, J=6.22 Hz, 1H), 4.67 (m, 1H), 4.00 (s, 2H), 3.85 (s, 3H), 3.82 (s, 3H), 2.70 (s, 3H), 2.44 (m, 2H), 1.85 (m, 4H). IR (KBr): ν$_{máx}$ (cm$^{-1}$) 3428, 2939, 2211, 1568, 1547, 1260, 1234, 731. HPLC-MS (API-ES+, m/z) 395.1 (M+1)$^+$. Yield=80%.

Example 99

2-(3,4-Dimethoxybenzyl)-4-(dimethylamino)-5-methylthieno[2,3-d]pyrimidine-6-carbonitrile

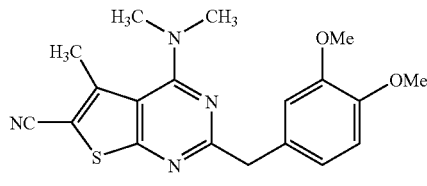

$^1$H-NMR (CDCl$_3$, 300 MHz): δ (ppm) 6.99 (s, 1H), 6.97 (d, J=8.2 Hz, 1H), 6.77 (d, J=8.2 Hz, 1 H), 4.05 (s, 2H), 3.85 (s, 3H), 3.82 (s, 3H), 3.08 (s, 6H), 2.64 (s, 3H). IR (KBr): ν$_{máx}$ (cm$^{-1}$) 2998, 2955, 2933, 2834, 2211, 1513, 1261, 1234, 1155, 1027. HPLC-MS (API-ES+, m/z) 369.1 (M+1)$^+$. Yield=84%.

Example 100

2-(3,4-Dimethoxybenzyl)-4-[ethyl(methyl)amino]-5-methylthieno[2,3-d]pyrimidine-6-carbonitrile

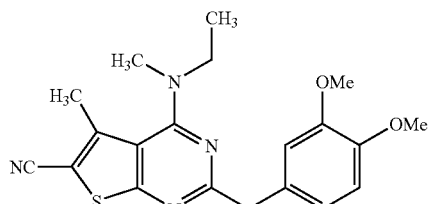

$^1$H-NMR (CDCl$_3$, 300 MHz): δ (ppm) 6.97 (d, J=1.8 Hz, 1H), 6.92 (dd, J=7.9 Hz y 1.8 Hz, 1H), 6.76 (d, J=7.9 Hz, 1H), 4.04 (s, 2H), 3.84 (s, 3H), 3.52 (c, J=7.1 Hz, 2H), 3.04 (s, 3H), 2.62 (s, 3H), 1.20 (t, J=7.1 Hz, 3H). IR (KBr): ν$_{máx}$ (cm$^{-1}$) 3430, 2963, 2934, 2834, 2252, 2211, 1261, 1235, 767. HPLC-MS (API-ES+, m/z) 383.1 (M+1)$^+$. Yield=83%.

Example 101

4-(Diethylamino)-2-(3,4-dimethoxybenzyl)-5-methylthieno[2,3-d]pyrimidine-6-carbonitrile

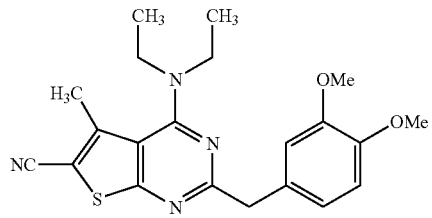

M.P.: 107-109° C.; $^1$H-NMR (CDCl$_3$, 300 MHz): δ (ppm) 6.95-6.89 (m, 2H), 6.78-6.74 (m, 1H), 4.06 (s, 2H), 3.85 (s, 3H), 3.83 (s, 3H), 3.49 (c, J=7.1 Hz, 4H), 2.62 (s, 3H), 1.14 (t, J=7.1 Hz, 6H). IR (KBr): ν$_{máx}$ (cm$^{-1}$) 3418, 2926, 2212, 1516, 1267, 1137, 1030. HPLC-MS (API-ES+, m/z) 397.1 (M+1)$^+$. Yield=37%.

Example 102

4-[Allyl(methyl)amino]-2-(3,4-dimethoxybenzyl)-5-methylthieno[2,3-d]pyrimidine-6-carbonitrile

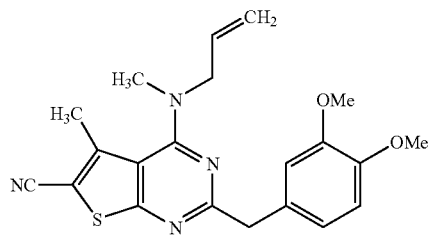

M.P.: 98-100° C.; $^1$H-NMR (CDCl$_3$, 300 MHz): δ (ppm) 6.97-6.91 (m, 2H), 6.79-6.76 (m, 1H), 5.87-5.82 (m, 1H), 5.28 (d, J=5.8 Hz, 1H), 5.24 (s, 1H), 4.08-4.05 (m, 3H), 3.87-3.82 (m, 7H), 3.00 (s, 3H), 2.64 (s, 3H). IR (KBr): ν$_{máx}$ (cm$^{-1}$) 3433, 2969, 2934, 2217, 1538, 1507, 1259, 1024, 798. Yield=55%.

Example 103

2-(3,4-Dimethoxybenzyl)-5-methyl-4-[methyl(prop-2-ynyl)amino]thieno[2,3-d]pyrimidine-6-carbonitrile

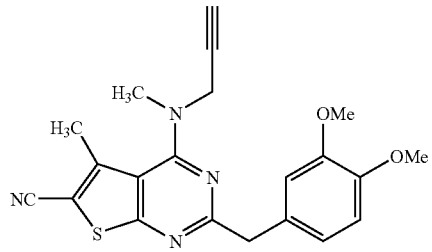

$^1$H-NMR (CDCl$_3$, 300 MHz): δ (ppm) 6.98-6.93 (m, 2H), 6.77 (d, J=7.9 Hz, 1H), 4.20 (s, 2H), 4.09 (s, 2H), 3.86 (s, 3H), 3.83 (s, 3H), 3.14 (s, 3H), 2.69 (s, 3H), 2.30 (bs, 1H). IR (KBr): ν$_{máx}$ (cm$^{-1}$) 3412, 3280, 2931, 2832, 2212, 1536, 1463, 1261, 1028, 911, 797, 730. HPLC-MS (API-ES+, m/z) 393.1 (M+1)$^+$. Yield=39%.

Example 104

2-(3,4-Dimethoxybenzyl)-4-[(2-hydroxyethyl)amino]-5-methylthieno[2,3-d]pyrimidine-6-carbonitrile

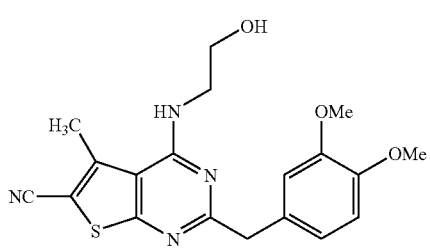

M.P.: 149-151° C.; $^1$H-NMR (CDCl$_3$, 300 MHz): δ (ppm) 6.93-6.88 (m, 2H), 6.77 (d, J=7.9 Hz, 1H), 6.00 (bs, 1H), 4.00 (s, 2H), 3.85-3.76 (m, 10 H), 3.09 (t, J=8.9 Hz, 1H), 2.73 (s, 3H). IR (KBr): ν$_{máx}$ (cm$^{-1}$) 3457, 3205, 2996, 2934, 2832, 2208, 1673, 1574, 1448, 1262, 796, 761, 647 HPLC-MS (API-ES+, m/z) 385.1 (M+1)$^+$. Yield=64%.

Example 105

2-(3,4-Dimethoxybenzyl)-4-[(2-hydroxyethyl)(methyl)amino]-5-methylthieno[2,3-d]pyrimidine-6-carbonitrile

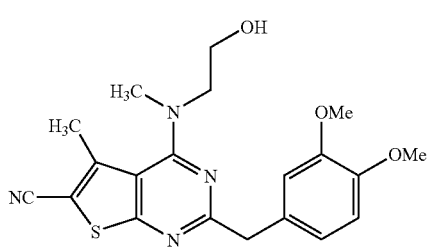

M.P.: 62-63° C.; $^1$H-NMR (CDCl$_3$, 300 MHz): δ (ppm) 6.94-6.85 (m, 2H), 6.80-6.74 (m, 1 H), 4.04 (m, 2H), 3.99-3.82 (m, 8H), 3.76-3.73 (m, 2H), 3.16 (s, 3H), 2.66 (m, 3H). IR (KBr): ν$_{máx}$ (cm$^{-1}$) 3426, 2932, 2211, 1661, 1542, 1514, 1463, 1261, 1026, 797. Yield=64%.

Example 106

2-(3,4-Dimethoxybenzyl)-4-[(2-methoxyethyl)amino]-5-methylthieno[2,3-d]pyrimidine-6-carbonitrile

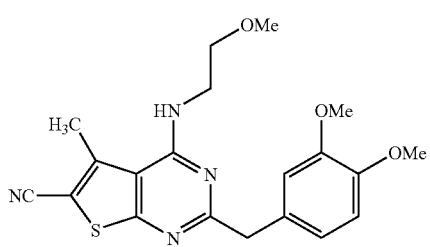

M.P.: 94-97° C.; $^1$H-NMR (CDCl$_3$, 300 MHz): δ (ppm) 6.95 (s, 1H), 6.86 (d, J=8.2 Hz, 1H), 6.76 (d, J=8.2 Hz, 1H), 5.96 (bs, 1H), 4.02 (s, 2H), 3.85 (s, 3H), 3.83 (s, 3H), 3.79 (t, J=5.1 Hz, 2H), 3.56 (t, J=5.1 Hz, 2H), 3.38 (s, 3H), 2.70 (s, 3H). IR (KBr): ν$_{máx}$ (cm$^{-1}$) 3454, 2931, 2833, 2211, 1573, 1549, 1260, 1234, 1190, 1154, 1138, 1123. HPLC-MS (API-ES+, m/z) 399.1 (M+1)$^+$. Yield=57%.

Example 107

4-[[2-(Dimethylamino)ethyl](methyl)amino]-5-methyl-2-(3,4,5-trimethoxyphenyl) thieno[2,3-d]pyrimidine-6-carbonitrile

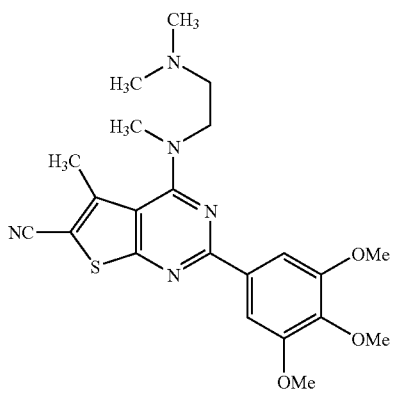

M.P.: 125-127° C.; $^1$H-NMR (CDCl$_3$, 300 MHz): δ (ppm) 7.75 (s, 2H), 3.97 (s, 6H), 3.91 (s, 3H), 3.7 (t, J=6.6 Hz, 2H), 3.20 (s, 3H), 2.70 (s, 3H), 2.61 (t, J=6.6 Hz, 2H), 2.24 (s, 6H). IR (KBr): ν$_{máx}$ (cm$^{-1}$) 3445, 2939, 2205, 1557, 1499, 1392, 1341, 1123, 780. HPLC-MS (API-ES+, m/z) 442.1 (M+1)$^+$. Yield=34%.

Example 108

5-Methyl-4-morpholin-4-yl-2-(3,4,5-trimethoxybenzyl)thieno[2,3-d]pyrimidine-6-carbonitrile

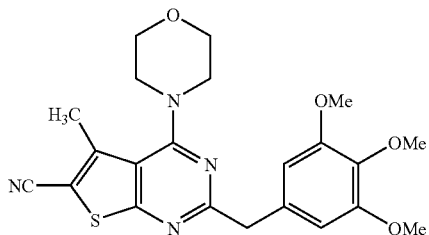

$^1$H-NMR (CDCl$_3$, 300 MHz): δ (ppm) 6.62 (s, 2H), 4.08 (s, 2H), 3.83 (s, 6H), 3.82-3.80 (m, 4H), 3.79 (s, 3H), 3.53-3.48 (m, 4H), 2.67 (s, 3H). IR (KBr): ν$_{máx}$ (cm$^{-1}$) 3435, 2961, 2932, 2854, 2212, 1680, 1591, 1380, 1365, 731. HPLC-MS (API-ES+, m/z) 441.1 (M+1)$^+$. Yield=75%.

Example 109

5-Methyl-4-(4-methylpiperazin-1-yl)-2-(3,4,5-trimethoxybenzyl)thieno[2,3-d]pyrimidine-6-carbonitrile

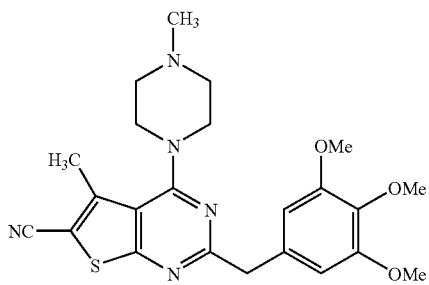

$^1$H-NMR (CDCl$_3$, 300 MHz): δ (ppm) 6.63 (s, 2H), 4.06 (s, 2H), 3.82 (s, 6H), 3.78 (s, 3H), 5.52 (bs, 4H), 2.65 (s, 3H), 2.52 (bs, 4H), 2.31 (s, 3H). IR (KBr): ν$_{máx}$ (cm$^{-1}$) 3369, 2938, 1534, 1494, 140, 1132, 1001, 783. Yield=90%.

Example 110

5-Methyl-4-(methylamino)-2-(3,4,5-trimethoxybenzyl)thieno[2,3-d]pyrimidine-6-carbonitrile

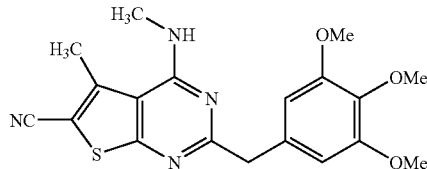

M.P.: 194-195° C.; $^1$H-NMR (CDCl$_3$, 300 MHz): δ (ppm) 6.67 (s, 2H), 5.52 (bs, 1H), 4.02 (s, 2H), 3.82 (s, 6H), 3.78 (s, 3H), 3.15 (d, J=4.7 Hz, 3H), 2.71 (s, 3H). IR (KBr): ν$_{máx}$ (cm$^{-1}$) 3437, 2945, 2213, 1574 1506, 1321, 1121, 635. Yield=25%.

Example 111

4-(Ethylamino)-5-methyl-2-(3,4,5-trimethoxybenzyl)thieno[2,3-d]pyrimidine-6-carbonitrile

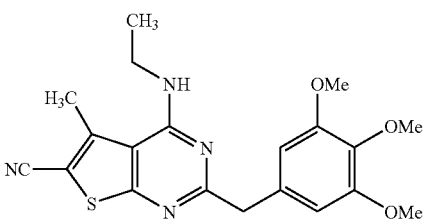

M.P.: 164-165° C.; $^1$H-NMR (CDCl$_3$, 300 MHz): δ (ppm) 6.65 (s, 2H), 5.47 (bs, 1H), 4.00 (s, 2H), 3.82 (s, 6H), 3.78 (s, 3H), 3.67-3.63 (m, 2H), 2.71 (s, 3H), 1.27 (t, J=7.1 Hz, 3H). IR (KBr): ν$_{máx}$ (cm$^{-1}$) 3437, 2945, 2213, 1574 1506, 1321, 1121, 635. Yield=27%.

Example 112

5-Methyl-4-(propylamino)-2-3,4,5-trimethoxybenzyl)thieno[2,3-d]pyrimidine-6-carbonitrile

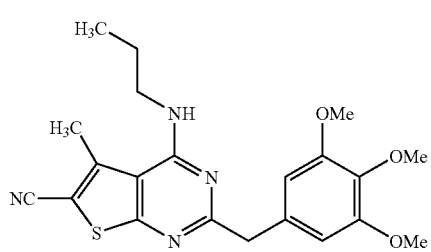

$^1$H-NMR (CDCl$_3$, 300 MHz): δ (ppm) 6.65 (s, 2H), 5.58 (m, 1H), 4.00 (s, 2H), 3.82 (s, 6H), 3.79 (s, 3H), 3.57 (c, J=7.1 Hz, 2H), 2.71 (s, 3H), 1.68 (m, 2H), 0.97 (t, J=7.1 Hz, 3H). IR (KBr): ν$_{máx}$ (cm$^{-1}$) 3426, 3000, 2961, 2937, 2874, 2211, 1505, 1239, 1126, 1004. HPLC-MS (API-ES+, m/z) 413.0 (M+1)$^+$. Yield=81%.

Example 113

4-(Isopropylamino)-5-methyl-2-(3,4,5-trimethoxybenzyl)thieno[2,3-d]pyrimidine-6-carbonitrile

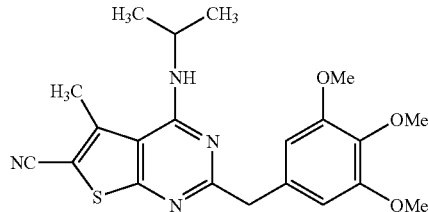

M.P.: 143-147° C.; $^1$H-NMR (CDCl$_3$, 300 MHz): δ (ppm) 6.63 (s, 3H), 5.27 (bs, 1H), 4.48 (m, 1H), 3.99 (s, 2H), 3.85 (s, 6H), 3.82 (s, 3H), 2.69 (s, 3H), 1.28 (d, J=6.3 Hz, 6H). IR (KBr): ν$_{má}$(cm$^{-1}$) 3440, 2970, 2837, 2210, 1568, 1548, 1504, 1450, 1239, 1006, 973, 732. HPLC-MS (API-ES+, m/z) 413.0 (M+1)$^+$. Yield=80%.

Example 114

4-(sec-Butylamino)-5-methyl-2-(3,4,5-trimethoxybenzyl)thieno[2,3-d]pyrimidine-6-carbonitrile

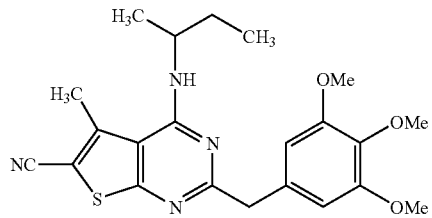

M.P.: 134-137° C.; $^1$H-NMR (CDCl$_3$, 300 MHz): δ (ppm) 6.63 (s, 2H), 5.27 (bs, 1H), 3.99 (s, 2H), 3.82 (s, 6H), 3.78 (s, 3H), 2.69 (s, 3H), 1.59 (m, 2H), 1.24 (d, J=6.4 Hz, 3H), 0.94 (t, J=7.3 Hz, 3H). IR (KBr): ν$_{máx}$ (cm$^{-1}$) 3460, 2965, 2936, 2836, 2360, 2341, 2210, 1127, 1006, 732. HPLC-MS (API-ES+, m/z) 427.1 (M+1)$^+$. Yield=82%.

Example 115

4-[(1-Ethylpropyl)amino]-5-methyl-2-(3,4,5-trimethoxybenzyl)thieno[2,3-d]pyrimidine-6-carbonitrile

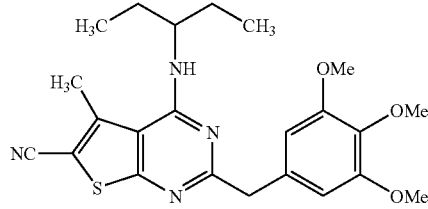

M.P.: 127-129° C.; $^1$H-NMR (CDCl$_3$, 300 MHz): δ (ppm) 6.61 (s, 2H), 5.24 (d, J=8.0 Hz, 1H), 4.30 (m, 1H), 3.98 (s, 2H), 3.85 (s, 6H), 3.82 (s, 3H), 2.70 (s, 3H), 2.63 (m, 2H), 1.52 (m, 2H), 0.90 (t, J=7.4 Hz, 6H). IR (KBr): ν$_{máx}$ (cm$^{-1}$) 3434, 2963, 2935, 2660, 2341, 2210, 1568, 1127, 1007, 805, 668. HPLC-MS (API-ES+, m/z) 441.1 (M+1)$^+$. Yield=84%.

Example 116

4-(tert-Butylamino)-5-methyl-2-(3,4,5-trimethoxybenzyl)thieno[2,3-d]pyrimidine-6-carbonitrile

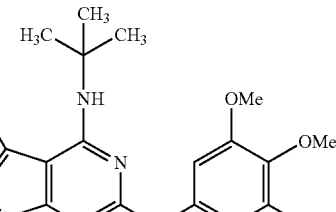

M.P.: 146-148° C.; $^1$H-NMR (CDCl$_3$, 300 MHz): δ (ppm) 6.59 (s, 2H), 5.44 (bs, 1H), 4.01 (s, 2H), 3.81 (s, 6H), 3.79 (s, 3H), 2.68 (s, 3H), 1.48 (s, 9H). IR (KBr): ν$_{máx}$ (cm$^{-1}$) 3468, 2962, 2937, 2837, 2209, 1421, 1127, 1007. HPLC-MS (API-ES+, m/z) 427.1 (M+1)$^+$. Yield=59%.

Example 117

4-(Cyclopropylamino)-5-methyl-2-(3,4,5-trimethoxybenzyl)thieno[2,3-d]pyrimidine-6-carbonitrile

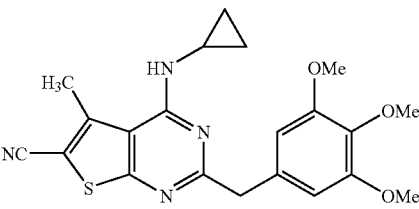

$^1$H-NMR (CDCl$_3$, 300 MHz): δ (ppm) 6.70 (s, 2H), 5.68 (bs, 1H), 4.06 (s, 2H), 3.84 (s, 6H), 3.80 (s, 3H), 2.67 (s, 3H), 0.92 (bs, 2H), 0.60 (bs, 2H). IR (KBr): ν$_{máx}$ (cm$^{-1}$) 3419, 2210, 1590, 1566, 1548, 1504, 1451, 1238, 1126. HPLC-MS (API-ES+, m/z) 411.1 (M+1)$^+$. Yield=68%.

Example 118

4-(Cyclobutylamino)-5-methyl-2-(3,4,5-trimethoxybenzyl)thieno[2,3-d]pyrimidine-6-carbonitrile

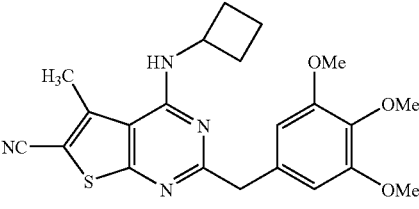

$^1$H-NMR (CDCl$_3$, 300 MHz): δ (ppm) 6.64 (s, 2H), 5.58 (d, J=6.2 Hz, 1H), 4.69 (m, 1H), 4.00 (s, 2H), 3.84 (s, 6H), 3.79 (s, 3H), 2.72 (s, 3H), 2.44 (m, 2H), 1.89 (m, 4H). IR (KBr): ν$_{máx}$ (cm$^{-1}$) 3433, 2939, 2250, 2211, 1574, 1322, 1241, 1125, 1006, 908, 729, 647. HPLC-MS (API-ES+, m/z) 425.0 (M+1)$^+$. Yield=82%.

Example 119

4-(Dimethylamino)-5-methyl-2-(3,4,5-trimethoxy-benzyl)thieno[2,3-d]pyrimidine-6-carbonitrile

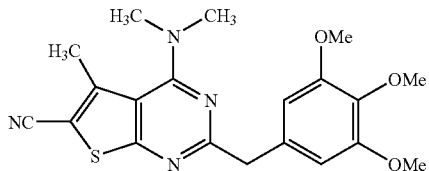

$^1$H-NMR (CDCl$_3$, 300 MHz): δ (ppm) 6.69 (s, 2H), 4.05 (s, 2H), 3.84 (s, 6H), 3.80 (s, 3H), 3.11 (s, 6H), 2.67 (s, 3H). IR (KBr): ν$_{máx}$ (cm$^{-1}$) 3433, 2939, 2250, 2211, 1574, 1322, 1241, 1125, 1006, 908, 729, 647. HPLC-MS (API-ES+, m/z) 399.1 (M+1)$^+$. Yield 80%.

Example 120

4-[Ethyl(methyl)amino]-5-methyl-2-(3,4,5-trimethoxybenzyl)thieno[2,3-d]pyrimidine-6-carbonitrile

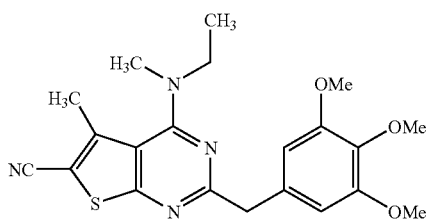

$^1$H-NMR (CDCl$_3$, 300 MHz): δ (ppm) 6.66 (s, 2H), 4.04 (s, 2H), 3.84 (s, 6H), 3.82 (s, 3H), 3.55 (c, J=7.1 Hz, 2H), 3.02 (s, 3H), 2.56 (s, 3H), 1.27 (t, J=7.1 Hz, 3H). IR (KBr): ν$_{máx}$ (cm$^{-1}$) 3435, 2935, 2837, 2211, 1591, 1538, 1499, 1032, 1006, 733. HPLC-MS (API-ES+, m/z) 413.2 (M+1)$^+$. Yield=81%.

Example 121

4-Diethylamino)-5-methyl-2-(3,4,5-trimethoxybenzyl)thieno[2,3-d]pyrimidine-6-carbonitrile

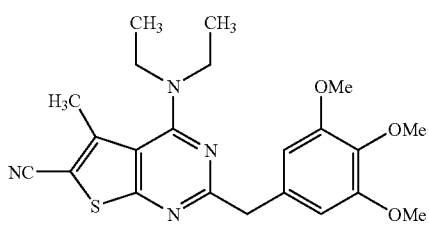

$^1$H-NMR (CDCl$_3$, 300 MHz): δ (ppm) 6.63 (s, 2H), 4.05 (s, 2H), 3.82 (s, 6H), 3.78 (s, 3H), 3.50 (c, J=7.1 Hz, 4H), 2.63 (s, 3H), 1.14 (t, J=7.1 Hz, 6H). IR (KBr): ν$_{máx}$ (cm$^{-1}$) 3372, 2936, 1588, 1534, 1132, 784. Yield=87%

Example 122

4-[Allyl(methyl)amino]-5-methyl-2-(3,4,5-trimethoxybenzyl)thieno[2,3-d]pyrimidine-6-carbonitrile

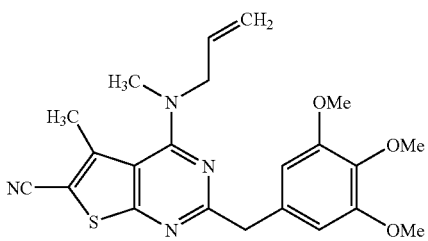

$^1$H-NMR (CDCl$_3$, 300 MHz): δ (ppm) 6.65 (s, 2H), 5.91-5.80 (m, 1H), 5.29-5.23 (m, 2H), 4.07 (d, J=6.2 Hz, 2H), 4.03 (s, 2H), 3.83 (s, 6H), 379 (s, 3H), 3.02 (s, 3H), 2.65 (s, 3H). IR (KBr): ν$_{máx}$ (cm$^{-1}$) 2936, 2212, 1591, 1538, 1239, 1127, 803. Yield=84%.

Example 123

5-Methyl-4-[methyl(prop-2-ynyl)amino]-2-(3,4,5-trimethoxybenzyl)thieno[2,3-d]pyrimidine-6-carbonitrile

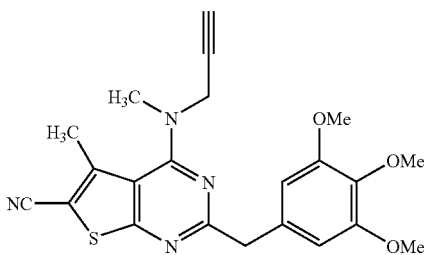

$^1$H-NMR (CDCl$_3$, 300 MHz): δ (ppm) 6.66 (s, 2H), 4.20 (d, J=2.0 Hz, 2H), 4.07 (s, 2H), 3.84 (s, 6H), 3.79 (s, 3H), 3.15 (s, 3H), 2.70 (s, 3H), 2.28 (bs, 1H). IR (KBr): ν$_{máx}$ (cm$^{-1}$) 3276, 2959, 2937, 2837, 2213, 1591, 1537, 1497, 1239, 1183, 736. HPLC-MS (API-ES+, m/z) 423.1 (M+1)$^+$. Yield=63%.

Example 124

4-[(2-Hydroxyethyl)amino]-5-methyl-2-(3,4,5-trimethoxybenzyl)thieno[2,3-d]pyrimidine-6-carbonitrile

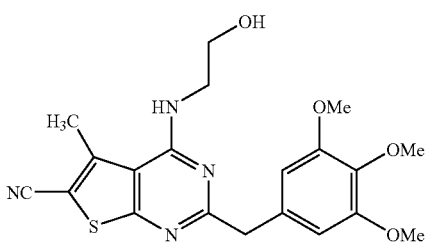

$^1$H-NMR (CDCl$_3$, 300 MHz): δ (ppm) 6.60 (s, 2H), 6.07 (ta, 1H), 3.98 (s, 2H), 3.84-3.72 (m, 4H), 3.81 (s, 6H), 3.77 (s, 3H), 2.70 (s, 3H). IR (KBr): ν$_{máx}$ (cm$^{-1}$) 3435, 3225, 2943, 2237, 2215, 1594, 1471, 1353, 1330, 1238, 1151, 1129. HPLC-MS (API-ES+, m/z) 415.1 (M+1)$^+$. Yield=97%.

Example 125

4-[(2-Methoxyethyl)amino]-5-methyl-2-(3,4,5-tri-methoxybenzyl)thieno[2,3-d]pyrimidine-6-carbonitrile

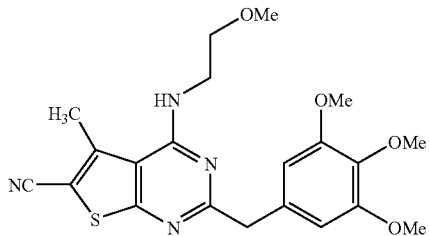

$^1$H-NMR (CDCl$_3$, 300 MHz): δ (ppm) 6.62 (s, 2H), 5.98 (bs, 1H), 4.00 (s, 2H), 3.82 (s, 6H), 6.62 (s, 2H), 5.98 (bs, 1H), 4.00 (s, 2H), 3.82 (s, 6H), 3.81-3.79 (m, 2H), 3.78 (s, 3H), 3.56 (t, J=5.0 Hz, 2H), 3.38 (s, 3H), 2.70 (s, 3H). IR (KBr): ν$_{máx}$ (cm$^{-1}$) 3435, 3225, 2943, 2237, 2215, 1594, 1471, 1353, 1330, 1238, 1151, 1129. HPLC-MS (API-ES+, m/z) 429.1 (M+1)$^+$. Yield=77%.

Example 126

4-[(2-Hydroxyethyl)(methyl)amino]-5-methyl-2-(3,4,5-trimethoxybenzyl)thieno[2,3-d]pyrimidine-6-carbonitrile

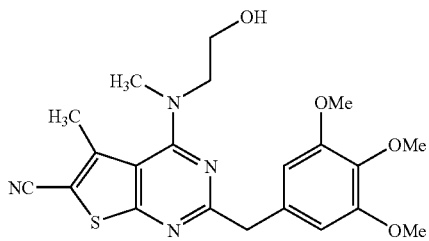

$^1$H-NMR (CDCl$_3$, 300 MHz): δ (ppm) 6.62 (s, 2H), 4.54 (bs, 1H), 4.02 (s, 2H), 3.88-3.72 (m, 4H), 3.83 (s, 6H), 3.79 (s, 3H), 3.16 (s, 3H), 2.66 (s, 3H). IR (KBr): ν$_{máx}$ (cm$^{-1}$) 3418, 2935, 2839, 2212, 1680, 1463, 1240, 1187, 1126, 1028, 1004, 737. HPLC-MS (API-ES+, m/z) 429.1 (M+1)$^+$. Yield 39%.

Example 127

5-methyl-4-(4-methylpiperazin-1-yl)-2-(2-phenylethyl)thieno[2,3-d]pyrimidine-6-carbonitrile

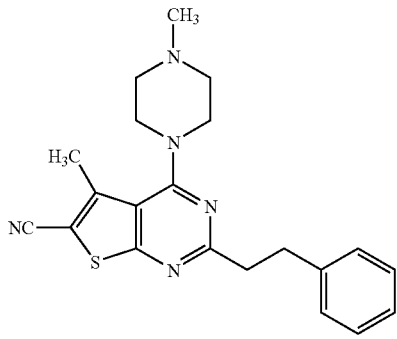

$^1$H-NMR (CDCl$_3$, 300 MHz): δ (ppm) 7.23 (m, 5H), 3.55 (t, J=4.6 Hz, 4H), 3.18 (bs, 4H), 2.69 (s, 3H), 2.55 (t, J=4.6 Hz, 4H), 2.36 (s, 3H). IR (KBr): ν$_{máx}$ (cm$^{-1}$) 3430, 3026, 2971, 2931, 2360, 2212, 1603, 1534, 1278, 1239, 1178, 1003, 699. HPLC-MS (API-ES+, m/z) 378.1 (M+1)$^+$. Yield 65%.

Example 128

4-(Cyclobutylamino)-5-methyl-2-(2-phenylethyl)thieno[2,3-d]pyrimidine-6-carbonitrile

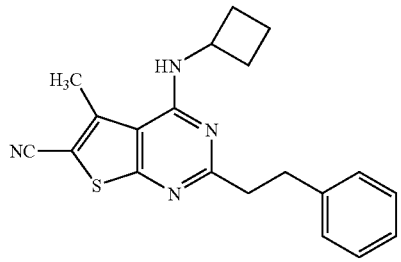

M.P.: 153-155° C.; $^1$H-NMR (CDCl$_3$, 300 MHz): δ (ppm) 7.20 (m, 5H), 5.56 (d, J=6.1 Hz, 1H), 4.69 (m, 1H), 3.09 (bs, 4H), 2.72 (s, 3H), 2.49 (m, 2H), 1.90 (m, 4H). IR (KBr): ν$_{máx}$ (cm$^{-1}$) 3422, 2980, 2942, 2360, 2211, 1575, 1558, 1546, 1231, 1201, 1150, 697. HPLC-MS (API-ES+, m/z) 349.1 (M+1)$^+$. Yield=85%.

Example 129

4-(Diethylamino)-5-methyl-2-(2-phenylethyl)thieno[2,3-d]pyrimidine-6-carbonitrile

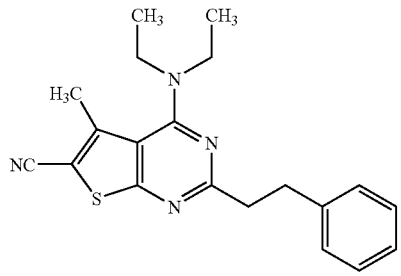

$^1$H-NMR (CDCl$_3$, 300 MHz): δ (ppm) 7.23 (m, 5H), 3.59 (c, J=6.95, 4H), 3.14 (bs, 4H), 2.65 (s, 3H), 1.90 (t, J=6.95 Hz, 6H). IR (KBr): ν$_{máx}$ (cm$^{-1}$) 3422, 2980, 2942, 2360, 2211, 1575, 1558, 1546, 1231, 1201, 1150, 697. Yield=75%.

Example 130

5-Methyl-4-(4-methylpiperazin-1-yl)-2-(3-phenylpropyl)thieno[2,3-d]pyrimidine-6-carbonitrile

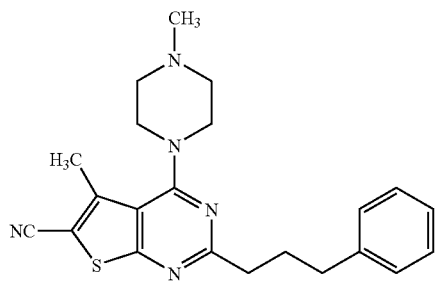

M.P.: 101-103° C.; $^1$H-NMR (CDCl$_3$, 300 MHz): δ (ppm) 7.26-7.14 (m, 5H), 3.54-3.51 (m, 4H), 2.89 (t, J=7.4 Hz, 2H), 2.71-2.67 (m, 5H), 2.56-2.53 (m, 4H), 2.33 (s, 3H), 2.18-2.09 (dt, J=7.4 Hz, 2H). IR (KBr): ν$_{máx}$ (cm$^{-1}$) 3436, 2933, 2841, 2749, 2205, 1535, 1363, 1139, 995, 700. HPLC-MS (API-ES+, m/z) 392.2 (M+1)$^+$. Yield=98%.

Example 131

4-(Diethylamino)-5-methyl-2-(3-phenylpropyl)thieno[2,3-d]pyrimidine-6-carbonitrile

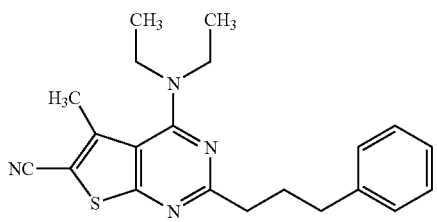

$^1$H-NMR (CDCl$_3$, 300 MHz): δ (ppm) 7.18-7.07 (m, 5H), 3.45 (c, J=6.9 Hz, 4H), 2.82 (t, J=7.4 Hz, 2H), 2.66-2.59 (m, 5H), 2.15-2.03 (m, 2H), 1.10 (t, J=6.9 Hz, 6H). IR (KBr): ν$_{máx}$ (cm$^{-1}$) 3419, 2969, 2931, 2211, 1534, 1497, 1149, 746, 700. HPLC-MS (API-ES+, m/z) 365.1 (M+1)$^+$. Yield=98%.

Example 132

2-(3,5-Dimethoxy-phenyl)-4-[(2-hydroxy-ethyl)-methyl-amino]-5-methyl-thieno[2,3-d]pyrimidine-6-carbonitrile

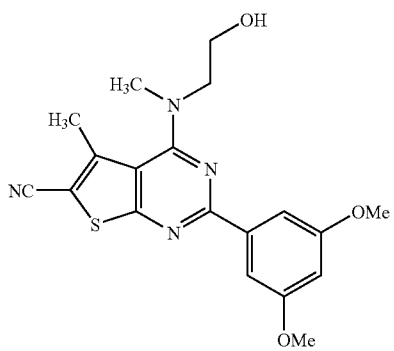

IR (KBr): ν$_{máx}$ (cm$^{-1}$) 3400, 2925, 2208, 1605, 1540, 1392, 1154, 787. $^1$H-NMR (CDCl$_3$, 300 MHz): δ (ppm) 7.55 (d, J=2.3 Hz, 2H), 6.57 (t, J=2.3 Hz, 1H), 3.98 (t, J=4.3 Hz, 2H), 3.90-3.88 (m, 2H), 3.87 (s, 6H), 3.22 (s, 3H), 2.71 (s, 3H).

Example 133

2-(3,5-Dimethoxy-phenyl)-5-methyl-4-morpholin-4-ylthieno[2,3-d]pyrimidine-6-carbonitrile

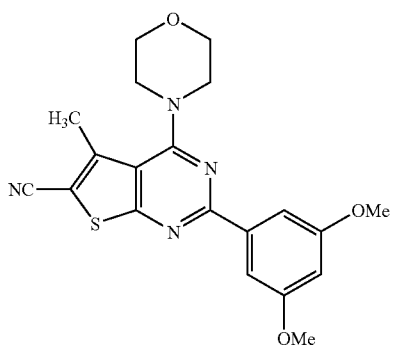

IR (KBr): ν$_{máx}$ (cm$^{-1}$) 3381, 2923, 2211, 1695, 1533, 992, 729. $^1$H-NMR (CDCl$_3$, 300 MHz): δ (ppm) 7.64 (d, J=2.5 Hz, 2H), 6.60 (t, J=2.5 Hz, 1H), 3.92-3.86 (m, 4H), 3.88-3.86 (m, 4H); 3.88 (s, 6H), 3.61-3.56 (m, 4H), 2.73 (s, 3H).

Example 134

2-(3,6-Dimethoxyphenyl)-4-ethylamino)-5-methylthieno[2,3-d]pyrimidine-6-carbonitrile

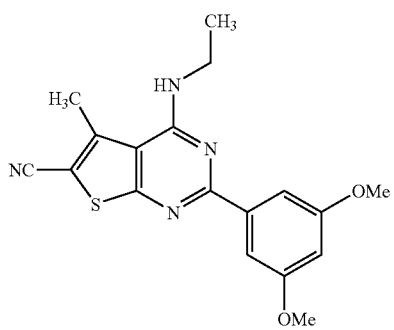

M.p. 207-208° C. IR (KBr): ν$_{máx}$ (cm$^{-1}$) 3481, 2934, 2209, 1554, 1209, 736. $^1$H-NMR (CDCl$_3$, 300 MHz): δ (ppm) 7.64 (s, 2H), 6.57 (s, 1H), 5.50 (bs, 1H), 3.87 (s, 6H), 3.74 (c, J=7.0 Hz, 2H), 2.75 (s, 3H), 1.36 (t, J=7.0 H, 3H). MS (IQ, m/z) 355.30 (M+1)$^+$.

Example 135

4-(Isobutylamino)-5-methyl-2-(3,4,5-trimethoxybenzyl)thieno[2,3-d]pyrimidine-6-carbonitrile

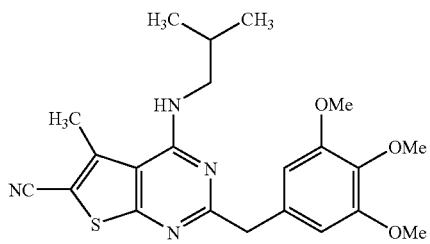

m.p. 129-131° C. IR (KBr): ν$_{máx}$ (cm$^{-1}$) 3432, 2949, 2834, 2211, 1592, 1506, 1449, 1422, 1402, 1130, 1011. $^1$H-NMR (CDCl$_3$, 300 MHz): δ (ppm) 6.63 (s, 2H), 5.28 (bt, 1H), 4.00 (s, 2H), 3.82 (s, 6H), 3.79 (s, 3H), 3.45 (t, J=6.1 Hz, 2H), 2.72 (s, 3H), 2.03-1.91 (m, 1H), 1.93 (d, J=6.6 Hz, 6H). HPLC-MS (API-ES+, m/z) 427.2 (M+1)$^+$.

COMPOSITION EXAMPLES

Composition Example 1

Preparation of Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention are mixed with 340.8 g of lactose and 85.2 g of microcrystalline cellulose. The mixture is subjected to compression moulding using a roller compactor to give a flake-like compressed material. The flake-like compressed material is pulverised using a hammer mill, and the pulverised material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

Preparation of Coated Tablets

Formulation:

| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water to prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethyl-cellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of Capsules

Formulation:

| Compound of the present invention | 5.0 mg |
| Lactose monohydrate | 200 mg |
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatine capsules.

Composition Example 4

Preparation of a Cream

Formulation:

| Compound of the present invention | 1% |
| Cetyl alcohol | 3% |
| Stearyl alcohol | 4% |
| Gliceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:
1. A compound of formula (I):

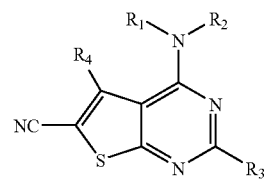

or a pharmaceutically acceptable salt thereof wherein
$R_1$ and $R_2$ either
(a) independently represent:
(i) a hydrogen atom
(ii) a group chosen from alkyl, alkenyl and alkynyl groups, wherein each alkyl, alkenyl and alkynyl group is independently and optionally substituted by one or more substituents chosen from halogen atoms, hydroxy, alkoxy, aryloxy, alkylthio, hydroxycarbonyl, alkoxycarbonyl, mono- and di-alkylaminoacyl, oxo, amino, and mono- and di-alkylamino groups; or
(iii) a group of formula —$(CH_2)_n$—$R^6$ wherein n is an integer from 0 to 4 and $R^6$ represents a cycloalkyl or cycloalkenyl group;
or
(b) $R_1$ and $R_2$ form, together with the nitrogen atom to which they are attached, a 3- to 8-membered ring comprising from 1 to 4 heteroatoms chosen from nitrogen, oxygen and sulphur, which ring is saturated or unsaturated and optionally substituted by one or more substituents chosen from halogen atoms, alkyl, hydroxy, alkoxy, acyl, hydroxycarbonyl, alkoxycarbonyl, alkylenedioxy, amino, mono- and di-alkylamino, mono- and di-alkylaminoacyl, nitro, cyano and trifluoromethyl groups;
$R_3$ is a group of formula —$(CH_2)_n$—G wherein n is an integer from 0 to 4 and G represents a monocyclic or bicyclic aryl or heteroaryl group comprising from one to four heteroatoms which group is optionally substituted by one or more substituents chosen from:
(i) halogen atoms;
(ii) alkyl groups, wherein each alkyl group is independently optionally substituted by one or more substituents chosen from halogen atoms; and
(iii) phenyl, hydroxy, hydroxyalkyl, alkoxy, alkylenedioxy, aryloxy, alkylthio, amino, mono- and di-alkylamino, acylamino, nitro, acyl, hydroxycarbonyl, alkoxycarbonyl, cyano, difluoromethoxy and trifluoromethoxy groups;
$R_4$ represents an alkyl or an aryl group;
with the proviso that the compound of formula (I) is not 5-methyl-2-phenyl-4-morpholin-4-ylthieno[2,3-d]pyrimidine-6-carbonitrile.

2. A compound of formula (II):

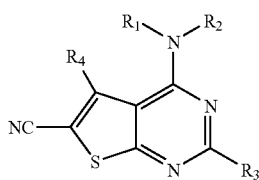

wherein $R_1$ and $R_2$ either:
a) independently represent hydrogen or a group chosen from an alkyl, alkenyl and alkynyl groups; wherein each alkyl, alkenyl and alkynyl group independently has from 1 to 4 carbon atoms and each is independently optionally substituted by one hydroxy group or a cycloalkyl group having from 3 to 6 carbon atoms; or
b) $R_1$ and $R_2$ form, together with the nitrogen atom to which they are attached, a 4- to 6-membered ring having from 1 to 2 heteroatoms chosen from nitrogen, oxygen and sulphur, which ring is optionally substituted by one or two $C_1$-$C_4$ alkyl groups, wherein each $C_1$-$C_4$ alkyl group is independently unsubstituted or substituted by one hydroxy group;
$R_3$ is a group of formula

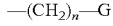

wherein n is an integer from 0 to 4 and G represents a monocyclic or bicyclic aryl or heteroaryl group comprising from one to four heteroatoms which group is optionally substituted by one or more substituents chosen from:
(iii) halogen atoms;
(iv) alkyl groups, wherein each alkyl group is independently optionally substituted by one or more substituents chosen from halogen atoms; and
(iii) phenyl, hydroxy, hydroxyalkyl, alkoxy, alkylenedioxy, aryloxy, alkylthio, amino, mono- and di-alkylamino, acylamino, nitro, acyl, hydroxycarbonyl, alkoxycarbonyl, cyano, difluoromethoxy and trifluoromethoxy groups;
$R_4$ represents an alkyl or an aryl group;
with the proviso that the compound of formula (I) is not 5-methyl-2-phenyl-4-morpholin-4-ylthieno[2,3-d]pyrimidine-6-carbonitrile.

3. A compound according to claim 1, wherein $R_1$ either:
a) represents a hydrogen atom or an alkyl group having from 1 to 4 carbon atoms
or
b) forms together with $R_2$ and with the nitrogen atom to which they are attached, a 4- to 6-membered ring having from 1 to 2 heteroatoms chosen from nitrogen and oxygen, which ring is optionally substituted by one or more substituents chosen from halogen atoms, alkyl and acyl groups.

4. A compound of formula III:

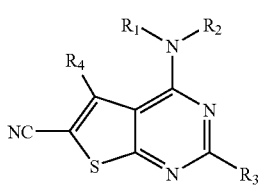

or a pharmaceutically acceptable salt thereof wherein:
$R_2$
(a) independently represents:
(iv) a hydrogen akin
(v) a group chosen from alkyl, alkenyl and alkynyl groups, wherein each alkyl, alkenyl and alkynyl group is independently and optionally substituted by one or more substituents chosen from halogen atoms, hydroxy, alkoxy, aryloxy, alkylthio, hydroxycarbonyl, alkoxycarbonyl, mono- and di-alkylaminoacyl, oxo, amino, and mono- and di-alkylamino groups; or
(vi) a group of formula —$(CH_2)_n$—$R^6$ wherein n is an integer from 0 to 4 and $R^6$ represents a cycloalkyl or cycloalkenyl group;
$R_2$ either:
a) represents a group chosen from alkyl, alkenyl, alkynyl, cycloalkyl, hydroxyalkyl and di-alkylamino groups;
or
b) forms together with $R_1$ and with the nitrogen atom to which they are attached, a 4- to 6-membered ring comprising from 1 to 2 heteroatoms chosen from nitrogen and oxygen, which ring is optionally substituted by one or more substituents chosen from halogen atoms, alkyl and acyl groups,
$R_3$ is a group of formula

wherein n is an integer from 0 to 4 and G represents a monocyclic or bicyclic aryl or heteroaryl group comprising from one to four heteroatoms which group is optionally substituted by one or more substituents chosen from:
(v) halogen atoms;
(vi) alkyl groups, wherein each alkyl group is independently optionally substituted by one or more substituents chosen from halogen atoms; and
(iii) phenyl, hydroxy, hydroxyalkyl, alkoxy, alkylenedioxy, aryloxy, alkylthio, amino, mono- and di-alkylamino, acylamino, nitro, acyl, hydroxycarbonyl, alkoxycarbonyl, cyano, difluoromethoxy and trifluoromethoxy groups; and
$R_4$ represents an alkyl or an aryl group;
with the proviso that the compound of formula (I) is not 5-methyl-2-phenyl-4-morpholin-4-ylthieno[2,3-d] pyrimidine-6-carbonitrile.

5. A compound according to claim 1, wherein $R_3$ represents a group of formula

wherein n is an integer from 0 to 4 and G represents a monocyclic aryl or heteroaryl group comprising one or one heteroatoms, which aryl or heteroaryl group is optionally substituted by one or more substituents chosen from:
(i) halogen atoms; and
(ii) unsubstituted $C_1$-$C_8$ alkyl, unsubstituted $C_1$-$C_8$ alkoxy, unsubstituted $C_1$-$C_3$ alkylenedioxy, nitro, trifluoromethyl and unsubstituted alkoxycarbonyl groups having a $C_1$-$C_8$ alkyl portion.

6. A compound according to claim 1, wherein $R_4$ is an unsubstituted $C_1$-$C_8$ alkyl or an unsubstituted $C_1$-$C_8$ alkyl or an unsubstituted $C_5$-$C_{14}$ aryl group.

7. A compound according to claim 6, wherein $R_4$ represents an unsubstituted $C_1$-$C_{14}$ alkyl group.

8. A compound according to claim 1, wherein $R_3$ represents a group chosen from phenyl, pyridyl and benzyl groups, wherein the phenyl, pyridyl and benzyl groups are optionally substituted by one or more substituents chosen from:
(i) halogen atoms; and
(ii) unsubstituted $C_1$-$C_8$ alkyl, unsubstituted $C_1$-$C_1$-$C_8$ alkoxy, unsubstituted $C_1$-$C_3$ alkylenedioxy, nitro, trifluoromethyl and unsubstituted alkoxycarbonyl groups having a $C_1$-$C_8$ alkyl portion.

9. A compound according to claim 8, wherein $R_3$ represents a phenyl or benzyl group substituted by one, two or three $C_1$-$C_6$ alkoxy groups.

10. A compound according to claim 9 wherein $R_1$ represents a hydrogen atom and $R_2$ represents
(i) a group chosen from alkyl, alkenyl and alkynyl groups, wherein each alkyl, alkenyl and alkynyl group is independently optionally substituted by one or more substituents chosen from halogen atoms, hydroxy, alkoxy, aryloxy, alkylthio, hydroxycarbonyl, alkoxycarbonyl, mono- and di-alkylaminoacyl, oxo, amino, and mono- and di-alkylamino groups; or
(ii) a group of formula

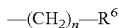

wherein n is an integer from 0 to 4 and $R^6$ represents a cycloalkyl or cycloalkenyl group.

11. A compound according to claim 1 chosen from:
4-(4-Ethylpiperazin-1-yl)-5-methyl-2-phenylthieno[2,3-d]pyrimidine-6-carbonitrile,
4-(4-Ethylpiperazin-1-yl)-2-(4-methoxyphenyl)-5-methylthieno[2,3-d]pyrimidine-6-carbonitrile,
4-(Diethylamino)-5-methyl-2-phenylthieno[2,3-d]pyrimidine-6-carbonitrile,
5-Methyl-2-phenyl-4-piperidin-1-ylthieno[2,3-d]pyrimidine-6-carbonitrile,
5-Methyl-2-(4-nitrophenyl)-4-piperidin-1-ylthieno[2,3-d]pyrimidine-6-carbonitrile,
2-(4-Methoxyphenyl)-5-methyl-4-piperidin-1-ylthieno[2,3-d]pyrimidine-6-carbonitrile,
5-Methyl-4-(4-methylpiperazin-1-yl)-2-(4 nitrophenyl)thieno[2,3-d]pyrimidine-6-carbonitrile,
5-Methyl-2-phenyl-4-piperazin-1-ylthieno[2,3-d]pyrimidine-6-carbonitrile,
2-(4-Methoxyphenyl)-5-methyl-4-(4-methylpiperazin-1-yl)thieno[2,3-d]pyrimidine-6-carbonitrile,
4-(Diethylamino)-2-(4-methoxyphenyl)-5-methylthieno[2,3-d]pyrimidine-6-carbonitrile,
2-(4-Methoxyphenyl)-5-methyl-4-pyrrolidin-1-ylthieno[2,3-d]pyrimidine-6-carbonitrile,
2(4-Methoxyphenyl)-5-methyl-4-piperazin-1-ylthieno[2,3-d]pyrimidine-6-carbonitrile,
5-Methyl-2-(4-nitrophenyl)-4-piperazin-1-ylthieno[2,3-d]pyrimidine-6-carbonitrile,
4-(Dibutylamino)-2-(4-methoxyphenyl)-5-methylthieno[2,3-d]pyrimidine-6-carbonitrile,
2-(4-Chlorophenyl)-5-methyl-4-(4-methylpiperazin-1-yl)thieno[2,3-d]pyrimidine-6-carbonitrile,
2-(3,4-Dimethoxyphenyl)-5-methyl-4-(4-methylpiperazin-1-yl)thieno[2,3-d]pyrimidine-6-carbonitrile,
4-[Ethyl(methyl)amino]-2-(4-methoxyphenyl)-5-methylthieno[2,3-d]pyrimidine-6-carbonitrile,
4-(Diethylamino)-5-methyl-2-(4-nitrophenyl)thieno[2,3-d]pyrimidine-6-carbonitrile,
2-(4-Chlorophenyl)-4-(diethylamino)-5-methylthieno[2,3-d]pyrimidine-6-carbonitrile,
4-(Diethylamino)-2-(3,4-dimethoxyphenyl)-5-methylthieno[2,3-d]pyrimidine-6-carbonitrile,
4-(Dimethylamino)-2-methoxyphenyl)-5-methylthieno[2,3-d]pyrimidine-6-carbonitrile,
2-(4-Methoxyphenyl)-5-methyl-4-morpholin-4-ylthieno[2,3-d]pyrimidine-6-carbonitrile,
2-(4-Chlorophenyl)-5-methyl-4-morpholin-4-ylthieno[2,3-d]pyrimidine-6-carbonitrile,
2-(4-Methoxyphenyl)-5-methyl-4-[methyl(prop-2-ynyl)amino]thieno[2,3-d]pyrimidine-6-carbonitrile,
4-[(2-Hydroxyethyl)(methyl)amino]-2-(4-methoxyphenyl)-5-methylthieno-[2,3-d]pyrimidine-6-carbonitrile,
2-(3,4-Dimethoxyphenyl)-4-[ethyl(methyl)amino]-5-methylthieno[2,3-d]pyrimidine-6-carbonitrile,
5-Methyl-2-(4-methylphenyl)-4-(4-methylpiperazin-1-yl)thieno[2,3-d]pyrimidine-6-carbonitrile,
4-(Diethylamino)-5-methyl-2-[4-(trifluoromethyl)phenyl]thieno[2,3-d]pyrimidine-6-carbonitrile,
4-[Allyl(methyl)amino]-2-(4-methoxyphenyl)-5-methylthieno[2,3-d]pyrimidine-6-carbonitrile,
2-(3,4-Dimethoxyphenyl)-4-[(2-hydroxyethyl)(methyl)amino]-5-methylthieno[2,3-d]pyrimidine-6-carbonitrile,
2-(3,4-Dimethoxyphenyl)-5-methyl-4-morpholin-4-ylthieno[2,3-d]pyrimidine-6-carbonitrile,
5-Methyl-2-(4-methylphenyl)-4-morpholin-4-ylthieno[2,3-d]pyrimidine-6-carbonitrile,
5-Methyl-4-(4-methylpiperazin-1-yl)-2-[4-(trifluoromethyl)phenyl]thieno[2,3-d]pyrimidine-6-carbonitrile,
2-(1,3-Benzodioxol-5-yl)-5-methyl-4-(4-methylpiperazin-1-yl)thieno[2,3-d]pyrimidine-6-carbonitrile,
4-(Diethylamino)-5-methyl-2-(4-methylphenyl)thieno[2,3-d]pyrimidine-6-carbonitrile,
2-(1,3-Benzodioxol-5-yl)-4-(diethylamino)-5-methylthieno[2,3-d]pyrimidine-6-carbonitrile,
2-(1,3-Benzodioxol-5-yl)-5-methyl-4-morpholin-4-ylthieno[2,3-d]pyrimidine-6-carbonitrile,
4-[Ethyl(methyl)amino]-5-methyl-2-pyridin-4-ylthieno[2,3-d]pyrimidine-6-carbonitrile,
4-[Ethyl(methyl)amino]-5-methyl-2-(3,4,5-trimethoxyphenyl)thieno[2,3-d]pyrimidine-6-carbonitrile,
2-Benzyl-5-methyl-4-(4-methylpiperazin-1-yl)thieno[2,3-d]pyrimidine-6-carbonitrile,
5-Methyl-4-morpholin-4-yl-2-pyridin-4-ylthieno[2,3-d]pyrimidine-6-carbonitrile,
4-[(2-Hydroxyethyl)(methyl)amino]-5-methyl-2-pyridin-4-ylthieno[2,3-d]pyrimidine-6-carbonitrile,
2-(1,3-Benzodioxol-5-yl)-4-[(2-hydroxyethyl)(methyl)amino]-5-methylthieno[2,3-d]pyrimidine-6-carbonitrile,
4-[(2-Hydroxyethyl)(methyl)amino]-5-methyl-2-(4-methyl phenyl)thieno[2,3-d]pyrimidine-6-carbonitrile,
4-(Diethylamino)-5-methyl-2-pyridin-4-ylthieno[2,3-d]pyrimidine-6-carbonitrile,
2-(3,4-Dimethoxyphenyl)-4-(dimethylamino)5-methylthieno[2,3-d]pyrimidine-6-carbonitrile,
2-(3,4-Dimethoxyphenyl)-5-methyl-4-(propylamino)thieno[2,3-d]pyrimidine-6-carbonitrile,
4-(Diethylamino)-5-methyl-2-(3,4,5-trimethoxyphenyl)thieno[2,3-d]pyrimidine-6-carbonitrile, 2-Benzyl-4-(diethylamino)-5-methylthieno[2,3-d]pyrimidine-6-carbonitrile,
5-Methyl-4-(4-methylpiperazin-1-yl)-2-phenylthieno[2,3-d]pyrimidine-6-carbonitrile,
5-Methyl-4-morpholin-4-yl-2-(3,4,5-trimethoxyphenyl)thieno[2,3-d]pyrimidine-6-carbonitrile,
4-[(2-Hydroxyethyl)methylamino]-5-methyl-2-(3,4,5-trimethoxyphenyl)thieno[2,3-d]pyrimidine-6-carbonitrile,
2-(3,5-Dimethoxyphenyl)-5-methyl-4-(4-methyl piperazin-1-yl)-thieno[2,3-d]pyrimidine-6-carbonitrile,
4-Diethylamino-2-(3,5-dimethoxyphenyl)-5-methylthieno[2,3-d]pyrimidine-6-carbonitrile,
2-(3,5-Dimethoxyphenyl)-4-(ethylmethylamino)-5-methylthieno[2,3-d]pyrimidine-6-carbonitrile,
4-(6-Cyano-4-diethylamino-5-methylthieno[2,3-d]pyrimidin-2-yl)-benzoic acid methyl ester,
4-[6-Cyano-4-(ethylmethylamino)-5-methylthieno[2,3-d]pyrimidin-2-yl]-benzoic acid methyl ester,
2-Benzyl-5-methyl-4-morpholin-4-yl-thieno[2,3-d]pyrimidine-6-carbonitrile,
2-Benzyl-4-[(2-hydroxyethyl)methylamino]-5-methylthieno[2,3-d]pyrimidine-6-carbonitrile,
5-Methyl-4-(4-methylpiperazin-1-yl)-2-(3,4,5-trimethoxyphenyl)thieno[2,3-d]pyrimidine-6-carbonitrile,
Methyl 4-(6-cyano-5-methyl-4-morpholin-4-ylthieno[2,3-d]pyrimidin-2-yl)benzoate,
Methyl 4[6-cyano-5-methyl-4-(4-methylpiperazin-1-yl)thieno[2,3-d]pyrimidin-2-yl]benzoate,
Methyl 4-[6-cyano-4-(dimethylamino)-5-methylthieno[2,3-d]pyrimidin-2-yl]benzoate,
Methyl 4-{6-cyano-4-[(2-hydroxyethyl)(methyl)amino]-5-methylthieno[2,3-d]pyrimidin-2-yl}benzoate,
5-methyl-4-(methylamino)-2-(3,4,5-trimethoxyphenyl)thieno[2,3-d]pyrimidine-6-carbonitrile,
4-(Dimethylamino)-5-methyl-2-(3,4,5-trimethoxyphenyl)thieno[2,3-d]pyrimidine-6-carbonitrile,
4-(Ethylamino)-5-methyl-2-(3,4,5-trimethoxyphenyl)thieno[2,3-d]pyrimidine-6-carbonitrile,
5-Methyl-4-(propylamino)-2-(3,5-trimethoxyphenyl)thieno[2,3-d]pyrimidine-6-carbonitrile,
4-(Butylamino)-5-methyl-2-(3,4,5-trimethoxyphenyl)thieno[2,3-d]pyrimidine-6-carbonitrile,
4-(Isopropylamino)-5-methyl-2-(3,4,5-trimethoxyphenyl)thieno[2,3-d]pyrimidine-6-carbonitrile,
4-(sec-Butylamino)-5-methyl-2-(3,4,5-trimethoxyphenyl)thieno[2,3-d]pyrimidine-6-carbonitrile,
4-(Isobutylamino)-5-methyl-2-(3,4,5-trimethoxyphenyl)thieno[2,3-d]pyrimidine-6-carbonitrile,
4-[(1-Ethylpropyl)amino]-5-methyl-2-(3,4,5-trimethoxyphenyl)thieno[2,3-d]pyrimidine-6-carbonitrile,
4-(tert-Butylamino)-5-methyl-2-(3,4,5-trimethoxyphenyl)thieno[2,3-d]pyrimidine-6-carbonitrile,
4-(Cyclopropylamino)-5-methyl-2-(3,4,5-trimethoxyphenyl)thieno[2,3-d]pyrimidine-6-carbonitrile,
4-(Cyclobutylamino)-5-methyl-2-(3,4,5-trimethoxyphenyl)thieno[2,3-d]pyrimidine-6-carbonitrile,
4-(Cyclopentylamino)-5-methyl-2-(3,4,5-trimethoxyphenyl)thieno[2,3-d]pyrimidine-6-carbonitrile,
4-[Allyl(methyl)amino]-5-methyl-2-(3,4,5-trimethoxyphenyl)thieno[2,3-d]pyrimidine-6-carbonitrile,
5-Methyl-4-[methyl(prop-2-ynyl)amino]-2-(3,4,5-trimethoxyphenyl)thieno[2,3-d]pyrimidine-6-carbonitrile,
4-[(2-Hydroxyethyl)amino]-5-methyl-2-(3,4,5-trimethoxyphenyl)thieno[2,3-d]pyrimidine-6-carbonitrile,
4-[(2-Methoxyethyl)amino]-5-methyl-2-(3,4,5-trimethoxyphenyl)thieno[2,3-d]pyrimidine-6-carbonitrile,
4-{[2-(Dimethylamino)ethyl]amino}-5-methyl-2-(3,4,5-trimethoxyphenyl)thieno[2,3-d]pyrimidine-6-carbonitrile,
5-Methyl-4-(3-methylpiperazin-1-yl)-2-(3,4,5-trimethoxyphenyl)thieno[2,3-d]pyrimidine-6-carbonitrile,
4-(3,5-Dimethylpiperazin-1-yl)-5-methyl-2-(3,4,5-trimethoxyphenyl)thieno[2,3-d]pyrimidine-6-carbonitrile,
4-(4-Acetylpiperazin-1-yl)-5-methyl-2-(3,4,5-trimethoxyphenyl)thieno[2,3-d]pyrimidine-6-carbonitrile,
4-[(2-Aminoethyl)(methyl)amino]-5-methyl-2-(3,4,5-trimethoxyphenyl)thieno[2,3-d]pyrimidine-6-carbonitrile,
N-[6-Cyano-5-methyl-2-(3,4,5-trimethoxyphenyl)thieno[2,3-d]pyrimidin-4-yl]-beta-alanine,
5-Methyl-4-(1H-pyrazol-1-yl)-2-(3,4,5-trimethoxyphenyl)thieno[2,3-d]pyrimidine-6-carbonitrile,
4-(1H—Imidazol-1-yl)-5-methyl-2-(3,4,5-trimethoxyphenyl)thieno[2,3-d]pyrimidine-6-carbonitrile,
5-Methyl-4-(2H-1,2,3-triazol-2-yl)-2-(3,4,5-trimethoxyphenyl)thieno[2,3-d]pyrimidine-6-carbonitrile,
5-Methyl-4-(1H-1,2,4-triazol-1-yl)-2-(3,4,5-trimethoxyphenyl)thieno[2,3-d]pyrimidine-6-carbonitrile,
2-(3,4-Dimethoxybenzyl)-5-methyl-4-morpholin-4-ylthieno[2,3-d]pyrimidine-6-carbonitrile,
2-(3,4-Dimethoxybenzyl)-5-methyl-4-(4-methyl piperazin-1-yl)thieno[2,3-d]pyrimidine-6-carbonitrile,
2-(3,4-Dimethoxybenzyl)-5-methyl-4-(methylamino)thieno[2,3-d]pyrimidine-6-carbonitrile,
2-(3,4-Dimethoxybenzyl)-4-(ethylamino)-5-methylthieno[2,3-d]pyrimidine-6-carbonitrile,
2-(3,4-Dimethoxybenzyl)-5-methyl-4-(propylamino)thieno[2,3-d]pyrimidine-6-carbonitrile,
4-(Cyclopropylamino)-2-(3,4-dimethoxybenzyl)-5-methylthieno[2,3-d]pyrimidine-6-carbonitrile,
4-(Cyclobutylamino)-2-(3,4-dimethoxybenzyl)-5-methylthieno[2,3-d]pyrimidine-6-carbonitrile,
2-(3,4-Dimethoxybenzyl)-4-(dimethylamino)-5-methylthieno[2,3-d]pyrimidine-6-carbonitrile,
2-(3,4-Dimethoxybenzyl)-4-[ethyl(methyl)amino]-5-methylthieno[2,3-d]pyrimidine-6-carbonitrile,
4-(Diethylamino)-2-(3,4-dimethoxybenzyl)-5-methylthieno[2,3-d]pyrimidine-6-carbonitrile,
4-[Allyl(methyl)amino]-2-(3,4-dimethoxybenzyl)-5-methylthieno[2,3-d]pyrimidine-6-carbonitrile,
2-(3,4-Dimethoxybenzyl)-5-methyl-4-[methyl(prop-2-ynyl)amino]thieno[2,3-d]pyrimidine-6-carbonitrile,
2-(3,4-Dimethoxybenzyl)-4-[(2-hydroxyethyl)amino]-5-methylthieno[2,3-d]pyrimidine-6-carbonitrile,
2-(3,4-Dimethoxybenzyl)-4-[(2-hydroxyethyl)(methyl)amino]-5-methylthieno[2,3-d]pyrimidine-6-carbonitrile,
2-(3,4-Dimethoxybenzyl)-4-[(2-methoxyethyl)amino]-5-methylthieno[2,3-d]pyrimidine-6-carbonitrile,
4-[[2-(Dimethylamino)ethyl](methyl)amino]-5-methyl-2-(3,4,5-trimethoxyphenyl) thieno[2,3-d]pyrimidine-6-carbonitrile,
5-Methyl-4-morpholin-4-yl-2-(3,4,5-trimethoxybenzyl)thieno[2,3-d]pyrimidine-6-carbonitrile,
5-Methyl-4-(4-methyl piperazin-1-yl)-2-(3,4,5-trimethoxybenzyl)thieno[2,3-d]pyrimidine-6-carbonitrile,
5-Methyl-4-(methylamino)-2-(3,4,5-trimethoxybenzyl)thieno[2,3-d]pyrimidine-6-carbonitrile,
4-(Ethylamino)-5-methyl-2-(3,4,5-trimethoxybenzyl)thieno[2,3-d]pyrimidine-6-carbonitrile,
5-Methyl-4-(propylamino)-2-(3,4,5-trimethoxybenzyl)thieno[2,3-d]pyrimidine-6-carbonitrile,
4-(Isopropylamino)-5-methyl-2-(3,4,5-trimethoxybenzyl)thieno[2,3-d]pyrimidine-6-carbonitrile, 4-(sec-Butylamino)-5-methyl-2-(3,4,5-trimethoxybenzyl)thieno[2,3-d]pyrimidine-6-carbonitrile,
4-[(1-Ethylpropyl)amino]-5-methyl-2-(3,4,5-trimethoxybenzyl)thieno[2,3-d]pyrimidine-6-carbonitrile,
4-(tert-Butylamino)-5-methyl-2-(3,4,5-trimethoxybenzyl)thieno[2,3-d]pyrimidine-6-carbonitrile,
4-(Cyclopropylamino)-5-methyl-2-(3,4,5-trimethoxybenzyl)thieno[2,3-d]pyrimidine-6-carbonitrile,
4-(Cyclobutylamino)-5-methyl-2-(3,4,5-trimethoxybenzyl)thieno[2,3-d]pyrimidine-6-carbonitrile,
4-(Dimethylamino)-5-methyl-2-(3,4,5-trimethoxybenzyl)thieno[2,3-d]pyrimidine-6-carbonitrile,
4-[Ethyl(methyl)amino]-5-methyl-2-(3,4,5-trimethoxybenzyl)thieno[2,3-d]pyrimidine-6-carbonitrile,
4-(Diethylamino)-5-methyl-2-(3,4,5-trimethoxybenzyl)thieno[2,3-d]pyrimidine-6-carbonitrile,
4-[Allyl(methyl)amino]-5-methyl-2-(3,4,5-trimethoxybenzyl)thieno[2,3-d]pyrimidine-6-carbonitrile,
5-Methyl-4-[methyl(prop-2-ynyl)amino]-2-(3,4,5-trimethoxybenzyl)thieno[2,3-d]pyrimidine-6-carbonitrile,
4-[(2-Hydroxyethyl)amino]-5-methyl-2-(3,4,5-trimethoxybenzyl)thieno[2,3-d]pyrimidine-6-carbonitrile,
4-[(2-Methoxyethyl)amino]-5-methyl-2-(3,4,5-trimethoxybenzyl)thieno[2,3-d]pyrimidine-6-carbonitrile,
4-[(2-Hydroxyethyl)(methyl)amino]-5-methyl-2-(3,4,5-trimethoxybenzyl)thieno[2,3-d]pyrimidine-6-carbonitrile,
5-methyl-4-(4-methylpiperazin-1-yl)-2-(2-phenylethyl)thieno[2,3-d]pyrimidine-6-carbonitrile,
4-(Cyclobutylamino)-5-methyl-2-(2-phenylethyl)thieno[2,3-d]pyrimidine-6-carbonitrile,
4-(Diethylamino)-5-methyl-2-(2-phenylethyl)thieno[2,3-d]pyrimidine-6-carbonitrile,
5-Methyl-4-(4-methylpiperazin-1-yl)-2-(3-phenylpropyl)thieno[2,3-d]pyrimidine-6-carbonitrile,
4-(Diethylamino)-5-methyl-2-(3-phenylpropyl)thieno[2,3-d]pyrimidine-6-carbonitrile,
2-(3,5-Dimethoxy-phenyl)-4-[(2-hydroxy-ethyl)-methyl-amino]-5-methyl-thieno[2,3-d]pyrimidine-6-carbonitrile,
2-(3,5-Dimethoxy-phenyl)-5-methyl-4-morpholin-4-ylthieno[2,3-d]pyrimidine-6-carbonitrile,
2-(3,5-Dimethoxyphenyl)-4-(ethylamino)-5-methylthieno[2,3-d]pyrimidine-6-carbonitrile,
4-(Isobutylamino)-5-methyl-2-(3,4,5-trimethoxybenzyl)thieno[2,3-d]pyrimidine-6-carbonitrile,
and pharmaceutically acceptable salts thereof.

12. A process for the preparation of a compound as claimed in claim 1, comprising:

(a) reacting the thienopyrimidinone of formula (VI)

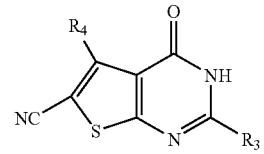

(VI)

with a chlorinating agent, (b) removing after cooling the excess of chlorinating agent, (c) optionally isolating the chlorothienopyrimidine of formula (VII)

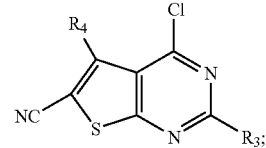

(VII)

(d) reacting the chlorothienopyrimidine of formula (VII) with an amine (VIII)

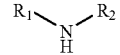

(VIII)

in a closed atmosphere at temperatures ranging from 40° C. to 120° C. to produce a compound of formula (I):

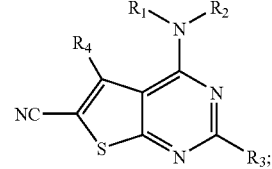

(I)

and (e) optionally preparing a pharmaceutically acceptable salt from a compound of formula (I).

13. A pharmaceutical composition comprising at least one compound according to claim 1 and a pharmaceutically acceptable diluent or carrier.

* * * * *

UNITED STATES PATENT AND TRADEMARK OFFICE
CERTIFICATE OF CORRECTION

PATENT NO. : 7,662,814 B2  Page 1 of 1
APPLICATION NO. : 10/542940
DATED : February 16, 2010
INVENTOR(S) : Emma Terricabras Belart et al.

It is certified that error appears in the above-identified patent and that said Letters Patent is hereby corrected as shown below:

Claim 8, col. 77, line 20, "$C_1$-$C_1$-$C_8$" should read --$C_1$-$C_8$--.

Claim 11, col. 77, line 52,
"5-Methyl-4-(4-methylpiperazin-1-yl)-2-(4    nitrophenyl)" should read
--5-Methyl-4-(4-methylpiperazin-1-yl)-2-(4-nitrophenyl)--.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,662,814 B2
APPLICATION NO. : 10/542940
DATED : February 16, 2010
INVENTOR(S) : Emma Terricabras Belart et al.

Page 1 of 1

It is certified that error appears in the above-identified patent and that said Letters Patent is hereby corrected as shown below:

Claim 5, col. 77, lines 2-3, "one or one heteroatoms" should read
--one heteroatom--.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,662,814 B2 Page 1 of 1
APPLICATION NO. : 10/542940
DATED : February 16, 2010
INVENTOR(S) : Terricabras Belart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this

Thirtieth Day of November, 2010

David J. Kappos
*Director of the United States Patent and Trademark Office*